US012752005B2

(12) United States Patent
Brunetta

(10) Patent No.: US 12,752,005 B2
(45) Date of Patent: Oct. 6, 2026

(54) COMPOSITIONS AND METHODS OF TREATING LUPUS NEPHRITIS

(71) Applicant: Genentech, Inc., South San Francisco, CA (US)

(72) Inventor: Paul Brunetta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 19/285,781

(22) Filed: Jul. 30, 2025

(65) Prior Publication Data

US 2025/0368749 A1 Dec. 4, 2025

Related U.S. Application Data

(63) Continuation of application No. 19/039,642, filed on Jan. 28, 2025, now abandoned, which is a continuation of application No. 18/045,313, filed on Oct. 10, 2022, now abandoned, which is a continuation of application No. 16/363,836, filed on Mar. 25, 2019, now abandoned, which is a continuation of application No. 15/151,449, filed on May 10, 2016, now abandoned.

(60) Provisional application No. 62/300,052, filed on Feb. 25, 2016, provisional application No. 62/159,876, filed on May 11, 2015.

(51) Int. Cl.

| | |
|---|---|
| ***C07K 16/28*** | (2006.01) |
| ***A61K 31/135*** | (2006.01) |
| ***A61K 31/138*** | (2006.01) |
| ***A61K 31/167*** | (2006.01) |
| ***A61K 31/365*** | (2006.01) |
| ***A61K 31/5377*** | (2006.01) |
| ***A61K 31/573*** | (2006.01) |
| ***A61K 39/395*** | (2006.01) |
| ***A61K 45/06*** | (2006.01) |
| ***A61P 13/12*** | (2006.01) |
| ***A61P 37/06*** | (2006.01) |
| *A61K 39/00* | (2006.01) |

(52) U.S. Cl.

CPC ........ *A61K 39/3955* (2013.01); *A61K 31/135* (2013.01); *A61K 31/138* (2013.01); *A61K 31/167* (2013.01); *A61K 31/365* (2013.01); *A61K 31/5377* (2013.01); *A61K 31/573* (2013.01); *A61K 45/06* (2013.01); *A61P 13/12* (2018.01); *A61P 37/06* (2018.01); *C07K 16/2887* (2013.01); *A61K 2039/505* (2013.01); *A61K 2039/507* (2013.01); *A61K 2039/545* (2013.01); *C07K 2317/24* (2013.01); *C07K 2317/41* (2013.01); *C07K 2317/524* (2013.01); *C07K 2317/70* (2013.01); *C07K 2317/71* (2013.01); *C07K 2317/73* (2013.01); *C07K 2317/734* (2013.01); *C07K 2317/77* (2013.01)

(58) Field of Classification Search

None

See application file for complete search history.

(56) References Cited

U.S. PATENT DOCUMENTS

| | | | |
|---|---|---|---|
| 4,120,649 | A | 10/1978 | Schechter |
| 4,665,007 | A | 5/1987 | Cservak et al. |
| 4,676,980 | A | 6/1987 | Segal |
| 4,737,456 | A | 4/1988 | Weng |
| 4,808,614 | A | 2/1989 | Hertel |
| 4,816,567 | A | 3/1989 | Cabilly |
| 5,114,721 | A | 5/1992 | Cohen |
| 5,208,020 | A | 5/1993 | Chari |
| 5,416,064 | A | 5/1995 | Chari |
| 5,464,826 | A | 11/1995 | Grindey et al. |
| 5,500,362 | A | 3/1996 | Robinson |
| 5,545,806 | A | 8/1996 | Lonberg |
| 5,545,807 | A | 8/1996 | Surani |
| 5,569,825 | A | 10/1996 | Lonberg |
| 5,571,894 | A | 11/1996 | Wels |
| 5,587,458 | A | 12/1996 | King |
| 5,591,828 | A | 1/1997 | Bosslet |
| 5,624,821 | A | 4/1997 | Winter |
| 5,625,126 | A | 4/1997 | Lonberg |
| 5,633,425 | A | 5/1997 | Lonberg |
| 5,635,483 | A | 6/1997 | Pettit |
| 5,641,870 | A | 6/1997 | Rinderknecht |

(Continued)

FOREIGN PATENT DOCUMENTS

| | | | |
|---|---|---|---|
| CN | 1993142 | A | 7/2007 |
| CN | 102470171 | A | 5/2012 |

(Continued)

OTHER PUBLICATIONS

Reddy et al. (Annals of the Rheumatic Diseases 2013; 72:A162) (Year: 2013).*

(Continued)

*Primary Examiner* — Sharon X Wen

(74) *Attorney, Agent, or Firm* — Leason Ellis LLP; Brian M. Gummow

(57) ABSTRACT

The invention provides methods for treating or delaying progression of lupus nephritis in an individual that has lupus. In some embodiments, the methods comprise administering to the individual an effective amount of a type II anti-CD20 antibody. The invention also provides methods for treating or delaying progression of rheumatoid arthritis (RA) or systemic lupus erythematosus (SLE) in an individual. In some embodiments, the methods comprise administering an effective amount of an anti-CD20 antibody.

51 Claims, 13 Drawing Sheets

Specification includes a Sequence Listing.

(56) References Cited

U.S. PATENT DOCUMENTS

| | | | |
|---|---|---|---|
| 5,648,237 | A | 7/1997 | Carter |
| 5,648,260 | A | 7/1997 | Winter |
| 5,661,016 | A | 8/1997 | Lonberg |
| 5,677,180 | A | 10/1997 | Robinson et al. |
| 5,712,374 | A | 1/1998 | Kuntsmann |
| 5,714,586 | A | 2/1998 | Kunstmann |
| 5,721,108 | A | 2/1998 | Robinson |
| 5,731,168 | A | 3/1998 | Carter |
| 5,736,137 | A | 4/1998 | Anderson |
| 5,739,116 | A | 4/1998 | Hamann |
| 5,750,373 | A | 5/1998 | Garrard |
| 5,767,285 | A | 6/1998 | Hamann |
| 5,770,429 | A | 6/1998 | Lonberg et al. |
| 5,770,701 | A | 6/1998 | Mcgahren |
| 5,770,710 | A | 6/1998 | Mcgahren |
| 5,773,001 | A | 6/1998 | Hamann |
| 5,776,456 | A | 7/1998 | Anderson |
| 5,780,588 | A | 7/1998 | Pettit |
| 5,789,199 | A | 8/1998 | Joly |
| 5,821,337 | A | 10/1998 | Carter |
| 5,840,523 | A | 11/1998 | Simmons |
| 5,843,439 | A | 12/1998 | Anderson et al. |
| 5,869,046 | A | 2/1999 | Presta |
| 5,877,296 | A | 3/1999 | Hamann |
| 5,959,177 | A | 9/1999 | Hein |
| 6,040,498 | A | 3/2000 | Stomp et al. |
| 6,075,181 | A | 6/2000 | Kucherlapati |
| 6,120,767 | A | 9/2000 | Robinson et al. |
| 6,127,526 | A | 10/2000 | Blank |
| 6,150,584 | A | 11/2000 | Kucherlapati |
| 6,171,586 | B1 | 1/2001 | Lam |
| 6,194,551 | B1 | 2/2001 | Idusogie |
| 6,248,516 | B1 | 6/2001 | Winter |
| 6,267,958 | B1 | 7/2001 | Andya |
| 6,333,398 | B1 | 12/2001 | Blank |
| 6,399,061 | B1 | 6/2002 | Anderson et al. |
| 6,417,335 | B1 | 7/2002 | Basey et al. |
| 6,417,429 | B1 | 7/2002 | Hein |
| 6,420,548 | B1 | 7/2002 | Vezina |
| 6,455,043 | B1 | 9/2002 | Grillo-lopez |
| 6,489,447 | B1 | 12/2002 | Basey et al. |
| 6,602,684 | B1 | 8/2003 | Umana |
| 6,630,579 | B2 | 10/2003 | Chari |
| 6,652,852 | B1 | 11/2003 | Robinson et al. |
| 6,682,734 | B1 | 1/2004 | Anderson et al. |
| 6,737,056 | B1 | 5/2004 | Presta |
| 6,797,814 | B2 | 9/2004 | Blank |
| 6,846,476 | B2 | 1/2005 | White |
| 6,893,625 | B1 | 5/2005 | Robinson et al. |
| 6,896,885 | B2 | 5/2005 | Hanna |
| 6,982,321 | B2 | 1/2006 | Winter |
| 6,991,790 | B1 | 1/2006 | Lam et al. |
| 7,041,870 | B2 | 5/2006 | Tomizuka |
| 7,087,409 | B2 | 8/2006 | Barbas, III |
| 7,125,978 | B1 | 10/2006 | Vezina |
| 7,189,826 | B2 | 3/2007 | Rodman |
| 7,332,581 | B2 | 2/2008 | Presta |
| 7,371,826 | B2 | 5/2008 | Presta |
| 7,381,560 | B2 | 6/2008 | Anderson |
| 7,422,739 | B2 | 9/2008 | Anderson et al. |
| 7,498,298 | B2 | 3/2009 | Doronina |
| 7,504,256 | B1 | 3/2009 | Ogawa |
| 7,517,670 | B2 | 4/2009 | Umana et al. |
| 7,521,541 | B2 | 4/2009 | Eigenbrot |
| 7,527,791 | B2 | 5/2009 | Adams |
| 7,531,645 | B2 | 5/2009 | Basey et al. |
| 7,601,335 | B2 | 10/2009 | Mccutcheon et al. |
| 7,682,612 | B1 | 3/2010 | White et al. |
| 7,708,994 | B2 | 5/2010 | Benyunes |
| 7,744,877 | B2 | 6/2010 | Anderson et al. |
| 7,820,161 | B1 | 10/2010 | Curd et al. |
| 7,906,329 | B2 | 3/2011 | Umana et al. |
| 7,976,838 | B2 | 7/2011 | Benyunes |
| 8,883,980 | B2 | 11/2014 | Umana et al. |
| 9,296,820 | B2 | 3/2016 | Umaña et al. |
| 10,561,737 | B2 | 2/2020 | Brinkmann et al. |
| 10,806,795 | B2 | 10/2020 | Brinkmann et al. |
| 11,149,091 | B2 | 10/2021 | Jordan et al. |
| 2001/0018041 | A1 | 8/2001 | Hanna et al. |
| 2002/0006404 | A1 | 1/2002 | Hanna et al. |
| 2002/0009444 | A1 | 1/2002 | Grillo-lopez |
| 2002/0012665 | A1 | 1/2002 | Hanna |
| 2002/0028178 | A1 | 3/2002 | Hanna et al. |
| 2002/0032317 | A1 | 3/2002 | Blank |
| 2002/0039557 | A1 | 4/2002 | White |
| 2002/0058029 | A1 | 5/2002 | Hanna |
| 2002/0128448 | A1 | 9/2002 | Reff |
| 2002/0159996 | A1 | 10/2002 | Hariharan et al. |
| 2002/0164328 | A1 | 11/2002 | Shinkawa |
| 2002/0197256 | A1 | 12/2002 | Grewal |
| 2003/0003097 | A1 | 1/2003 | Reff et al. |
| 2003/0026804 | A1 | 2/2003 | Grillo-lopez |
| 2003/0103971 | A1 | 6/2003 | Hariharan et al. |
| 2003/0115614 | A1 | 6/2003 | Kanda |
| 2003/0129185 | A1 | 7/2003 | Ono et al. |
| 2003/0157108 | A1 | 8/2003 | Presta |
| 2003/0161832 | A1 | 8/2003 | Bander |
| 2003/0180290 | A1 | 9/2003 | Hariharan et al. |
| 2003/0180292 | A1 | 9/2003 | Hanna et al. |
| 2003/0206903 | A1 | 11/2003 | Grillo-lopez |
| 2003/0211107 | A1 | 11/2003 | Hariharan et al. |
| 2004/0072290 | A1 | 4/2004 | Umana et al. |
| 2004/0093621 | A1 | 5/2004 | Shitara |
| 2004/0109865 | A1 | 6/2004 | Niwa |
| 2004/0110282 | A1 | 6/2004 | Kanda |
| 2004/0110704 | A1 | 6/2004 | Yamane |
| 2004/0132140 | A1 | 7/2004 | Satoh |
| 2004/0191256 | A1 | 9/2004 | Raju |
| 2004/0202655 | A1 | 10/2004 | Morton et al. |
| 2004/0202658 | A1 | 10/2004 | Benyunes |
| 2004/0213784 | A1 | 10/2004 | Grillo-lopez et al. |
| 2004/0229310 | A1 | 11/2004 | Simmons |
| 2005/0014934 | A1 | 1/2005 | Hinton |
| 2005/0031613 | A1 | 2/2005 | Nakamura |
| 2005/0032130 | A1 | 2/2005 | Beresini et al. |
| 2005/0042664 | A1 | 2/2005 | Wu et al. |
| 2005/0053602 | A1 | 3/2005 | Brunetta |
| 2005/0058649 | A1 | 3/2005 | Landes et al. |
| 2005/0074843 | A1 | 4/2005 | Umana et al. |
| 2005/0079574 | A1 | 4/2005 | Bond |
| 2005/0079605 | A1 | 4/2005 | Umana |
| 2005/0095243 | A1 | 5/2005 | Chan et al. |
| 2005/0112060 | A1 | 5/2005 | White |
| 2005/0119455 | A1 | 6/2005 | Fuh |
| 2005/0123540 | A1 | 6/2005 | Hanna et al. |
| 2005/0123546 | A1 | 6/2005 | Umana |
| 2005/0158316 | A1 | 7/2005 | Lam et al. |
| 2005/0163775 | A1 | 7/2005 | Chan et al. |
| 2005/0180975 | A1 | 8/2005 | Hanna |
| 2005/0186206 | A1 | 8/2005 | Brunetta |
| 2005/0191297 | A1 | 9/2005 | Brunetta |
| 2005/0255527 | A1 | 11/2005 | Yang et al. |
| 2005/0260186 | A1 | 11/2005 | Bookbinder |
| 2005/0266000 | A1 | 12/2005 | Bond |
| 2005/0271658 | A1 | 12/2005 | Brunetta et al. |
| 2005/0272128 | A1 | 12/2005 | Umana et al. |
| 2005/0276803 | A1 | 12/2005 | Chan et al. |
| 2005/0276805 | A1 | 12/2005 | Hanai |
| 2006/0002930 | A1 | 1/2006 | Brunetta et al. |
| 2006/0024295 | A1 * | 2/2006 | Brunetta .......... A61K 39/39558 424/131.1 |
| 2006/0024300 | A1 | 2/2006 | Adams |
| 2006/0025576 | A1 | 2/2006 | Miller |
| 2006/0034835 | A1 | 2/2006 | Adams et al. |
| 2006/0051345 | A1 | 3/2006 | Frohna |
| 2006/0057149 | A1 | 3/2006 | Johnson et al. |
| 2006/0062787 | A1 | 3/2006 | Hitraya |
| 2006/0067930 | A1 | 3/2006 | Adams |
| 2006/0073148 | A1 | 4/2006 | Tchistiakova et al. |
| 2006/0099662 | A1 | 5/2006 | Chuntharapai et al. |
| 2006/0104968 | A1 | 5/2006 | Bookbinder |
| 2006/0110387 | A1 | 5/2006 | Brunetta |
| 2006/0121028 | A1 | 6/2006 | Reff |
| 2006/0134111 | A1 | 6/2006 | Agarwal |

(56) References Cited

U.S. PATENT DOCUMENTS

2006/0135430 A1 6/2006 Chan et al.
2006/0171950 A1 8/2006 Hariharan et al.
2006/0172385 A1 8/2006 Ernst et al.
2006/0179501 A1 8/2006 Chan et al.
2006/0182739 A1 8/2006 Basey et al.
2006/0188495 A1 8/2006 Barron et al.
2006/0218655 A1 9/2006 Chan et al.
2006/0233797 A1 10/2006 Gujrathi
2006/0240007 A1 10/2006 Sanders
2006/0246004 A1 11/2006 Adams
2006/0263349 A1 11/2006 Mccutcheon et al.
2006/0263355 A1 11/2006 Quan et al.
2006/0275284 A1 12/2006 Hanna
2006/0286100 A1 12/2006 Hariharan et al.
2006/0286101 A1 12/2006 Hariharan et al.
2007/0003544 A1 1/2007 Hanna
2007/0009518 A1 1/2007 Novobrantseva et al.
2007/0009519 A1 1/2007 Hariharan et al.
2007/0020260 A1 1/2007 Presta
2007/0025987 A1 2/2007 Brunetta
2007/0031331 A1 2/2007 Brunetta et al.
2007/0061900 A1 3/2007 Murphy
2007/0071745 A1 3/2007 Umana et al.
2007/0117126 A1 5/2007 Sidhu
2007/0134759 A1 6/2007 Nishiya
2007/0160598 A1 7/2007 Dennis
2007/0212733 A1 9/2007 Martin
2007/0231324 A1 10/2007 Ashkenazi
2007/0237764 A1 10/2007 Birtalan
2007/0292936 A1 12/2007 Barthelemy
2008/0008719 A1 1/2008 Bowdish et al.
2008/0038261 A1 2/2008 Grillo-lopez
2008/0044421 A1 2/2008 Ashkenazi
2008/0069820 A1 3/2008 Fuh
2008/0075719 A1 3/2008 Chan et al.
2008/0095771 A1 4/2008 Barron et al.
2008/0176257 A9 7/2008 Chuntharapai et al.
2008/0213280 A1 9/2008 Benyunes
2008/0241884 A1 10/2008 Shitara
2008/0280322 A9 11/2008 Umana et al.
2009/0002360 A1 1/2009 Chen
2009/0004189 A1 1/2009 Behrens et al.
2009/0010921 A1 1/2009 Umana et al.
2009/0053786 A1 2/2009 Kao
2009/0060913 A1 3/2009 Friess et al.
2009/0098118 A1 4/2009 Friess et al.
2009/0110688 A1 4/2009 Fertig et al.
2009/0148435 A1 6/2009 Lebreton
2009/0155257 A1 6/2009 Adams et al.
2009/0162352 A1 6/2009 Adler
2009/0169550 A1 7/2009 Dummer
2009/0175854 A1 7/2009 Ashkenazi
2009/0214561 A1 8/2009 Close
2009/0238762 A1 * 9/2009 Totoritis .................. A61P 17/06
424/9.2
2009/0246197 A1 10/2009 Dumontet et al.
2009/0269339 A1 10/2009 Kelman et al.
2009/0304690 A1 12/2009 Umana et al.
2009/0311255 A1 12/2009 Brunetta et al.
2009/0317384 A1 12/2009 Ashkenazi
2010/0092997 A1 4/2010 Nakamura et al.
2010/0158903 A1 6/2010 Smith et al.
2010/0247484 A1 9/2010 Barchet et al.
2010/0255013 A1 10/2010 Presta
2010/0291549 A1 11/2010 Ramakrishnan
2010/0310581 A1 12/2010 Dumontet et al.
2011/0008250 A1 1/2011 Curd et al.
2011/0008337 A1 1/2011 Curd et al.
2011/0008338 A1 1/2011 Curd et al.
2011/0052488 A1 3/2011 Dennis, Jr. et al.
2011/0076273 A1 3/2011 Adler et al.
2011/0086050 A1 4/2011 Presta
2011/0165151 A1 7/2011 Herting et al.
2011/0165152 A1 7/2011 Dreyling et al.
2011/0177067 A1 7/2011 Dumontet et al.
2011/0243931 A1 10/2011 Friess et al.
2012/0251531 A1 10/2012 Baehner
2012/0251534 A1 10/2012 Grillo-lopez
2013/0040831 A1 2/2013 Liu et al.
2014/0248262 A1 9/2014 Sampath
2015/0158846 A1 6/2015 Crawford et al.
2016/0075793 A1 3/2016 Umaña et al.
2016/0075794 A1 3/2016 Umaña et al.
2016/0076009 A1 3/2016 Umaña et al.
2016/0324984 A1 11/2016 Brinkmann et al.
2016/0346387 A1 12/2016 Brunetta
2017/0029520 A1 2/2017 Brunetta et al.
2019/0365888 A1 12/2019 Brunetta
2020/0002437 A1 1/2020 Brinkmann et al.
2022/0259321 A1 8/2022 Cascino
2023/0039927 A1 2/2023 Cascino
2024/0033351 A1 2/2024 Brunetta
2024/0043554 A1 2/2024 Maller
2024/0409657 A1 12/2024 Cascino

FOREIGN PATENT DOCUMENTS

CN 103282054 A 9/2013
EA 201000091 A1 6/2010
EA 018708 B1 10/2013
EP 0340109 A2 11/1989
EP 0404097 A2 12/1990
EP 0669836 B1 7/1996
EP 0425235 B1 9/1996
EP 0752248 B1 9/2000
EP 0999853 B1 1/2003
EP 1870459 A1 12/2007
EP 1005870 B1 1/2009
EP 2000149 B1 5/2009
EP 1131096 B1 1/2010
EP 2197918 A1 6/2010
EP 1798240 B1 4/2011
EP 2319529 A1 5/2011
EP 2691417 A1 2/2014
EP 2234600 B1 8/2014
JP 2008501706 A 1/2008
JP 2009505650 A 2/2009
JP 2010538024 A 12/2010
JP 2017522295 A 8/2017
RU 2396084 C1 8/2010
RU 2509558 C2 3/2014
WO 198804936 A1 7/1988
WO 199008187 A1 7/1990
WO 199011294 A1 10/1990
WO 199101333 A1 2/1991
WO 199110741 A1 7/1991
WO 199301161 A1 1/1993
WO 199308829 A1 5/1993
WO 199316185 A2 8/1993
WO 199316185 A3 9/1993
WO 199411026 A2 5/1994
WO 199411026 A3 8/1994
WO 199429351 A2 12/1994
WO 199429351 A3 2/1995
WO 199627011 A1 9/1996
WO 199633735 A1 10/1996
WO 199634096 A1 10/1996
WO 199717446 A2 5/1997
WO 199730087 A1 8/1997
WO 199717446 A3 9/1997
WO 199823645 A1 6/1998
WO 199824893 A2 6/1998
WO 199824893 A3 8/1998
WO 1998050431 A2 11/1998
WO 199856418 A1 12/1998
WO 199858964 A1 12/1998
WO 1998050431 A3 1/1999
WO 199922764 A1 5/1999
WO 199951642 A1 10/1999
WO 199954342 A1 10/1999
WO 199957134 A1 11/1999
WO 200009160 A1 2/2000
WO 200027428 A1 5/2000
WO 200027433 A1 5/2000

(56) References Cited

FOREIGN PATENT DOCUMENTS

| | | | |
|---|---|---|---|
| WO | 200050088 | A2 | 8/2000 |
| WO | 200061739 | A1 | 10/2000 |
| WO | 200067796 | A1 | 11/2000 |
| WO | 200050088 | A3 | 12/2000 |
| WO | 200103734 | A1 | 1/2001 |
| WO | 200110460 | A1 | 2/2001 |
| WO | 2001029246 | A1 | 4/2001 |
| WO | 200134194 | A1 | 5/2001 |
| WO | 200134651 | A1 | 5/2001 |
| WO | 200174388 | A1 | 10/2001 |
| WO | 200180884 | A1 | 11/2001 |
| WO | 200197858 | A2 | 12/2001 |
| WO | 200204021 | A1 | 1/2002 |
| WO | 200222212 | A2 | 3/2002 |
| WO | 200231140 | A1 | 4/2002 |
| WO | 200234790 | A1 | 5/2002 |
| WO | 200197858 | A3 | 8/2002 |
| WO | 2002078766 | A2 | 10/2002 |
| WO | 200222212 | A3 | 2/2003 |
| WO | 2003011878 | A2 | 2/2003 |
| WO | 2003024388 | A2 | 3/2003 |
| WO | 2002078766 | A3 | 5/2003 |
| WO | 2003035835 | A2 | 5/2003 |
| WO | 2003024388 | A3 | 7/2003 |
| WO | 2003035835 | A3 | 10/2003 |
| WO | 2003084570 | A1 | 10/2003 |
| WO | 2003085107 | A1 | 10/2003 |
| WO | 2003085119 | A1 | 10/2003 |
| WO | 2003011878 | A3 | 11/2003 |
| WO | 2004035607 | A2 | 4/2004 |
| WO | 2004042072 | A2 | 5/2004 |
| WO | 2004056312 | A2 | 7/2004 |
| WO | 2004060052 | A2 | 7/2004 |
| WO | 2004060053 | A2 | 7/2004 |
| WO | 2004035607 | A3 | 8/2004 |
| WO | 2004065540 | A2 | 8/2004 |
| WO | 2004065569 | A2 | 8/2004 |
| WO | 2004060052 | A3 | 9/2004 |
| WO | 2004091657 | A2 | 10/2004 |
| WO | 2004092219 | A2 | 10/2004 |
| WO | 2004042072 | A3 | 12/2004 |
| WO | 2004060053 | A3 | 1/2005 |
| WO | 2005000351 | A2 | 1/2005 |
| WO | 2005005462 | A2 | 1/2005 |
| WO | 2004091657 | A3 | 2/2005 |
| WO | 2004092219 | A3 | 2/2005 |
| WO | 2005017529 | A1 | 2/2005 |
| WO | 2004065540 | A3 | 3/2005 |
| WO | 2004065569 | A3 | 3/2005 |
| WO | 2005023302 | A2 | 3/2005 |
| WO | 2005023302 | A3 | 4/2005 |
| WO | 2005035586 | A1 | 4/2005 |
| WO | 2005035778 | A1 | 4/2005 |
| WO | 2004056312 | A3 | 5/2005 |
| WO | 2005044859 | A2 | 5/2005 |
| WO | 2005053742 | A1 | 6/2005 |
| WO | 2005060999 | A2 | 7/2005 |
| WO | 2005061542 | A2 | 7/2005 |
| WO | 2005062955 | A2 | 7/2005 |
| WO | 2005044859 | A3 | 8/2005 |
| WO | 2005079479 | A2 | 9/2005 |
| WO | 2005100402 | A1 | 10/2005 |
| WO | 2005103081 | A2 | 11/2005 |
| WO | 2005108989 | A2 | 11/2005 |
| WO | 2005061542 | A3 | 12/2005 |
| WO | 2005103081 | A3 | 12/2005 |
| WO | 2005113003 | A2 | 12/2005 |
| WO | 2005114218 | A2 | 12/2005 |
| WO | 2005115453 | A2 | 12/2005 |
| WO | 2005117972 | A2 | 12/2005 |
| WO | 2005117978 | A2 | 12/2005 |
| WO | 2005120437 | A2 | 12/2005 |
| WO | 2005005462 | A3 | 1/2006 |
| WO | 2005060999 | A3 | 1/2006 |
| WO | 2005079479 | A3 | 1/2006 |
| WO | 2005114218 | A3 | 2/2006 |
| WO | 2006012508 | A2 | 2/2006 |
| WO | 2005000351 | A3 | 3/2006 |
| WO | 2005113003 | A3 | 3/2006 |
| WO | 2005115453 | A3 | 3/2006 |
| WO | 2006029224 | A2 | 3/2006 |
| WO | 2006029275 | A2 | 3/2006 |
| WO | 2006029879 | A2 | 3/2006 |
| WO | 2006031370 | A2 | 3/2006 |
| WO | 2006034488 | A2 | 3/2006 |
| WO | 2005117972 | A3 | 4/2006 |
| WO | 2006041680 | A2 | 4/2006 |
| WO | 2006044908 | A2 | 4/2006 |
| WO | 2005062955 | A3 | 6/2006 |
| WO | 2005108989 | A3 | 6/2006 |
| WO | 2005117978 | A3 | 6/2006 |
| WO | 2005120437 | A3 | 6/2006 |
| WO | 2006012508 | A3 | 6/2006 |
| WO | 2006066086 | A1 | 6/2006 |
| WO | 2006066089 | A1 | 6/2006 |
| WO | 2006068867 | A1 | 6/2006 |
| WO | 2006069403 | A2 | 6/2006 |
| WO | 2006029275 | A3 | 7/2006 |
| WO | 2006076651 | A2 | 7/2006 |
| WO | 2006044908 | A3 | 8/2006 |
| WO | 2006084264 | A2 | 8/2006 |
| WO | 2006029224 | A3 | 9/2006 |
| WO | 2006029879 | A3 | 9/2006 |
| WO | 2006034488 | A3 | 9/2006 |
| WO | 2006069403 | A3 | 9/2006 |
| WO | 2006093923 | A2 | 9/2006 |
| WO | 2006113308 | A1 | 10/2006 |
| WO | 2006031370 | A3 | 11/2006 |
| WO | 2006076651 | A3 | 11/2006 |
| WO | 2006116369 | A2 | 11/2006 |
| WO | 2006125140 | A2 | 11/2006 |
| WO | 2006127517 | A2 | 11/2006 |
| WO | 2006133148 | A2 | 12/2006 |
| WO | 2006125140 | A3 | 1/2007 |
| WO | 2006127517 | A3 | 2/2007 |
| WO | 2007031875 | A2 | 3/2007 |
| WO | 2006093923 | A3 | 4/2007 |
| WO | 2006133148 | A3 | 5/2007 |
| WO | 2007059188 | A1 | 5/2007 |
| WO | 2007062090 | A2 | 5/2007 |
| WO | 2007064911 | A1 | 6/2007 |
| WO | 2006084264 | A3 | 7/2007 |
| WO | 2007081768 | A2 | 7/2007 |
| WO | 2006041680 | A3 | 8/2007 |
| WO | 2006116369 | A3 | 8/2007 |
| WO | 2007110205 | A2 | 10/2007 |
| WO | 2007140371 | A2 | 12/2007 |
| WO | 2007147901 | A1 | 12/2007 |
| WO | 2008002064 | A1 | 1/2008 |
| WO | 2007031875 | A3 | 2/2008 |
| WO | 2007110205 | A3 | 2/2008 |
| WO | 2007140371 | A3 | 2/2008 |
| WO | 2007081768 | A3 | 4/2008 |
| WO | 2008077546 | A1 | 7/2008 |
| WO | 2008122007 | A1 | 10/2008 |
| WO | 2007062090 | A3 | 12/2008 |
| WO | 2008157282 | A1 | 12/2008 |
| WO | 2009007750 | A1 | 1/2009 |
| WO | 2009009523 | A2 | 1/2009 |
| WO | 2009030368 | A1 | 3/2009 |
| WO | 2009040268 | A1 | 4/2009 |
| WO | 2009049841 | A1 | 4/2009 |
| WO | 2009053038 | A2 | 4/2009 |
| WO | 2009009523 | A3 | 5/2009 |
| WO | 2009058812 | A1 | 5/2009 |
| WO | 2009062080 | A1 | 5/2009 |
| WO | 2009053038 | A3 | 6/2009 |
| WO | 2009080251 | A1 | 7/2009 |
| WO | 2009080252 | A1 | 7/2009 |
| WO | 2009080253 | A1 | 7/2009 |
| WO | 2009080254 | A1 | 7/2009 |
| WO | 2009080541 | A1 | 7/2009 |
| WO | 2009085765 | A1 | 7/2009 |
| WO | 2009086072 | A2 | 7/2009 |

(56) References Cited

FOREIGN PATENT DOCUMENTS

| | | | |
|---|---|---|---|
| WO | 2009089004 | A1 | 7/2009 |
| WO | 2009092011 | A1 | 7/2009 |
| WO | 2009118142 | A1 | 10/2009 |
| WO | 2009118324 | A1 | 10/2009 |
| WO | 2009086072 | A3 | 11/2009 |
| WO | 2009134738 | A1 | 11/2009 |
| WO | 2010033587 | A2 | 3/2010 |
| WO | 2010056893 | A1 | 5/2010 |
| WO | 2010057107 | A1 | 5/2010 |
| WO | 2010057109 | A1 | 5/2010 |
| WO | 2010033587 | A3 | 9/2010 |
| WO | 2010112193 | A1 | 10/2010 |
| WO | 2010115554 | A1 | 10/2010 |
| WO | 2010115589 | A1 | 10/2010 |
| WO | 2010129304 | A2 | 11/2010 |
| WO | 2010136172 | A1 | 12/2010 |
| WO | 2010145792 | A1 | 12/2010 |
| WO | 2010145793 | A1 | 12/2010 |
| WO | 2011003557 | A1 | 1/2011 |
| WO | 2011003780 | A1 | 1/2011 |
| WO | 2010129304 | A3 | 2/2011 |
| WO | 2011090754 | A1 | 7/2011 |
| WO | 2011090762 | A1 | 7/2011 |
| WO | 2011131749 | A1 | 10/2011 |
| WO | 2011143545 | A1 | 11/2011 |
| WO | 2011003557 | A8 | 1/2012 |
| WO | 2012011875 | A1 | 1/2012 |
| WO | 2012018771 | A1 | 2/2012 |
| WO | 2012022747 | A1 | 2/2012 |
| WO | 2012058768 | A1 | 5/2012 |
| WO | 2012093068 | A1 | 7/2012 |
| WO | 2012130831 | A1 | 10/2012 |
| WO | 2013090478 | A1 | 6/2013 |
| WO | 2013096291 | A2 | 6/2013 |
| WO | 2013096291 | A3 | 9/2013 |
| WO | 2013157953 | A1 | 10/2013 |
| WO | 2013157954 | A1 | 10/2013 |
| WO | 2013177062 | A2 | 11/2013 |
| WO | 2014006124 | A1 | 1/2014 |
| WO | 2013177062 | A3 | 2/2014 |
| WO | 2014039855 | A1 | 3/2014 |
| WO | 2014177617 | A1 | 11/2014 |
| WO | 2015101586 | A1 | 7/2015 |
| WO | 2015197736 | A1 | 12/2015 |
| WO | 2016183104 | A1 | 11/2016 |
| WO | 2017004091 | A1 | 1/2017 |
| WO | 2017149018 | A1 | 9/2017 |
| WO | 2018100096 | A1 | 6/2018 |
| WO | 2021050645 | A1 | 3/2021 |
| WO | 2022198192 | A1 | 9/2022 |
| WO | 2024102734 | A1 | 5/2024 |

OTHER PUBLICATIONS

Bai et al. (Clin Pharmacokinet 2012; 51:119-135) (Year: 2012).*

Abdel-Hafez, M.A. et al. (2017, e-pub. Feb. 2, 2017). "Predictive Risk Factors of Steroid Dependent Nephrotic Syndrome in Children," J. Nephropathol 6(3): 18••186.

Aigner, A. (2008). "Cellular Delivery In Vivo of Sirna-Based Therapeutics," Curr. Pharm. Des. 14(34):3603-3619.

Akinc, A. et al. (Jul. 2010, e-pub. May 11, 2010). "Targeted Delivery of RNAi Therapeutics With Endogenous and Exogenous Ligand-Based Mechanisms," Mol. Ther. 18(7):1357-1364.

Akinc, A. et al. (May 11, 2010). "Development of Lipidoid-siRNA Formulations for Systemic Delivery to the Liver," Mol. Ther. 17(5):872-879.

Aktas, E. et al. (2009, e-pub. Oct. 5, 2008). "Relationship Between CD107a Expression and Cytotoxic Activity," Cell Immunol. 254(2):149-154.

Aletaha, D. et al. (Sep. 2010). "2010 Rheumatoid Arthritis Classification Criteria: an American College of Rheumatology/European League Against Rheumatism Collaborative Initiative," Ann Rheum Dis., 69(9):1580-1588.

Almaani, S. et al. (Jan. 2019, e-pub. Aug. 27, 2018). "B-Cell Therapy in Lupus Nephritis: An Overview," Nephrol. Dial. Transplant 34(1):22-29.

Almagro, J.C. et al. (Jan. 1, 2008). "Humanization of Antibodies," Front. Biosci. 13:1619-1633.

Alter, G. et al. (Nov. 2004, e-pub. Sep. 25, 1994). "CD107a as a Functional Marker for the Identification of Natural Killer Cell Activity," J Immunol Methods. 294(1-2):15-22.

Aringer, M. et al. (2008, e-pub. Jan. 23, 2008). "The Role of Tumor Necrosis Factor—Alpha in Systemic Lupus Erythematosus," Arthritis Research & Therapy 10:1-8.

Asherson, R.A. et al. (Nov. 1989). "The "Primary" Antiphospholipid Syndrome: Major Clinical and Serological Features", Medicine, 68(6):366-374.

Atwell, S. et al. (1997). "Stable Heterodimers From Remodeling the Domain Interface of a Homodimer Using a Phage Display Library," J. Mol. Biol. 270 (1):26-35.

Ausubel, F.M. et al. (1995). Short Protocols in Molecular Biology, Greene Publishing and Wiley Interscience, New York, New York, (Table of Contents), 22 pages.

Avantgen, Inc. (Jul. 27, 2009). "AvantGen's Antibody Humanization and Discovery Technologies—GermlinerTM Antibodies: An Effective and Proprietary Technology for Humanizing Antibodies Based on Epitope-Guided Selection," 4 pages.

Baca, M. et al. (Apr. 18, 1997). "Antibody Humanization Using Monovalent Phage Display," J. Biol. Chem. 272(16):10678-10684.

Bagci, H. et al. (May 1993). "Monoclonal Anti-biotin Antibodies Simulate Avidin in the Recognition of Biotin," FEBS 322(1):47-50.

Bai, S. et al. (2012). "A Guide to Rational Dosing of Monoclonal Antibodies," Clin. Pharmacokinet 51(2):119-135.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 91:3809-3813.

Baselga, J. (Sep. 2001). "The EGFR as a Target for Anticancer Therapy—Focus on Cetuximab," Eur. J. Cancer 37(Suppl. 4):S16-S22.

Beck, A. et al. (May 2010). "Strategies and Challenges for the Next Generation of Therapeutic Antibodies," Nat. Rev. Immunol. 10(5):345-352.

Becker, Y. et al. (Aug. 1, 2006). "The Emerging Role of Rituximab in Organ Transplantation," Transplant International 19(8):621-628.

Beers, S.A. et al. (Nov. 15, 2008, e-pub. Jun. 26, 2008). "Type II (tositumomab) Anti-CD20 Monoclonal Antibody Out Performs Type I (Rituximab-Like) Reagents in B-Cell Depletion Regardless of Complement Activation," Blood 15:112(10):4170-4177.

Benz, K. et al. (Jul. 2004, e-pub. Apr. 8, 2004). "Change of the Course of Steroid-Dependent Nephrotic Syndrome After Rituximab Therapy," Pediatr Nephrol 19(7):794-797.

Bera, T.K. et al. (Nov.-Dec. 1998; e-published on Oct. 20, 2008). "Comparison of Recombinant Immunotoxins Against LeY Antigen Expressing Tumor Cells: Influence of Affinity, Size, and Stability," Bioconjugate Chemistry 9(6):736-743.

Berger, M. (1975). "Production of Antibodies that Bind Biotin and Inhibit Biotin Containing Enzymes," Biochemistry 14(11):2338-2342.

Bhattarai, S.R. et al. (Dec. 2010, e-pub. Aug. 21, 2010). "Enhanced Gene and siRNA Delivery by Polycation-Modified Mesoporous Silica Nanoparticles Loaded With Chloroquine," Pharm. Res. 27(12):2556-2568, 26 pages.

Bichile, T. et al. (2014, e-pub. May 20, 2014). "Prevention and Management of Co-Morbidities in SLE," Presse Med. 43:e187-e195.

Boerner, P. et al. (Jul. 1, 1991). "Production of Antigen-Specific Human Monoclonal Antibodies From in Vitro-Primed Human Splenocytes," J. Immunol. 147(1):86-95.

Bologna, L. et al. (2011). "Mechanism of Action of Type II, Glycoengineered, Anti-CD20 Monoclonal Antibody GA101 in B-Chronic Lymphocytic Leukemia Whole Blood Assays in Comparison with Rituximab and Alemtuzumab," J. Immunol. 186(6):3762-3769.

(56) References Cited

OTHER PUBLICATIONS

Boune, S. et al. (2020). "Principles of N-Linked Glycosylation Variations of IgG-Based Therapeutics: Pharmacokinetic and Functional Considerations," Antibodies 9(22):1-20.
Bowles J.A. et al. (Oct. 15, 2006, e-pub. Jul. 6, 2006). "Anti-CD20 Monoclonal Antibody with Enhanced Affinity for CD16 Activates NK Cells at Lower Concentrations and More Effectively than Rituximab," Blood, 108(8):2648-2654.
Brennan, M. et al. (Jul. 5, 1985). "Preparation of Bispecific Antibodies by Chemical Recombination of Monoclonal Immunoglobulin G1 Fragments," Science 229:81-83.
Brinkmann, U. et al. (Oct. 1, 1991). "B3(Fv)-PE38KDEL, a Single-Chain Immunotoxin That Causes Complete Regression of a Human Carcinoma in Mice," Proc. Natl. Acad. Sci. USA 88(19):8616-8620.
Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.
Brüggemann, M. et al. (1993). "Designer Mice: The Production of Human Antibody Repertoires in Transgenic Animals," Year in Immunol. 7:33-40.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Burris, T.P. et al. (Mar. 1999). "A Novel Method for Analysis of Nuclear Receptor Function at Natural Promoters: Peroxisome Proliferator-Activated Receptor γ Agonist Actions on aP2 Gene Expression Detected Using Branched DNA Messenger RNA Quantitation," Mol. Endocrinol. 13(3):410-417.
Cameron, J.S. (1999). "Lupus Nephritis," J. Am. Soc. Nephrol. 10:413-424.
Cao, Y. et al. (1998). "Development of a Bispecific Monoclonal Antibody as a Universal Immunoprobe for Detecting Biotinylated Macromolecules," Journal of Immunological Methods 220:85-91.
Capel, P.J.A. et al. (Feb. 1994). "Heterogeneity of Human IgG Fc Receptors," Immunomethods 4(1):25-34.
Carter, P. et al. (May 1992). "Humanization of an Anti-p185HER2 Antibody for Human Cancer Therapy," Proc. Natl. Acad. Sci. USA 89:4285-4289.
Cartron, G. et al. (2016, e-pub. Nov. 12, 2015). "Rationale for Optimal Obinutuzumab/GA101 Dosing Regimen in B-Cell Non-Hodgkin Lymphoma," Haematologica 101(2):226-234.
Cartron, G. et al. (Aug. 3, 2017). Obinutuzumab: What is There to Learn From Clinical Trials?, Blood 130(5):581-589.
Chan, D.P. et al. (Nov. 2013, e-pub. Aug. 7, 2013). "Click Conjugated Polymeric Immuno-Nanoparticles for Targeted siRNA and Antisense Oligonucleotide Delivery," Biomaterials 34(33):8408-8415.
Chanchlani, R. et al. (Apr. 19, 2016). "Ethnic Differences in Childhood Nephrotic Syndrome," Front Pediatr. 4:39, 6 pages.
Chari, R.V.J. et al. (Jan. 1, 1992). "Immunoconjugates Containing Novel Maytansinoids: Promising Anticancer Drugs," Cancer Res. 52:127-131.
Charlton, K.A. (2004). "Expression and Isolation of Recombinant Antibody Fragments in *E. coli*," Methods Mol Biol 248:245-254.
Chen, D.R. et al. (2012). "Living Life Without B Cells is Repeated B-Cell Depletion a Dafe and Effective Long-Term Treatment Plant for Rheumatoid Arthritis?" Int. J. Clin. Rehmatol. Int. J. Clin. Rheum. 7(2):159-166.
Chen, Y. et al. (1999). "Selection and Analysis of an Optimized Anti-VEGF Antibody: Crystal Structure of an Affinity-Matured Fab in Complex With Antigen," J. Mol. Bio. 293:865-881.
Chen, Y.E. et al. (2008). "Value of a Complete or Partial Remission in Severe Lupus Nephrities," Clin. J. Am. Soc. Nephrol. 3:46-53.
Chitnis, M.M. et al. (Oct. 15, 2008). "The Type 1 Insulin-Like Growth Factor Receptor Pathway," Clin. Cancer Res. 14(20):6364-6370.
Chothia, C. et al. (Aug. 20, 1987). "Canonical Structures for the Hypervariable Regions of Immunoglobulins," J. Mol. Biol. 196(4):901-917.
Chowdhury, P.S. (2001). "Targeting Random Mutations to Hotspots in Antibody Variable Domains for Affinity Improvement," Methods in Molecular Biology 178:269-285.
Chowdhury, P.S. (2003). "Engineering Hot Spots for Affinity Enhancement of Antibodies," Methods Mol. Biol. 207:179-196.
Chung, C. H. (2008) "Managing Premedications and the Risk for Reactions to Infusional Monoclonal Antibody Therapy," The Oncologist 13(6):725-732.
Clackson, T. et al. (Aug. 15, 1991). "Making Antibody Fragments Using Phage Display Libraries," Nature 352:624-628.
clinical trials.gov (Jun. 25, 2021). NCT04629248—A Study Evaluating the Efficacy and Safety of Obinutuzumab in Participants with Primary Membranous Nephropathy (Majesty), 19 pages.
clinical trials.gov (Mar. 29, 2023). "NCT05627557—A Study to Evaluate the Efficacy and Safety of Obinutuzumab Versus MMF in Participants with Childhood Onset Idiopathic Nephrotic Syndrome (INShore)," 21 pages.
clinicaltrials.gov (Jan. 8, 2021). NCT04702256—"Inductions Therapy for Lupus Nephritis with no Added Oral Steroids: A Trial Comparing Oral Corticosteroids Plus Mycophenolate Mofetil (MMF) Versus Obinutuzumab and MMF (Obilup)," 13 pages.
clinicaltrials.gov (Jan. 9, 2020). NCT04221477—"A Study to Evaluate the Efficacy and Safety of Obinutuzumab in Patients with ISR/RPS 2003 Class III or IV Lupus Nephritis (Regency)," 10 pages.
clinicaltrials.gov (Sep. 14, 2015). NCT02550625 "A Study to Evaluate the Safety and Efficacy of Obinutuzumab Compared with Placebo in Participants with Lupus Nepritis (LN)," 73 pages.
clinicaltrials.gov (Sep. 15, 2015). NCT02550625 "A Study to Evaluate the Safety and Efficacy of Obinutuzumab Compared with Placebo in Participants with Lupus Nepritis (LN)," (v33), Retrieved online: a href="URL:https" target="_blank" URL:https/a://clinicaltrials.gov/ct2/history/NCT02550652?A=33&B=33&C=merged#StudyPageTop, last visited Jan. 11, 2023, 12 pages.
Clynes, R. et al. (Jan. 1998). "Fc Receptors are Required in Passive and Active Immunity to Melanoma," Proc. Natl. Acad. Sci. U.S.A. 95:652-656.
Cole, S.P.C. et al. (1985). "The EBV-Hybridoma Technique and Its Application to Human Lung Cancer," in Monoclonal Antibodies and Cancer Therapy, Alan R. Liss, p. 77-96.
Coligan, J.E. et al. (1991). Current Protocols in Immunology 3.12-3.12.14.
Collins, M.L. et al. (Aug. 1, 1997). "A Branched DNA Signal Amplification Assay for Quantification of Nucleic Acid Targets Below 100 Molecules/ml," Nucleic Acids Res. 25(15):2979-2984.
Colucci, M. et al. (Jul. 16, 2019). "Prolonged Impairment of Immunological Memory After Anti-CD20 Treatment in Pediatric Idiopathic Nephrotic Syndrome," Front. Immunol 10:1653, 14 pages.
Colucci, M. et al. (Nov. 13, 2015). "B-Cell Reconstitution After Rituximab Treatment in Idiopathic Nephrotic Syndrome," J. Am Soc Nephrol 27(6):1811-1822, 35 pages.
Condon, M.B. et al. (2013). "Prospective Observational Single-Centre Cohort Study to Evaluate the Effectiveness of Treating Lupus Nephrities with Rituzimab and Mycophenolate Mofetil but No Oral Steroids," Ann. Rheum. Dis. 72:1280-1286.
Cragg, M.S. et al. (Apr. 1, 2004, e-pub. Oct. 9, 2003). "Antibody Specificity Controls In Vivo Effector Mechanisms of Anti-CD20 Reagents," Blood 103(7):2738-2743, 7 pages.
Cragg, M.S. et al. (Feb. 1, 2003). "Complement-Mediated Lysis by Anti-CD20 Mab Correlates With Segregation Into Lipid Rafts," Blood 101(3):1045-1052.
Cravedi, P. et al. (2011, e-pub. Apr. 21, 2011). "Efficacy and Safety of Rituximab Second-Line Therapy for Membranous Nephropathy: A Prospective, Matched-Cohort Study." Am. J. Nephrol. 33:461-468.
Cumming, D.A. (Mar. 1991) "Glycosylation of Recombinant Protein Therapeutics: Control and Functional Implications," Glycobiology 1(2):115-130.
Cunningham, B.C. et al. (Jun. 2, 1989). "High-Resolution Epitope Mapping of hGH-Receptor Interactions by Alanine-Scanning Mutagenesis," Science 244:1081-1085.

(56) References Cited

OTHER PUBLICATIONS

Dakshinamurti, K. et al. (1986). "Production and Characterization of a Monoclonal Antibody to Biotin," Biochem. J. 237:477-482.
Dall'Acqua, W.F. et al. (2005). "Antibody Humanization by Framework Shuffling," Methods 36:43-60.
Dall'Era, M. et al. (2018). "Phase 2 Trial of Induction Therapy with Anti-CD20 (Rituximab) Followed by Maintenance Therapy with Anti-BAFF (Belimumab) in Patients with Active Lupus Nephritis," Arthritis Rheumatol. 70(suppl 9):Abst.1870, 3 pages.
Dall'Era, M. et al. (Mar. 2011). "Identification of Biomarkers that Predict Response to Treatment of Lupus Nephritis with Mycophenolate Mofetil or Pulse Cyclophosphamide," Arthritis Care Res. 63(3):351-357.
Daëron, M. (1997). "Fc Receptor Biology," Ann. Rev. Immunol. 15:203-234.
De Haas, M. et al. (1995). "Fcγ Receptor of Phagocytes," J. Lab. Clin. Med. 126(4):330-341.
De Pascalis, R. et al. (2002). "Grafting of 'Abbreviated' Complementarity-Determining Regions Containing Specificity-Determining Residues Essential for Ligand Contact to Engineer a Less Immunogenic Humanized Monoclonal Antibody," J. Immunol. 169(6):3076-3084.
Dossier, C. et al. (2021, e-pub. Mar. 10, 2021). "Response to Majeranowski," Pediatric Nephrology 36(6):1653, 1 page.
Dossier, C. et al. (2021, e-pub. Oct. 28, 2020). "A Global AntiB Cell strategy Combining Obinutuzumab and Daratumumab in Severe Pediatric Nephrotic Syndrome," Pediatric Nephrology 36(5):1175-1182.
Dubowchik, G.M. et al. (2002). "Doxorubicin Immunoconjugates Containing Bivalent, Lysosomally-Cleavable Dipeptide Linkages," Bioorganic & Medicinal Chemistry Letters 12:1529-1532.
Duncan, A.R. et al. (Apr. 21, 1988). "The Binding Site for C1q on IgG," Nature 322:738-740.
Einfeld, D.A. et al. (1988). "Molecular Cloning of the Human B Cell CD20 Receptor Predicts a Hydrophobic Protein with Multiple Transmembrane Domains," EMBO J. 7(3):711-717.
Eisenberg, R. (Apr. 15, 2003). "SLE-Rituimab in Lupus," Arthritis Research & Therapy 5(4):157-159.
El Ouahabi, A et al. (1999). "Intracellular Visualization ofBrdU-labeled Plasmid DNA/Cationic Liposome Complexes," The Journal of Histochemistry & Cytochemistry 47(9):1159-1166.
EMA. (May 22, 2014). "CHMP Assessment Report. Gazyvaro, EMA/CHMP/231450/2014," EMA 123 pages.
Experimental Data D19 in Opposition of 13734999.9 (Apr. 12, 2016). Response to the Communication Pursuant to Article 94(3) EPC, 12 pages.
Experimental Data Showing the KD for the Parental Murine Parental Antibody Filed With Petition of Apr. 12, 2016, 2 pages.
Experimental Report D20 (May 17, 2022). "Experimental Protocol: Determination of the Binding of Murine M33 (muM33) and Humanized Antibody (huM33) Binding Site to Biotinylated Payload," 4 pages.
Extended European Search Report and Search Opinion mailed on May 17, 2022, for European Patent Application No. 21179958.9, filed on May 5, 2016, 21 pages.
Extended European Search Report, dated Apr. 10, 2025, for European Patent Application No. 24191016.5, 19 pages.
FDA (Dec. 2015). "Obinutuzumab (Gazyva)," Natl. Drug Monographs. Retrieved from the internet, https://www.pbm.va.gov/PBM/clinicalguidance/drugmonographs/Obinutuzumab GAZYVA Drug Monograph.pdf, last visited Dec. 16, 2020, 11 pages.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Feng, J,-M. et al. (2010, e-pub. Jan. 1, 2010). "Receptor-Mediated Transport of Drugs Across the BBB," Neuromethods 45:15-34.
Fishwild, D.M. et al. (Jul. 1996). "High-Avidity Human IgGκ Monoclonal Antibodies from a Novel Strain of Minilocus Transgenic Mice," Nature Biotechnol. 14:845-851.
Flatman, S. et al. (2007, e-pub. Dec. 11, 2006). "Process Analytics for Purification of Monoclonal Antibodies," J. Chromatogr. B. 848:79-87.
Focosi, D. et al. (Dec. 13, 2011, e-pub. Sep. 19, 2011). "Immunosuppressive Monoclonal Antibodies: Current and Next Generation," Clinical Microbiology and Infection 17(12):1759-1768.
Freeman, C.L. et al. (2016, e-pub. Apr. 8, 2016). "Role of CD20 Expression and Other Pre-Treatment Risk Factors in the Development of Infusion-Related Reactions in Patients with CLL treated with Obinutuzumab," Leukemia 30:1763-1766.
Freeman, C.L. et al. (Dec. 10, 2015). "Cytokine Release in Patients with CLL Treated with Obinutuzumab and Possible Relationship with Infusion-Related Reactions," Blood 126(24):2646-2649, 8 pages.
Freshney, R.I. (1992). Animal Cell Culture: A Practical Approach, IRL Press, 9 pages.
Fujieda, Y. et al. (Mar. 2013). "Immunocompetent Cell Targeted Therapy," New Medicine Methods 68(862):223-233, 28 pages. (with English Translation).
Furie, R. et al. (Nov. 10, 2019). "A Phase II Randomized, Double-Blind, Placebo-Controlled Study to Evaluate the Efficacy and Safety of Obinutuzumab or Placebo in Combination with Mycophenolate Mofetil in Patients with Active Class III or IV Lupus Nephritis," 2019 ACR/ARP Annual Meeting. Abstract No. 939, 3 pages.
Furie, R.A. et al. (2022, e-pub. Oct. 6, 2021). "B-Cell Depletion with Obinutuzumab for the Treatment of Proliferative Lupus Nephritis: A Randomised, Double-Blind, Placebo-Controlled Trial," Ann. Rheum. Diss. 81:100-107.
Furie, R.A. et al. (Sep. 15, 2009). "Novel Evidence-Based Systemic Lupus Erythematosus Responder Index," Arthritis Rheum. 61(9):1143-1151.
Gazzano-Santoro, H. et al. (1997). "A Non-Radioactive Complement-Dependent Cytotoxicity Assay for Anti-CD20 Monoclonal Antibody," J. Immunol. Methods 202:163-171.
Genentech Press Release (Jun. 10, 2019). "Genentech's Gazyva (Obinutuzumab) Delivers Positive Topline Results for Phase II Lupus Nephritis Study," retrieved from the Internet: https://www.gene.com/media/press-releases/14796/2019-06-10/genentechs-gazyva-obinutuzumab-delivers-, last visited Jun. 10, 2019, 7 pages.
Gerngross, T.U. (Nov. 2004). "Advances in the Production of Human Therapeutic Proteins in Yeasts and Filamentous Fungi," Nature Biotechnology 22(11):1409-1414.
Ghetie, V. et al. (Dec. 1997). "FcRn: the MHC Class I-Related Receptor That Is More Than an IgG Transporter," Immunol. Today 18(12):592-598, 7 pages.
Ghetie, V. et al. (Jul. 1997). "Increasing the Serum Persistence of an IgG Fragment by Random Mutagenesis," Nat Biotech 15:637-640.
Goel, M. et al. (2004). "Plasticity within the Antigen-Combining Site May Manifest as Molecular Mimicry in the Humoral Immune Response," J. Immunol. 173(12):7358-7367.
Golay, J. et al. (Nov. 14, 2013, e-pub. Oct. 8, 2013). "Glycoengineered CD20 Antibody Obinutuzumab Activates Neutrophils and Mediates Phagocytosis Through CD16B More Efficiently Than Rituximab," Blood 122(20):3482-3491.
Gonzales, N.R. et al. (Jan.-Feb. 2005, e-pub. Feb. 28, 2005). "Minimizing the Immunogenicity of Antibodies for Clinical Application," Tumor Biology 26:31-43.
Graham, F.L. et al. (1977). "Characteristics of a Human Cell Line Transformed by DNA from Human Adenovirus Type 5," J. Gen Virol. 36:59-74.
Gratzner, H.G. (Oct. 29, 1982). "Monoclonal Antibody to 5-Bromo-and 5-Iododeoxyuridine: A New Reagent for Detections of DNA Replication," Science 218(4571):474-475.
Greenman J. et al. (1991). "Characterization of a New Monoclonal Anti-FcγRII Antibody, AT10, and its Incorporation Into a Bispecific F(ab')2 Derivative for Recruitment of Cytotoxic Effectors," Mol Immunol. 28(11):1243-1254.
Griffiths, A.D. et al. (1993). "Human Anti-Self Antibodies With High Specificity From Phage Display Libraries," EMBO J. 12(2):725-734.
Grote, M. et al. (2012). "Bispecific Antibody Derivatives Based on Full-Length IgG Formats," Methods Mol. Biol. 901:247-263.

(56) References Cited

OTHER PUBLICATIONS

Gruber, M. et al. (1994). "Efficient Tumor Cell Lysis Mediated by a Bispecific Single Chain Antibody Expressed in *Escherichia coli*," J. Immunol. 152:5368-5374.
Grzywacz, B. et al. (2007). "CD56dimCD16+ NK Cells Downregulate CD16 Following Target Cell Induced Activation of Matrix Metalloproteinases," Leukemia, 21(2):356-359.
Guyer, R.L. et al. (Aug. 1976). "Immunoglobulin Binding by Mouse Intestinal Epithelial Cell Receptors," J. Immunol. 117(2):587-593.
Haas, A.K. et al. (2012). "Chapter 17: Generation of Fluorescent IgG Fusion Proteins in Mammalian Cells," Methods Mol. Biol. 901:265-276.
Hahn, B. et al. (Jun. 2012). "American College of Rheumatology Guidelines for Screening, Treatment, and Management of Lupus Nephritis," Arthritis Care Res. 64(6):797-808.
Hamers-Casterman, C. et al. (Jun. 3, 1993). "Naturally Occurring Antibodies Devoid of Light Chains," Nature 363:446-448.
Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.
Hanes, J. et al. (Nov. 24, 1998). "Ribosome Display Efficiently Selects and Evolves High-Affinity Antibodies in Vitro From Immune Libraries," Proceedings of the National Academy of Sciences 95(24):14130-14135.
Hansen, R.J. et al. (2002). "Intravenous Immunoglobulin Mediates an Increase in Anti-Platelet Antibody Clearance via the FcRn Receptor," Thromb. Haemost. 88:898-899.
Harris, W.J. (1995). "Therapeutic Monoclonal. Production of Humanized Monoclonal Antibodies for In Vivo Imaging and Therapy," Biochem. Soc. Transactions 23:1035-1038.
Hawkins, R.E. et al. (1992). "Selection of Phage Antibodies by Binding Affinity: Mimicking Affinity Maturations," J. Mol. Biol. 226:889-896.
Hellstrom, I. et al. (Mar. 1985). "Strong Antitumor Activities of IgG3 Antibodies to a Human Melanoma-Associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Herter, S. et al. (2013, e-pub. Jul. 19, 2013). "Preclinical Activity of the Type II CD20 Antibody GA101 (Obinutuzumab) Compared With Rituximab and Ofatumumab in Vitro and in Xenograft Models," Molecular Cancer Therapeutics 12(19):2031-2042.
Herters, S. et al. (Aug. 2015). "Abstract 2460: Dissecting the in vitro and in vivo Mechanism of Action of Obinutuzumab (GA101) in Preclinical Models Using an Immune Effector-Dead Version of Obinutuzumab," Cancer Research. 75(15):Supplement:2460, Abstract Only, 4 pages.
Hessell, A.J. et al. (Sep. 6, 2007). "Fc Receptor But Not Complement Binding is Important in Antibody Protection Against HIV," Nature 449(7158):101-105.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.
Hinton, P.R. et al. (Feb. 20, 2004). "Engineered Human IgG Antibodies with Longer Serum Half-lives in Primates," J. Biol. Chem. 279(8):6213-6216.
Hoffmann, E. et al. (Oct. 10, 2013, e-pub. Jun. 22, 2013). "PK Modulation of Haptenylated Peptides via Non-Covalent Antibody Complexation," Journal of Controlled Release 171(1):48-56.
Holliger, P. et al. (Jul. 1993). "Diabodies": Small Bivalent and Bispecific Antibody Fragments, Proc. Natl. Acad. Sci. USA 90:6444-6448.
Holliger, P. et al. (Sep. 2005, e-pub. Sep. 7, 2005). "Engineered Antibody Fragments and the Rise of Single Domains," Nat. Biotechnol. 23(9):1126-1136.
Hongo, J.A.S. et al. (1995). "Development and Characterization of Murine Monoclonal Antibodies to the Latency-Associated Peptide of Transforming Growth Factor β1," Hybridoma 14(3):253-260.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.
Hruskova, Z et al. (2018, e-pub. Jul. 31, 2018). "Lessons Learned from the Failure of Several Recent Trials with Biologic Treatment in Systemic Lupus Erythematosus," Expert Opinion on Biological Therapy 18(9):989-996.
Hudson, P.J. et al. (Jan. 2003). "Engineered Antibodies," Nat. Med. 9(1):129-134.
Hurle, M.R. et al. (1994). "Protein Engineering Techniques for Antibody Humanization," Curr. Op. Biotech. 5:428-433.
Hwang, W.Y.K. et al. (2005). "Use of Human Germline Genes in a CDR Homology-Based Approach to Antibody Humanization," Methods 36: 35-42.
Idusogie, E.E. et al. (2000). "Mapping of the C1q Binding Site on Rituxan, a Chimeric Antibody With a Human IgG1 Fc," J. Immunol. 164:4178-4184.
Iijima, K. et al. (2014, e-pub. Jun. 23, 2014). "Rituximab for Childhood-Onset, Complicated, Frequently Relapsing Nephrotic Syndrome or Steroid-Dependent Nephrotic Syndrome: A Multicentre, Double-Blind, Randomised, Placebo-Controlled Trial," Lancet 384:1273-1281.
International Nonproprietary Names for Pharmaceutical Substances (INN), WHO Drug Information, vol. 22, No. 2, 2008, p. 124, 99 pages.
International Nonproprietary Names for Pharmaceutical Substances (INN), WHO Drug Information, vol. 23, No. 2, 2009, p. 176, 64 pages.
International Nonproprietary Names for Pharmaceutical Substances (INN), WHO Drug Information, vol. 26, No. 4, 2012, p. 453, 71 pages.
International Preliminary Report on Patentability, issued Apr. 29, 2025, for PCT Application No. PCT/US2023/078951, filed Nov. 7, 2023, 10 pages.
International Preliminary Report on Patentability, issued Dec. 27, 2016, for PCT/EP2015/064322, filed Jun. 25, 2015, 7 pages.
International Preliminary Report on Patentability, issued Mar. 15, 2022, for PCT Applicant No. PCT/US2020/050072, filed Sep. 10, 2020, 12 pages.
International Preliminary Report on Patentability, issued on Jan. 2, 2018. for PCT Application No. PCT/US2016/039905, filed on Jun. 28, 2016, 7 pages.
International Preliminary Report on Patentability, issued Sep. 12, 2023, for PCT/US2022/071133, filed Mar. 14, 2022, 12 pages.
International Preliminary Report on Patentability, mailed on Nov. 14, 2017. for PCT Application No. PCT/US2016/031683, filed on May 10, 2016, 10 pages.
International Search Report and Written Opinion, mailed Feb. 23, 2024, for PCT Application No. PCT/US2023/078951, filed Nov. 7, 2023, 14 pages.
International Search Report and Written Opinion, mailed Jan. 27, 2021, for PCT Applicant No. PCT/US2020/050072, filed Sep. 10, 2020, 27 pages.
International Search Report mailed on Sep. 21, 2016, for PCT Application No. PCT/US2016/031683, filed on May 10, 2016, 8 pages.
International Search Report mailed on Sep. 27, 2016, for PCT Application No. PCT/US2016/039905, filed on Jun. 28, 2016, 7 pages.
International Search Report, mailed Aug. 9, 2022, for PCT/US2022/071133, filed Mar. 14, 2022, 24 pages.
International Search Report, mailed Oct. 13, 2015 in PCT Application No. PCT/EP2015/064322, filed Jun. 25, 2015, 5 pages.
Jackson, J.R. et al. (Apr. 1, 1995). "In Vitro Antibody Maturation. Improvement of a High Affinity, Neutralizing Antibody Against IL-1 Beta," J. Immunol. 154(7):3310-3319.
Jadoul, M. et la. (2021). "Kidney Disease: Improving Global Outcomes Glomerular Diseases Work Group. KDIGO 2021 Clinical

(56) References Cited

OTHER PUBLICATIONS

Practice Guideline for the Management of Glomerular Diseases," Kidney Int. 100:S1-S276, 276 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
James, P.A. et al. (2014, e-pub. Dec. 18, 2013). "2014 Evidence-Based Guideline for the Management of High Blood Pressure in Adults Report from the Panel Members Appointed to the Eighth Joint National Committee (JNC 8)," JAMA 311:507-520.
Janeway, C.A. et al. (1994). "Structural Variation in Immunoglobulin Constant Regions," Immunobiology: The Immune System in Health and Disease, Current Biology Ltd./Garland Publishing Inc., 3:29-3:30, 4 pages.
Jefferis, R. et al. (Jun. 1998). "IgG-Fc-Mediated Effector Functions: Molecular Definition of Interaction Sites for Effector Ligands and the Role of Glycosylation," Immunol. Rev. 163:59-76.
Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.
Jenkins, N., et al. (Aug. 1996). "Getting the Glycosylation Right: Implication for the Biotechnology Industry," Nature Biotechnol.. 14:975-981.
Jhaveri, A.M. et al. (Apr. 25, 2014, e-pub. Apr. 25, 2014). "Multifunctional Polymeric Micelles for Delivery of Drugs and siRNA," Front Pharmacol. 5:77, 26 pages.
Johnson, G. et al. (2003). "The Kabat Database and a Bioinformatics Example," Chapter 2 in Methods in Molecular Biology, Lo, B.K.C., ed., Human Press, Totowa, N.J., 248:1-25.
Jones, P.T. et al. (May 29, 1986). "Replacing the Complementarity-Determining Regions in a Human Antibody With Those From a Mouse," Nature 321:522-525.
Jung, S.H. et al. (May 1994). "Design of Interchain Disulfide Bonds in the Framework Region of the Fv Fragment of the Monoclonal Antibody B3," Proteins 19(1):35-47.
Jérôme, V. et al. (2009). "Exhaustive In Vivo Labelling of Plasmid DNA With BrdU for Intracellular Detection in Non-Viral Transfection of Mammalian Cells," Biotechnology Journal 4(10):1479-1487.
Kabat, E.A. (1991). Sequences of Proteins of Immunological Interest, 5th ed., Public Health Service, National Institutes of Health, Bethesda, MD, pp. 647-723.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR Grafting—a New Approach to Antibody Humanization," Methods 36:25-34.
Khan, T. et al. (2014, e-pub. Apr. 30, 2014). "Adjustable Locks and Flexible Keys: Plasticity of Epitope-Paratope Interactions in Germline Antibodies," J. Immunol. 192:5398-5405.
Kies, M.S. et al. (Jul. 2002). "Cetuximab (Imclone/Merck/Bristol-Myers Squibb)," Curr. Opin. Investig. Drugs 3(7):1092-1100.
Kim, J-K. et al. (Apr. 1994). "Localization of the Site of the Murine IgGI Molecule That is Involved in Binding to the Murine Intestinal Fc Receptor," Eur. J. Immunol. 24:2429-2434.
Kindt, T.J. et al. (2007). "Antigens and Antibodies," in Chapter 4 of Kuby Immunology, 6th ed., W.H. Freeman and Co., N.Y, pp. 91, 14 pages.
King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.
Kitsou, K. et al. (Jan. 31, 2022). "The Immunopathogenesis of Idiopathic Nephrotic Syndrome: A Narrative Review of the Literature," European Journal of Pediatrics 181(4):1395-1404.
Klimka, A. et al. (2000). "Human Anti-CD30 Recombinant Antibodies by Guided Phage Antibody Selection Using Cell Panning," Br. J. Cancer 83(2):252-260.
Kohen, F. et al. (1997). "Preparation and Properties of Anti-biotin Antibodies," Methods Enzymology 279:451-463.
Kostelny, S.A. et al. (Mar. 1, 1992). "Formation of a Bispecific Antibody by the Use of Leucine Zippers," J. Immunol. 148(5):1547-1553.
Kozbor, D. et al. (Dec. 1984). "A Human Hybrid Myeloma for Production of Human Monoclonal Antibodies," J. Immunol. 133(6):3001-3005.
Kratz, F. et al. (2006). "Prodrugs of Anthracyclines in Cancer Chemotherapy," Current Medicinal Chemistry 13(5):477-523.
Kunik, V. et al. (Feb. 23, 2012). "Structural Consensus Among Antibodies Defines the Antigen Binding Site," PLOS Computational Biology 8(2):e1002388, 12 pages.
Köhler, G. et al. (Aug. 7, 1975). "Continuous Cultures of Fused Cells Secreting Antibody of Predefined Specificity," Nature 256:495-497.
Leandro, M.J. et al. (Oct. 2002). "An Open Study of B Lymphocyte Depletion in Systemic Lupus Erythematosus," Arthritis Rheum. 46(10): 2673-2677.
Lee, C.V. et al. (2004). "Bivalent Antibody Phage Display Mimics Natural Immunoglobulin," Journal of Immunological Methods 284:119-132.
Lee, C.V. et al. (2004). "High-Affinity Human Antibodies From Phage-Displayed Synthetic Fab Libraries With a Single Framework Scaffold," J. Mol. Biol. 340:1073-1093.
Lee, D.S.W. et al. (Mar. 2021, e-pub. Dec. 15, 2020). "B Cell Depletion Therapies in Autoimmune Disease: Advances and Mechanistic Insights," Nature Reviews 20:179-199.
Lee, S.K. et al. (2012). "Cell-Specific siRNA Delivery by Peptides and Antibodies," Meth. Enzymol. 502:91-122.
Leucuta, S.E. (Apr. 2013). "Systemic and Biophase Bioavailability and Pharmacokinetics of Nanoparticulate Drug Delivery Systems," Curr. Drug. Deliv. 10(2):208-240.
Leus, N.G. et al. (Jan. 1, 2014, e-pub. Nov. 12, 2013). "Effective siRNA Delivery to Inflamed Primary Vascular Endothelial Cells by Anti-E-Selectin and Anti-VCAM-1 PEGylated SAINT-Based Lipoplexes," Int. J. Pharm. 459(1-2):40-50.
Li, H. et al. (Feb. 2006, e-published on Jan. 22, 2006). "Optimization of Humanized IgGs in Glycoengineered Pichia Pastoris," Nature Biotechnology 24(2):210-215.
Li, J. et al. (Mar. 7, 2006). "Human Antibodies for Immunotherapy Development Generated via a Human B Cell Hybridoma Technology," Proc. Natl. Acad. Sci. USA 103(10):3557-3562.
Li, Y. et al. (Jan. 2010). "Drugs for Treatment of Lupus Nephritis as New Target," Nephrology Quick Check, People's Military Medical Publishing House, pp. 57-58, 1 page, (English Translation).
Liboska, R. et al. (Dec. 2012). "Most Anti-BrdU Antibodies React with 2'-Deoxy-5-Ethynyluridine—The Method for the Effective Suppression of This Cross-Reactivity," PLOS One 7(12):e51679, 10 pages.
Lichtnekert, J. et al. (Dec. 2, 2022). "Lupus Nephritis: Current Perspectives and Moving Forward," J. Inflamm. Res. 15:6533-6552.
Lifely, M.R. et al. (Dec. 1995). "Glycosylation and Biological Activity of CAMPATH-1H Expressed in Different Cell Lines and Grown Under Different Culture Conditions," Glycobiology 5(8):813-822.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lonberg, N. (2008, e-pub. Jul. 21, 2008). "Fully Human Antibodies From Transgenic Mouse and Phage Display Platforms," Curr. Opin. Immunol. 20:450-459.
Lonberg, N. (Sep. 2005). "Human Antibodies From Transgenic Animals," Nat. Biotech. 23(9):1117-1125.

(56) References Cited

OTHER PUBLICATIONS

Lonberg, N. et al. (Apr. 28, 1994). "Antigen-Specific Human Antibodies From Mice Comprising Four Distinct Genetic Modifications," Nature 368:856-859.
Lonberg, N. et al. (1995). "Human Antibodies From Transgenic Mice," Intern. Rev. Immunol. 13:65-93.
Léger, O. et al. (Jan. 1, 2011). "Antibody Drug Discovery Chapter 1: Humanization of Antibodies," In Molecular Medicine and Medicinal Chemistry, pp. 1-23.
Maccallum, R.M. et al. (Oct. 1996). "Antibody-Antigen Interactions: Contact Analysis and Binding Site Topography," J. Mol. Biol. 262(5):732-745.
Magaud, J.-P. et al. (1989). "Double Immunocytochemical Labeling of Cell and Tissue Samples With Monoclonal Anti-Bromodeozyuridine," The Journal of Histochemistry and Cytochemistry 37(10):1517-1527.
Malhotra, M. et al. (2013, e-pub. May 21, 2013). "Development and Characterization of Chitosan-PEG-TAT Nanoparticles for the Intracellular Delivery of siRNA.Int," J. Nanomedicine 8:2041-2052.
Manich, G. et al. (Jul. 1, 2013, e-pub. Jun. 7, 2013). "Study of the Transcytosis of an Anti-Transferrin Receptor Antibody With a Fab' Cargo Across the Blood-Brain Barrier in Mice," European Journal of Pharmaceutical Sciences 49(4):556-564.
Mansfield, E. et al. (Sep. 1, 1997). "Recombinant RFB4 Immunotoxins Exhibit Potent Cytotoxic Activity for CD22-Bearing Cells and Tumors," Blood 90(5):2020-2026.
Markowitz, G.S. et al. (2007, e-pub. Jan. 31, 2007). "The ISN/RPS 2003 Classification of Lupus Nephritis; An Assessment at 3 Years," Kidney Int. 71:491-495.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
Mason , A.E. et al. (Jul. 1, 2020, e-pub. Apr. 21, 2020). "Response to First Course of Intensified Immunosuppression in Genetically Stratified Steroid Resistant Nephrotic Syndrome," Clin. J. Am. Soc. Nephrol. 15(7):983-994.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals New York Academy of Sciences pp. 44-68.
Mccafferty, J. et al. (Dec. 6, 1990). "Phage Antibodies: Filamentous Phage Displaying Antibody Variable Domains," Nature 348:552-554.
McNeilage, L.J. et al. (1984). "Autoantibodies Reactive with Small Ribonucleoprotein Antigens: A convergence of Molecular Biology and Clinical Immunology," J. Clin. Lab. Immunol. 15:1-17.
Mendez, L.M.G. et al. (Oct. 13, 2018). "Peripheral Blood B Cell Depletion After Rituximab and Complete Response in Lupus Nephritis," Clin. J. Am. Soc. Nephrol. 13:1502-1509.
Merchant, A.M. et al. (Jul. 1998). "An Efficient Route to Human Bispecific IgG," Nature Biotechnology 16:677-681.
Metz, S. et al. (May 17, 2011). "Bispecific Digoxigenin-binding Antibodies for Targeted Payload Delivery," Proc. Natl. Acad. Sci. USA 108(20):8194-8199.
Miele, E. et al. (2012, e-pub. Jul. 20, 2012). "Nanoparticle-Based Delivery of Small Interfering RNA: Challenges for Cancer Therapy," Int. J. Nanomedicine 7:3637-3657.
Milstein, C. et al. (Oct. 6, 1983). "Hybrid Hybridomas and Their Use in Immunohistochemistry," Nature 305:537-540.
Mitrovic, Z. et al. (Jul. 1, 2007). "FCγRIIIA and FCγRIIA Polymorphisms are not Associated with Response to Rituximab and CHOP in Patients with Diffuse Large B-Cell Lymphoma," The Hematology Journal 92(7):998-999.
Molina, M.A. et al. (Jun. 15, 2011). "Trastuzumab (herceptin), a Humanized Anti-Her2 Receptor Monoclonal Antibody, Inhibits Basal and Activated Her2 Ectodomain Cleavage in Breast Cancer Cells," Cancer Res. 61(12):4744-4749.
Morris, G.E. (1996). "Epitope Mapping Protocols," Methods in Molecular Biology 66:1-12.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Mullis, K.B. et al. (1994). PCR: The Polymerase Chain Reaction, Mullis et al. eds., Birkauswer Press, Boston, 5 pages. TOC.
Mysler, E.F. et al. (Sep. 2013). "Efficacy and Safety of Ocrelizumab in Active Proliferative Lupus Nephritis: Results from a Randomized, Double-Blind, Phase III Study," Arthritis Rheum. 65(9):2368-2379.
Mossner et al. (Jun. 3, 2010). "Increasing the Efficacy of CD20 Antibody Therapy Through the Engineering of a New Type II Anti-CD20 Antibody With Enhanced Direct and Immune Effector Cell-Mediated B-Cell Cytotoxicity," Blood 115(22):4393-4402.
Nagelkerke, S.Q. et al. (2015, e-pub. Jan. 21, 2015). "Immunomodulation by IVlg and the Role of Fc-Gamma Receptors: Classic Mechanisms of Action After All?" Front. Immunol. 5:674, 19 pages.
Nagy, A. et al. (Jan. 18, 2000). "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," Proc. Nat'l. Acad. Sci. 97(2):829-834.
Nattes, E. et al. (Oct. 15, 2018). "Remission of Proteinuria in Multidrug-Resistant Idiopathic Nephrotic Syndrome Following Immunoglobulin Immunoadsorption," Acta Paediatrica 108(4):757-762.
Neshat, M.N. et al. (Mar. 2000). "Mapping the B Cell Superantigen Bidning Site for HIV-1 gp120 on VH3 Ig," International Immunology 12(3):305-312.
Neuberger, M. (Jul. 1996). "Generating High-Avidity Human Mabs in Mice," Nature Biotechnology 14:826.
Neuberger, M.S. (1983). "Expression and Regulation of Immunoglobulin Heavy Chain Gene Transfected into Lymphoid Cells," The EMBO Journal 2(8):1373-1378.
Ng, K.P. et al. (2006). "Repeated B Cell Depletion in Treatment of Refractory Systemic Lupus Erythematosus," Ann. Rheum. Dis. 65:942-945.
Ni, J. (2006). "Research Progress and Future Perspectives in Antibodomics and Antibodomic Drugs," Xiandai Mianyixue 26(4):265-268.(Translation of the Abstract 3 pages.).
Niwa, R. et al. (2015, e-pub. Jan. 12, 2015). "The Current Status and Prospects of Antibody Engineering for Therapeutic Use: Focus on Glycoengineering Technology," Journal of Pharmaceutical Sciences 104(3):930-941.
Noone, D.G. et al. (Jul. 7, 2018). "Idiopathic Nephrotic Syndrome in Children," Lancet 392(10414):61-74.
Offner, H. et al. (Jan. 1991). "T Cell Receptor Peptide Therapy Triggers Autoregulation of Experimental Encephalomyelitis," Science, 251(4992):430-432.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.
Osbourn, J. et al. (2005). "From Rodent Reagents to Human Therapeutics Using Antibody Guided Selection," Methods 36:61-68.
Owen, C.J. et al. (2015). "Obinutuzumab for the Treatment of Patients with Previously Untreated Chronic Lymphocytic Leukemia: Overview and Perspective," Therap. Adv. Hematol. 6(4):161-170.
Pace, C.N. et al. (1995). "How to Measure and Predict the Molar Absorption Coefficient of a Protein," Protein Science 4:2411-2423.
Padlan, E.A. (1991). "A Possible Procedure for Reducing the Immunogenicity of Antibody Variable Domains While Preserving Their Ligand-Binding Properties," Mol. Immunol. 28(4/5):489-498.

(56) References Cited

OTHER PUBLICATIONS

Pai, L.H. et al. (Apr. 15, 1991). "Anti-tumor Activities of Immunotoxins Made of Monoclonal Antibody B3 and Various Forms of Pseudomonas Exotoxin," Proceedings of the National Academy of Sciences, USA 88(8):3358-3362.
Pakula, A.A. et al. (1989). "Genetic Analysis of Protein Stability and Function," Annu. Rev. Genet. 23:289-310.
Pardridge, W.M. (2008, e-pub. Jul. 16, 2008) "Re-engineering Biopharmaceuticals for Delivery to Brain With Molecular Trojan Horses," Bioconjugate Chemistry 19(7):1327-1338.
Pastan, I. et al. (Jul. 15, 1991). "Characterization of Monoclonal Antibodies B1 and B3 That React With Mucinous Adenocarcinomas," Cancer Res. 51(14):3781-3787.
Pendergraft, III, W.F. (No Date). Curriculum Vitae, 14 pages.
Peters, J. (Dec. 2022). "Infection Risk in a Real-World Cohort of Patients Treated with Long-Term B-Cell Depletion for Autoimmune Neurologic Disease," Mult. Scler. Relat. Disord. 68:104400, 12 pages.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Petri, M. et al. (Aug. 2012). "Derivation and Validation of Systemic Lupus International Collaborating Clinics Classification Criteria for Systemic Lupus Erythematosus," Arthritis Rheum. 64(8):2677-2686, 12 pages.
Picard, D. et al. (Jan. 5, 1984). "A Lymphocyte-specific Enhancer in the Mouse Immunoglobulin K Gene," Nature 307:80-82.
Pitiot, A. et al. (Aug. 26, 2022). "Alternative Routes of Administration for Therapeutic Antibodies-State of the Art," Antibodies 11(3):56, 25 pages.
Pluückthun, A. (1994). "Antibodies from *Escherichia coli*," Chapter 11 in Handbook of Experimental Pharmacology 113:269-315.
Polyak, M.J. et al. (May 1, 2002). "Alanine-170 and Proline-172 are Critical Determinants for Extracellular CD20 Epitopes; Heterogeneity in the Fine Specificity of CD20 Monoclonal Antibodies is Defined by Additional Requirements Imposed by Both Amino Acid Sequence and Quaternary Structure," Blood 99(9):3256-3262.
Poosarla, V.G. et al. (2017, e-pub. Feb. 2, 2017). "Computational De Novo Design of Antibodies Binding to a Peptide With High Affinity," Biotech. Bioeng. 114(6):1331-1342.
Poppema, S. et al. (1987). "Preparation and Application of Monoclonal Antibodies: B Cell Panel and Paraffin Tissue Reactive Panel," Biotest Bulletin 3:131-139.
Portolano, S. et al. (Feb. 1, 1993). "Lack of Promiscuity in Autoantigen-Specific H and L Chain Combinations as Revealed by Human H and L Chain 'Roulette'," The Journal of Immunology 150(3):880-887.
Potter, K.N. et al. (Oct. 1, 2002). "Evidence for Involvement of a Hydrophobic Patch in Framework Region 1 of Human V4-34-Encoded Igs in Recognition of the Red Blood Cell I Antigen," Journal of Immunology 169(7):3777-3782.
Presta, L.G. (1992). "Antibody Engineering," Current Opinion in Structural Biology 2:593-596.
Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.
Presta, L.G. et al. (Sep. 1, 1993). "Humanization of an Antibody Directed Against IgE," J. Immunol. 151(5):2623-2632.
Queen, C. et al. (Dec. 1989). "A Humanized Antibody That Binds to the Interleukin 2 Receptor," Proc. Natl Acad. Sci. USA 86:10029-10033.
Rabia, L.A. et al. (Sep. 15, 2018). "Understanding and Overcoming Trade-Offs Between Antibody Affinity, Specificity, Stability and Solubility," Biochem. Eng, J. 137:365-374, 23 pages.
Ramos-Casal et al. (Apr. 2012). "B-Cell-Depleting Therapy in Systemic Lupus Erythermatosus," Am. J. Med. 125(4):327-336.
Ravetch, J.V. et al. (1991). "Fc Receptors," Annu. Rev. Immunol. 9:457-492.
Reddy, V. et al. (2013). "B-Cell Depletion in SLE: Clinical and Trial Experience with Rituximab and Ocrelizumab and Implications for Study Design," Arthritis Research & Therapy 15(Suppl 1):S2, 16 pages.
Reddy, V. et al. (2013). "OP0318 Use of an in Vitro Whole Blood Depletion Assay to Compare the Efficacy of B Cell Depleting Agents in Patients with Systemic Lupus Erythematosus," Annals of the Rheumatic Diseases 72(3):A162.1, 6 pages.
Reddy, V. et al. (2017, e-pub. Apr. 11, 2017). "Obinutuzumab Induces Superior B-Cell Cytotoxicity to Rituximab in Rheumatoid Arthritis and Systemic Lupus Erythematosus Patient Samples," Rheumatology 16:1227-1237.
Reddy, V. et al. (Jun. 22, 2016). "Optimising B-Cell Depletion in Autoimmune Disease: Is Obinutuzumab the Answer?," Drug Discovery Today 21(8):1330-1338, 31 pages.
Reddy, V. et al. (Jun. 9, 2016). "Improving B-Cell Depletion in Rheumatoid Arthritis and Systemic Lupus Erythematosus: Resistance to Rituximab and the Potential of Obinutuzumab," Annals of the Rheumatic Diseases 75(S2):116, 2 pages.
Reddy, V. et al. (May 2015). "Internalization of Rituzimab and the Efficiency of B Cell Depletion in Rheumatoid Arthritis and Systemic Lupus Erythematosus," Arthritis & Rheumatology 67(8):2046-2055, 17 pages.
Reff, M.E. et al. (Jan. 15, 1994). "Depletion of B Cells In Vivo by a Chimeric Mouse Human Monoclonal Antibody to CD20," Blood 83(2):435-445.
Reiter, Y. et al. (Dec. 1995). "Disulfide Stabilization of Antibody Fv: Computer Predictions and Experimental Evaluation," Protein Eng. 8(12):1323-1331.
Reiter, Y. et al. (Oct. 1996). "Engineering Antibody Fv Fragments for Cancer Detection and Therapy: Disulfide-Stabilized Fv Fragments," Nature Biotechnology 14:1239-1245.
Ridgway, J.B.B. et al. (1996). "'Knobs-Into-Holes' Engineering of Antibody CH3 Domains for Heavy Chain Heterodimerization," Protein Engineering 9(7):617-621.
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Robbins, M. et al. (Jun. 2009). "siRNA and Innate Immunity," Oligonucleotides 19(2):89-102.
Roche: (Jun. 11, 2019). "Roche's Gazyva (obinutuzumab) Delivers Positive Topline Results for Phase II Lupus nephritis Study," Roche Media Release, 3 pages.
Rogers, K.A. et al. (2014). "Obinutuzumab for the Treatment of Chronic Lymphocytic Leukemia," Drugs of Today 50(6):407-419.
Romee, R. et al. (May 2, 2013, e-pub. Mar. 13, 2013). "NK Cell CD16 Surface Expression and Function is Regulated by a Disintegrin and Metalloprotease-17 (ADAM17)," Blood. 121(18):3599-3608.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Roujeau, J.C. et al. (1984) "Silent Lupus Nephritis Among Patients with Discoid Lupus Erythematosus," Acta Derm. Venereol. 64:160-163.
Rovin, B.H. et al. (Apr. 27, 2012). "Efficacy and Safety of Rituximab in Patients with Active Proliferative Lupus Nephritis: The Lupus Nephritis Assessment with Rituximab Study," Arthritis & Rheumatism 64(4):1215-1226.
Rozema, D.B. et al. (Aug. 7, 2007, e-pub. Jul. 24, 2007). "Dynamic PolyConjugates for Targeted In Vivo Delivery of siRNA to Hepatocytes," Proc. Natl. Acad. Sci. USA 104(32):12982-12987, 6 pages.
Rudikoff, S. et al. (Mar. 1982). "Single Amino Acid Substitution Altering Antigen-Binding Specificity," Proc. Natl. Acad. Sci. USA 79:1979-1983.
Sambrook, J. et al. (2001). Molecular Cloning: A Laboratory Manual Cold Spring Harbor Laboratory Press, Cold Spring Harbor, N.Y., 3rd ed., 1 page, Table of Contents.
Sander, O. et al. (Sep. 25, 2021). "A Framework to Guide Dose & Regimen Strategy for Clinical Drug Development," CPT Pharmacometrics Syst. Pharmacol. 10(11):1276-1280.

(56) References Cited

OTHER PUBLICATIONS

Schett, G. et al. (2023, e-pub. Sep. 22, 2023). "CAR T-Cell Therapy in Autoimmune Diseases," The Lancet pp. 1-11.
Schier, R. et al. (1996). "Identification of Functional and Structural Amino-Acid Residues by Parsimonious Mutagenesis," Gene 169:147-155.
Schindler, T. et al. (Jun. 9, 2016). "Nobility, a Phase 2 Trial to Assess the Safety and Efficacy of Obinutuzumab, a Novel Type 2 Anti-CD20 Monoclonal Antibody (mAB) in Patients (Pts) With ISN/RPS Class III or IV Lupus Nephritis (LN)" Annals of the Rheumatic Diseases AB0423, 75(S2):1051, 1 page.
Schneider, B. et al. (2012, e-pub. Sep. 18, 2012). "Targeted siRNA Delivery and mRNA Knockdown Mediated by Bispecific Digoxigenin-binding Antibodies," Mol. Ther. Nucleic Acids 1:e46, 11 pages.
Schwartz, N. et al. (Sep. 2014). "The Pathogenesis, Diagnosis, and Treatment of Lupus Nephritis," Curr. Opin. Reheumatiol. 26(5):502-509, 14 pages.
Scott, E. et al. (2016, e-pub. Apr. 18, 2016). "Immune Cells and Type 1 IFN in Urine of SLE Patients Correlate with Immunopathology in the Kidney," Clinical Immunology 168:16-24.
Sehn, L.H. et al. (May 31, 2012, e-pub. Mar. 20, 2012) "A Phase 1 Study of Obinutuzumab Induction Followed by 2 Years of Maintenance in Patients with Relapsed CD20-Positive B-Cell Malignancies," Blood 119(22):5118-5125.
Semple, S.C. et al. (Feb. 2010, e-pub. Jan. 17, 2010). "Rational Design of Cationic Lipids for siRNA Delivery," Nat. Biotechnol. 28(2):172-176, 7 pages.
Sheriff, S. et al. (Sep. 1996). "Redefining the Minimal Antigen-Binding Fragment," Nature Struct. Biol. 3(9):733-736.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries Synthetic Heavy Chain Complementarity Determining Regions," J. Mol. Biol. 338(2):299-310.
Sims, M.J. et al. (Aug. 15, 1993). "A Humanized CD18 Antibody Can Block Function without Cell Destruction," The Journal of Immunology 151(4):2296-2308.
Smith, P.R. et al. (Oct. 1, 1999). "Drug-Induced Lupus Nephritis in HIV Infection," Rheumatology 38:1017-1018, 8 pages.
Song (2009). "Generation of Multivalent Antibody Against Small Hapten and Studies on Its Bioactivities," 10:1-76, 88 pages. English Abstract.
Song, E. et al. (Jun. 2005, e-pub. May 22, 2005). "Antibody Mediated In Vivo Delivery of Small Interfering Rnas via Cell-Surface Receptors," Nat. Biotechnol. 23(6):709-717.
Sou, K. et al. (May-Jun. 2000, e-pub. Apr. 14, 2000). "Poly(ethylene glycol)—Modification of the Phospholipid Vesicles by Using the Spontaneous Incorporation of Poly(ethylene glycol)—Lipid Into the Vesicles," Bioconjug. Chem. 11(3):372-379.
Soutschek, J. et al. (Nov. 11, 2004). "Therapeutic Silencing of an Endogenous Gene by Systemic Administration of Modified siRNAs," Nature 432(7014):173-178.
Stamenkovic, I. et al. (Jun. 1988). "Analysis of Two cDNA Clones Encoding the B Lymphocyte Antigen CD20 (B1, Bp35), a type III Intergal Membrane Protein," J. Exp. Med. 167:1975-1980.
Stites, D.P. et al. (1994). "Immunoglobulin Protiens," Chapter 6 in Basic Clinical Immunology, 8th Edition, Appleton & Lange, Norwalk, CT, pp. 66-79.
Su, G.-X. et al. (Sep. 1, 2012). "Rituximab Therapy for Severe Pediatric Systemic Lupus Erythematosus," Chinese Journal of Pediatrics, 2 pages.
Summons to Attend Oral Proceedings Pursuant to Rule 115(1) EPC, mailed on Mar. 4, 2021, for European Patent Application No. 16725982.9, 8 pages.
Tan, E. M. et al. (Nov. 1982). "The 1982 Revised Criteria for the Classification of Systemic Lupus Erythematosus," Arthritis and Rheumatism 25(11):1271-1277.
Tang, X. et al. (Jan. 2010). "Clinical and Serologic Correlations and Autoantibody Clusters in Systemic Lupus Erythematosus: A Retrospective Review of 917 Patients in South China," Medicine 89(1):62-67.
Tao, W. et al. (Sep. 2010, e-pub. Jul. 13, 2010). "Noninvasive Imaging of Lipid Nanoparticle-Mediated Systemic Delivery of Small-Interfering RNA to the Liver," Mol. Ther. 18(9):1657-1666.
Tedder, T.F. et al. (Apr. 1, 1989). "Structure of the Gene Encoding of the Human B Lymphocyte Differentiation Antigen CD20 (B1)," J. Immunol. 142(7):2560-2568.
Tedder, T.F. et al. (Jan. 1988). "Isolation and Structure of a cDNA Encoding the B1 (CD20) Cell-Surface Antigen of Human B Lymphocytes," Proc. Natl. Acad. Sci. USA 85(1):208-212.
Tew, G.W. et al. (2010). "Baseline Autoantibody Profiles Predict Normalization of Complement and Anti-dsDNA Autoantibody Levels Following Rituximab Treatment in Systemic Lupus Erythematosus," Lupus 19:146-157.
Thakare, S.B. et al. (Aug. 2023, e-pub. Jun. 14, 2023). "Novel Therapeutics for Management of Lupus Nephritis: What is Next?" Kidney Med. 5(8):100688, 7 pages.
The Brazilian Office Action, mailed on Aug. 13, 2020, in the related Brazilian Appl. BR11231601495-9, 5 pages.
The Chinese Office Action, mailed on Oct. 23, 2020, in the related Chinese Appl. No. 201710588836.1, with English Translation, 13 pages.
Tiera, M.J. et al. (Oct. 2013). "Polymeric Systems as Nanodevices for siRNA Delivery," Curr. Gene Ther. 13(5):358-369.
Toloue, M.M. et al. (2011). "Chapter 8: Antibody Targeted siRNA Delivery," Methods Mol. Biol. 764:123-139.
Torgov, M.Y. et al. (2005; e-published on Apr. 27, 2005). "Generation of an Intensely Potent Anthracycline by a Monoclonal Antibody-B-Galactosidase Conjugate," Bioconjugate Chem. 16:717-721.
Traunecker, A. et al. (1991). "Bispecific Single Chain Molecules (Janusins) Target Cytotoxic Lymphocytes on HIV Infected Cells," EMBO J. 10(12):3655-3659.
Trautmann, A. et al. (2023, e-pub. Oct. 21, 2022). "IPNA Clinical Practice Recommendations for the Diagnosis and Management of Children with Steroid-Sensitive Nephrotic Syndrome," Pediatr Nephrol 38:877-919.
Tselios, K. et al. (Feb. 2014, e-pub. Aug. 15, 2013). "Do Current Arterial Hypertension Treatment Guidelines Apply to Systemic Lupus Erythematosus Patients? A Critical Appraisal," Seminar in Arthritis and Rheumatism 43(4):521-525. Abstract Only.
Tsokos, G.C. (Dec. 1, 2011). "Systemic Lupus Erythematosus," N. Engl. J. Med. 365:2110-2121.
Tutt, A. et al. (Jul. 1, 1991). "Trispecific F(ab')3 Derivatives That Use Cooperative Signaling via the TCR/CD3 Complex and CD2 to Activate and Redirect Resting Cytotoxic T Cells," J. Immunol. 147:60-69.
Umaña, P. et al. (Feb. 1999). "Engineered Glycoforms of an Antineuro• Blastoma IgG 1 With Optimized Antibody•Dependent Cellular Cytotoxic Activity," Nat. Biotechnol. 17:176-180.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Valentine, M.A. et al. (Jul. 5, 1989). "Phosphorylation of the CD20 Phosphoprotein in Resting B Lymphocytes. Regulation by Protein Kinase C," J. Biol. Chem. 264(19):11282-11287.
Van Dijk, M.A. et al. (Aug. 2001). "Human Antibodies as Next Generation Therapeutics," Curr. Opin. Che. Biology 5(4):368-374.
Vaswani, S.K. et al. (Aug. 1998). "Humanized Antibodies as Potential Therapeutic Drugs," Ann. Allergy, Asthma & Immunol. 1:105-115.
Vincent, P. et al. (1993). "A Comparison of the Binding of Biotin and Biotinylated Macromolecular Ligands to an Anti-Biotin Monoclonal Antibody and to Streptavidin," Journal of Immunological Methods 165:177-182.
Vital, E.M. et al. (Oct. 2011). "B Cell Biomarkers of Rituximab Responses in Systemic Lupus Erythematosus," Arthritis Rheum. 63(10):3038-3047.
Vitetta, E.S. et al. (Nov. 20, 1987). "Redesigning Nature's Poisons to Create Anti-Tumor Reagents," Science 238:1098-1104.

(56) References Cited

OTHER PUBLICATIONS

Vo, A.A. et al. (2014). "Benefits, Efficacy, Cost-Effectiveness and Infectious Complications in Transplant Patients Desensitized with Intravenous Immunoglobulin and Anti-CD20 Therapy," Clinical and Experimental Immunology 174:48-51.
Vo, A.A. et al. (Aug. 15, 2014). "Benefits of Rituximab Combined with Intravenous Immunoglobulin for Desensitization in Kidney Transplant Recipients," Transplantation 98(3):312-319.
Vo, A.A. et al. (Jul. 17, 2008). "Rituximab and Intravenous Immune Globulin for Desensitization during Renal Transplantation," N. Engl. J. Med. 359:242-251.
Vollmers, H.P. et al. (2005) "Death by Stress: Natural IgM-induced Apoptosis," Methods Find Exp Clin Pharmacol. 27(3):1-7.
Vollmers, H.P. et al. (2005). "The 'Early Birds': Natural IgM Antibodies and Immune Surveillance," Histology and Histopathology, 20(3):927-937.
Wark, K.L. et al. (2006; e-pub. May 22, 2006). "Latest Technologies for the Enhancement of Antibody Affinity," Advanced Drug Delivery Reviews 58:657-670.
Weening, J.J. et al. (2004). "The Classification of Glomerulonephritis in Systemic Lupus Erythematosus Revisited," J. Am. Soc. Nephrol. 15:241-250.
Weening, J.J. et al. (2004). "The Classification of Glomerulonephritis in Systemic Lupus Erythematosus Revisited," Kidney Int. 65:521-530.
Weidenbusch, M. et al. (2012, e-pub. Jul. 3, 2012). "Beyond the Lunar Trial. Efficacy of Rituximab in Refractory Lupus Nephritis," Nephrology Dial. Transplant. 28(1):106-111.
Weidle, U.H. et al. (Jan.-Feb. 2013). "The Intriguing Options of Multispecific Antibody Formats for Treatment of Cancer," Cancer Genomics Proteomics 10(1):1-18.
Whittingham, S. (Apr. 1998). "Autoantibodies in Systemic Lupus Erythematosus," Ann. Acad. Med. 17(2):195-200.
WHO Drug Information. (2008). Proposed Inn List 99 International Nonproprietary Names for Pharmaceutical Substances, World Health Organization, Geneva, Switzerland, 22(2):77, 78, & 174.
WHO Drug Information. (2009). International Nonproprietary Names for Pharmaceutical Substances, World Health Organization, Geneva, Switzerland, 23(2):176.
WHO Drug Information. (2012). International Nonproprietary Names for Pharmaceutical Substances, World Health Organization, Geneva, Switzerland, 26(4):453.
Williams, D.G. et al. (Jan. 1, 2010). "Chapter 21: Humanising Antibodies by CDR Grafting," In Antibody Engineering 1:319-339.
Winter, G. et al. (1994). "Making Antibodies by Phage Display Technology," Ann. Rev. Immunol. 12:433-455.
Wittmann, S. et al. (2004). "Cytokine Upregulation of Surface Antigens Correlates to the Priming of the Neutrophil Oxidative Burst Response," Cytometry Part A. 57A(1):53-62.
Wolff, J.A. et al. (Jan. 2008, e-pub. Oct. 23, 2007). "Breaking the Bonds: Non-Viral Vectors Become Chemically Dynamic," Mol. Ther. 16(1):8-15.
Wong, S.C. et al. (Dec. 2012). "Co-Injection of a Targeted, Reversibly Masked Endosomolytic Polymer Dramatically Improves the Efficacy of Cholesterol-Conjugated Small Interfering RNAs In Vivo," Nucleic Acid Ther. 22:380-390.
Wright, A. et al. (Jan. 1997). "Effect of Glycosylation on Antibody Function: Implications for Genetic Engineering," Trends Biotech. 15:26-32.
Written Opinion mailed Oct. 13, 2015 in PCT Application No. PCT/EP2015/064322, filed Jun. 25, 2015, 6 pages.
Written Opinion mailed on Sep. 21, 2016, for PCT Application No. PCT/US2016/031683, filed on May 10, 2016, 9 pages.
Written Opinion mailed on Sep. 27, 2016, for PCT Application No. PCT/US2016/039905, filed on Jun. 28, 2016, 6 pages.
Wu, H. (2003). "Simultaneous Humanization and Affinity Optimization of Monoclonal Antibodies," Methods in Mol. Biol. 207:197-212.
Xu, J.L. et al. (Jul. 2000). "Diversity in the CDR3 Region of VH is Sufficient for Most Antibody Specificities," Immunity 13:37-45.
Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.
Yap, D.Y.H. et al. (2013, e-pub. Nov. 12, 2012). "Long-Term Data on Corticosteroids and Mycophenolate Mofetil Treatment in Lupus Nephritis," Rheumatology. 52:480-486.
Yazaki, P.J. et al. (2003). "Expression of Recombinant Antibodies in Mammalian Cell Lines," Methods in Molecular Biology 248:255-268.
Yelton, D.E. et al. (1995). "Affinity Maturation of the BR96 Anti-Carcinoma Antibody by Codon-Based Mutagenesis," J. Immunol. 155:1994-2004.
Yu, B. et al. (Mar. 2009, e-pub. Mar. 19, 2009). "Targeted Delivery Systems for Oligonucleotide Therapeutics," AAPS J 11(1):195-203.
Zahnd, C. et al. (Apr. 30, 2004; e-pub. on Jan. 30, 2004). "Directed in Vitro Evolution and Crystallographic Analysis of a Peptide-Binding Single Chain Antibody Fragment (scFv) with Low Picomolar Affinity," Journal of Biological Chemistry 279(18):18870-18877.
Zapata, G. et al. (1995). "Engineering Linear F(ab')2 Fragments for Efficient Production in *Escherichia coli* and Enhanced Antiproliferative Activity," Protein Engineering 8(10):1057-1062.
Zhou, Q.-H. et al. (Aug. 17, 2011). "Delivery of a Peptide Radiopharmaceutical to Brain with an IgG-Avidin Fusion Protein," Bioconjugate Chemistry 22(8):1611-1618, 21 pages.
Zimmermann, T.S. et al. (Mary 4, 2006, e-pub. Mar. 26, 2006). "RNAi-Mediated Gene Silencing in Non-Human Primates," Nature 441(7089):111-114, 18 pages.

* cited by examiner

COMPOSITIONS AND METHODS OF TREATING LUPUS NEPHRITIS

CROSS REFERENCE TO RELATED APPLICATIONS

This application is a continuation of U.S. application Ser. No. 19/039,642, filed Jan. 28, 2025, which is a continuation of U.S. application Ser. No. 18/045,313, filed Oct. 10, 2022, now abandoned, which is a continuation of U.S. application Ser. No. 16/363,836, filed Mar. 25, 2019, now abandoned, which is a continuation of U.S. application Ser. No. 15/151,449, filed May 10, 2016, now abandoned, which claims the priority benefit of U.S. Provisional Application Ser. No. 62/159,876, filed May 11, 2015; and 62/300,052, filed Feb. 25, 2016; each of which is incorporated herein by reference in its entirety.

REFERENCE TO AN ELECTRONIC SEQUENCE LISTING

The contents of the electronic sequence listing (146392032204seqlist.xml; Size: 57,279 bytes; and Date of Creation: Jul. 21, 2025) are incorporated herein by reference in their entirety.

FIELD OF THE INVENTION

Provided herein are methods for treating or delaying progression of lupus nephritis in an individual that has lupus by administering a type II anti-CD20 antibody. Also provided herein are methods for treating or delaying progression of rheumatoid arthritis (RA) or systemic lupus erythematosus (SLE) in an individual by administering an anti-CD20 antibody.

BACKGROUND

Lupus is an autoimmune disease involving antibodies that attack connective tissue. The disease is estimated to affect nearly 1 million Americans, primarily women between the ages of 20-40. The principal form of lupus is a systemic one (systemic lupus erythematosus; SLE). SLE has an incidence of about 1 in 700 women between the ages of 20 and 60. SLE can affect any organ system and can cause severe tissue damage. Untreated lupus can be fatal as it progresses from attack of skin and joints to internal organs, including lung, heart, and kidneys, with renal disease, termed lupus nephritis (LN), being the primary concern. Lupus mainly appears as a series of flare-ups, with intervening periods of little or no disease manifestation.

LN is one of the most acute areas of damage associated with pathogenicity in SLE, and accounts for at least 50% of the mortality and morbidity of the disease. Currently, there are no really curative treatments for patients who have been diagnosed with SLE or LN. From a practical standpoint, physicians generally employ a number of powerful immunosuppressive drugs such as high-dose corticosteroids, e.g., prednisone, or azathioprine or cyclophosphamide, which are given during periods of flare-ups, but may also be given persistently for those who have experienced frequent flare-ups. Even with effective treatment, which reduces symptoms and prolongs life, many of these drugs have potentially harmful side effects to the patients being treated. As such, there remains a need for more effective treatments against LN with fewer harmful side effects.

Two anti-CD20 antibodies have been tested in clinical studies for efficacy in treating lupus nephritis. Rituximab, a type I anti-CD20 antibody, failed to meet its primary endpoint of overall response (weighted toward complete renal response, or CRR) but resulted in a 15.3% increase in partial renal response (PRR) (Rovin, B. H. et al. (2012) *Arthritis Rheum.* 64:1215-1226). Ocrelizumab, another type I anti-CD20 antibody, was terminated, in part, because of an imbalance of serious infectious events (Mysler, E. F. et al. (2013) *Arthritis Rheum.* 65:2368-2379).

Obinutuzumab, a type II anti-CD20 antibody, has been shown to produce superior B cell depletion, as compared to rituximab. Significantly greater B cell depletion was observed with obinutuzumab treatment, compared to rituximab treatment, in cynomolgous monkeys (Mössner, E. et al. (2010) *Blood* 115:4393-4402). Therefore, there remains a need for testing the efficacy of type II anti-CD20 antibodies in treating or preventing LN in patients with lupus.

All references cited herein, including patent applications and publications, are incorporated by reference in their entirety.

SUMMARY

In certain aspects, provided herein are methods for treating or delaying progression of lupus nephritis in an individual, comprising administering to the individual at least a first antibody exposure to a type II anti-CD20 antibody and a second antibody exposure to the type II anti-CD20 antibody. In some embodiments, the individual has lupus. In some embodiments, the second antibody exposure is not provided until from about 18 weeks to about 26 weeks after the first antibody exposure. In some embodiments, the second antibody exposure is not provided until from about 4.5 months to about 6.5 months after the first antibody exposure. In some embodiments, the first antibody exposure comprises one or two doses of the type II anti-CD20 antibody, the first antibody exposure comprising a total exposure of between about 1800 mg and about 2200 mg of the type II anti-CD20 antibody. In some embodiments, the second antibody exposure comprises one or two doses of the type II anti-CD20 antibody, the second antibody exposure comprising a total exposure of between about 1800 mg and about 2200 mg of the type II anti-CD20 antibody. In some embodiments, the type II anti-CD20 antibody comprises a heavy chain comprising HVR-H1 sequence of SEQ ID NO: 1, HVR-H2 sequence of SEQ ID NO:2, and HVR-H3 sequence of SEQ ID NO:3, and a light chain comprising HVR-L1 sequence of SEQ ID NO: 4, HVR-L2 sequence of SEQ ID NO:5, and HVR-L3 sequence of SEQ ID NO:6. In some embodiments, the individual is at risk for developing class III or class IV lupus nephritis. In some embodiments, the methods are for preventing lupus nephritis in an individual that has lupus. In some embodiments, the methods are for preventing lupus nephritis in an individual that has SLE. In some embodiments, the methods are for treating or delaying progression of lupus nephritis in an individual that has SLE.

In some embodiments, the first antibody exposure comprises a first dose of the type II anti-CD20 antibody and a second dose of the type II anti-CD20 antibody, and the second dose of the first antibody exposure is not provided until from about 1.5 weeks to about 2.5 weeks after the first dose of the first antibody exposure. In some embodiments, the first antibody exposure comprises a first dose of the type II anti-CD20 antibody and a second dose of the type II anti-CD20 antibody, and the second dose of the first antibody exposure is not provided until about 2 weeks after the first dose of the first antibody exposure. In some embodiments, the first antibody exposure comprises a first dose of the type II anti-CD20 antibody and a second dose of the type II anti-CD20 antibody, and the second dose of the first antibody exposure is not provided until from about 10 days to about 17 days after the first dose of the first antibody exposure. In some embodiments, the first antibody exposure comprises a first dose of the type II anti-CD20 antibody and a second dose of the type II anti-CD20 antibody, and the second dose of the first antibody exposure is not provided until about 14 after the first dose of the first antibody exposure. In some embodiments, the first dose of the first antibody exposure is about 1000 mg of the type II anti-CD20 antibody. In some embodiments, the second dose of the first antibody exposure is about 1000 mg of the type II anti-CD20 antibody. In some embodiments, the second antibody exposure comprises a first dose of between about 900 mg and about 1100 mg of the type II anti-CD20 antibody and a second dose of between about 900 mg and about 1100 mg of the type II anti-CD20 antibody. In some embodiments, the second antibody exposure comprises a first dose of the type II anti-CD20 antibody and a second dose of the type II anti-CD20 antibody, and the second dose of the second antibody exposure is not provided until from about 1.5 weeks to about 2.5 weeks after the first dose of the second antibody exposure. In some embodiments, the second antibody exposure comprises a first dose of the type II anti-CD20 antibody and a second dose of the type II anti-CD20 antibody, and the second dose of the second antibody exposure is not provided until about 2 weeks after the first dose of the second antibody exposure. In some embodiments, the second antibody exposure comprises a first dose of the type II anti-CD20 antibody and a second dose of the type II anti-CD20 antibody, and the second dose of the second antibody exposure is not provided until from about 10 days to about 17 days after the first dose of the second antibody exposure. In some embodiments, the second antibody exposure comprises a first dose of the type II anti-CD20 antibody and a second dose of the type II anti-CD20 antibody, and the second dose of the second antibody exposure is not provided until about 14 days after the first dose of the second antibody exposure. In some embodiments, the first dose of the second antibody exposure is about 1000 mg of the type II anti-CD20 antibody. In some embodiments, the second dose of the second antibody exposure is about 1000 mg of the type II anti-CD20 antibody. In some embodiments, the first antibody exposure and the second antibody exposure are administered intravenously. In some embodiments, the individual has class III or class IV lupus nephritis. In some embodiments, the individual is at risk for developing class III or class IV lupus nephritis.

In certain aspects, provided herein are methods for treating or delaying progression of lupus nephritis in an individual that has lupus, comprising administering to the individual an effective amount of a type II anti-CD20 antibody; wherein the type II anti-CD20 antibody comprises a heavy chain comprising HVR-H1 sequence of SEQ ID NO:1, HVR-H2 sequence of SEQ ID NO:2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO: 6; and wherein the individual has class III or class IV lupus nephritis. In some embodiments, the individual is at risk for developing class III or class IV lupus nephritis. In some embodiments, the methods are for preventing lupus nephritis in an individual that has lupus. In some embodiments, the methods are for preventing lupus nephritis in an individual that has SLE. In some embodiments, the methods are for treating or delaying progression of lupus nephritis in an individual that has SLE.

In certain aspects, provided herein are methods for treating or delaying progression of lupus nephritis in an individual that has lupus, comprising administering to the individual a dose of about 1000 mg of a type II anti-CD20 antibody, wherein the type II anti-CD20 antibody comprises a heavy chain comprising HVR-H1 sequence of SEQ ID NO: 1, HVR-H2 sequence of SEQ ID NO:2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO: 6, and wherein the dose is administered to the individual once on days 1, 15, 168, and 182. In certain aspects, provided herein are methods for treating or delaying progression of lupus nephritis in an individual that has lupus, comprising administering to the individual a dose of about 1000 mg of a type II anti-CD20 antibody, wherein the type II anti-CD20 antibody comprises a heavy chain comprising HVR-H1 sequence of SEQ ID NO: 1, HVR-H2 sequence of SEQ ID NO:2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO: 6, and wherein the dose is administered to the individual once on weeks 0, 2, 24, and 26. In some embodiments, week 0 corresponds to day 1. In some embodiments, the individual has class III or class IV lupus nephritis. In some embodiments, the type II anti-CD20 antibody is obinutuzumab.

In some embodiments of any of the above embodiments, the type II anti-CD20 antibody is administered intravenously. In some embodiments of any of the above embodiments, the individual does not have class III (C) or class IV (C) lupus nephritis. In some embodiments of any of the above embodiments, the individual has class V lupus nephritis. In some embodiments of any of the above embodiments, the methods further include administering to the individual an effective amount of an immunosuppressive agent. In some embodiments, the immunosuppressive agent comprises mycophenolic acid, a derivative thereof, or a salt thereof. In some embodiments, the immunosuppressive agent comprises mycophenolate mofetil. In some embodiments of any of the above embodiments, the methods further include administering to the individual an effective amount of a glucocorticoid or corticosteroid. In some embodiments, the glucocorticoid or corticosteroid comprises methylprednisolone. In some embodiments, the glucocorticoid or corticosteroid comprises prednisone. In some embodiments of any of the above embodiments, the methods further include administering to the individual an effective amount of an antihistamine. In some embodiments, the antihistamine comprises diphenhydramine. In some embodiments of any of the above embodiments, the methods further include administering to the individual an effective amount of a non-steroidal anti-inflammatory drug (NSAID). In some embodiments, the NSAID comprises acetaminophen. In some embodiments of any of the above embodiments, the methods further include administering to the individual a standard of care treatment. In some embodiments, the standard of care treatment comprises treatment with one or more of an angiotensin-converting enzyme (ACE) inhibitor, an angiotensin-receptor blocker, cyclophosphamide, mycophenolate mofetil, azathioprine, and a glucocorticoid or corticosteroid. In some embodiments, the standard of care treatment is administered after the first antibody exposure to the type II anti-CD20 antibody and/or after the second antibody exposure to the type II anti-CD20 antibody. In some embodiments of any of the above embodiments, the methods further include administering to the individual an effective amount of an antihypertensive agent. In some embodiments, the antihypertensive agent is an angiotensin-converting enzyme (ACE) inhibitor or an angiotensin-receptor blocker. In some embodiments of any of the above embodiments, the method results in a complete renal response (CRR) in the individual. In some embodiments of any of the above embodiments, the method results in a depletion of circulating peripheral B cells in the individual. In some embodiments, the circulating peripheral B cells are CD19+ B cells. In some embodiments of any of the above embodiments, the type II anti-CD20 antibody is a humanized or human antibody. In some embodiments of any of the above embodiments, the type II anti-CD20 antibody is afucosylated. In some embodiments of any of the above embodiments, the type II anti-CD20 antibody is nonfucosylated (e.g., as described in U.S. Pat. No. 8,883,980). In some embodiments of any of the above embodiments, the heavy chain of the type II anti-CD20 antibody comprises a heavy chain variable region comprising the amino acid sequence of SEQ ID NO:7. In some embodiments of any of the above embodiments, the light chain of the type II anti-CD20 antibody comprises a light chain variable region comprising the amino acid sequence of SEQ ID NO:8. In some embodiments of any of the above embodiments, the type II anti-CD20 antibody is obinutuzumab. In some embodiments of any of the above embodiments, the individual or patient is a human.

In certain aspects, provided herein are kits or articles of manufacture for treating or delaying progression of lupus nephritis in an individual that has lupus, comprising (a) a container comprising a type II anti-CD20 antibody, wherein the type II anti-CD20 antibody comprises a heavy chain comprising HVR-H1 sequence of SEQ ID NO:1, HVR-H2 sequence of SEQ ID NO: 2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO:6; and (b) a package insert with instructions for treating or delaying progression of lupus nephritis in an individual, wherein the instructions indicate that at least a first antibody exposure to a type II anti-CD20 antibody and a second antibody exposure to the type II anti-CD20 antibody are administered to the individual, the second antibody exposure not being provided until from about 18 weeks to about 26 weeks after the first antibody exposure; wherein the first antibody exposure comprises one or two doses of the type II anti-CD20 antibody, the first antibody exposure comprising a total exposure of between about 1800 mg and about 2200 mg of the type II anti-CD20 antibody; and wherein the second antibody exposure comprises one or two doses of the type II anti-CD20 antibody, the second antibody exposure comprising a total exposure of between about 1800 mg and about 2200 mg of the type II anti-CD20 antibody. In some embodiments, the kits or articles of manufacture further include (c) a second medicament, wherein the type II anti-CD20 antibody is a first medicament; and (d) instructions on the package insert for administering the second medicament to the subject. In some embodiments, the second medicament is an immunosuppressive agent, a glucocorticoid, a corticosteroid, an anti-malarial agent, a cytotoxic agent, an integrin antagonist, a cytokine antagonist, or a hormone. In some embodiments, the heavy chain of the type II anti-CD20 antibody comprises a heavy chain variable region comprising the amino acid sequence of SEQ ID NO:7. In some embodiments, the light chain of the type II anti-CD20 antibody comprises a light chain variable region comprising the amino acid sequence of SEQ ID NO:8. In some embodiments, the type II anti-CD20 antibody is obinutuzumab. In some embodiments, the kits or articles of manufacture are for preventing lupus nephritis in an individual that has SLE. In some embodiments, the kits or articles of manufacture are for treating or delaying progression of lupus nephritis in an individual that has SLE.

In certain aspects, provided herein are methods for treating or delaying progression of rheumatoid arthritis (RA) or systemic lupus erythematosus (SLE) in an individual, comprising administering to the individual an effective amount of an anti-CD20 antibody, wherein the antibody comprises a heavy chain variable region comprising an HVR-H1 sequence of SEQ ID NO: 1, an HVR-H2 sequence of SEQ ID NO:2, and an HVR-H3 sequence of SEQ ID NO:3, and a light chain variable region comprising an HVR-L1 sequence of SEQ ID NO:4, an HVR-L2 sequence of SEQ ID NO:5, and an HVR-L3 sequence of SEQ ID NO:6. In some embodiments, the antibody is administered intravenously. In some embodiments, the method results in a depletion of circulating peripheral B cells in the individual. In some embodiments, the circulating peripheral B cells are CD19+ B cells. In some embodiments, the antibody is a humanized or human antibody. In some embodiments, the antibody is afucosylated. In some embodiments, the heavy chain variable region comprises the amino acid sequence of SEQ ID NO: 7. In some embodiments, the light chain variable region comprises the amino acid sequence of SEQ ID NO:8. In some embodiments, the heavy chain variable region comprises the amino acid sequence of SEQ ID NO:7 and the light chain variable region comprises the amino acid sequence of SEQ ID NO:8. In some embodiments, the antibody is obinutuzumab. In some embodiments, the antibody comprises a modified Fc region. In some embodiments, the Fc region comprises a modification for attenuating effector function. In some embodiments, the Fc region is a human IgG1 Fc region. In some embodiments, the human IgG1 Fc region comprises L234A, L235A and P329G amino acid substitutions, numbering according to EU index.

In certain aspects, provided herein are compositions for use in treating or delaying progression of rheumatoid arthritis (RA) or systemic lupus erythematosus (SLE) in an individual, the compositions comprising an anti-CD20 antibody, wherein the antibody comprises a heavy chain variable region comprising an HVR-H1 sequence of SEQ ID NO:1, an HVR-H2 sequence of SEQ ID NO:2, and an HVR-H3 sequence of SEQ ID NO:3, and a light chain variable region comprising an HVR-L1 sequence of SEQ ID NO:4, an HVR-L2 sequence of SEQ ID NO:5, and an HVR-L3 sequence of SEQ ID NO:6. In some embodiments, the composition is administered intravenously. In some embodiments, administering the composition results in a depletion of circulating peripheral B cells in the individual. In some embodiments, the circulating peripheral B cells are CD19+ B cells. In some embodiments, the antibody is a humanized or human antibody. In some embodiments, the antibody is afucosylated. In some embodiments, the heavy chain variable region comprises the amino acid sequence of SEQ ID NO:7. In some embodiments, the light chain variable region comprises the amino acid sequence of SEQ ID NO: 8. In some embodiments, the heavy chain variable region comprises the amino acid sequence of SEQ ID NO:7 and the light chain variable region comprises the amino acid sequence of SEQ ID NO: 8. In some embodiments, the antibody is obinutuzumab. In some embodiments, the antibody comprises a modified Fc region. In some embodiments, the Fc region comprises a modification for attenuating effector function. In some embodiments, the Fc region is a human IgG1 Fc region. In some embodiments, the human IgG1 Fc region comprises L234A, L235A and P329G amino acid substitutions, numbering according to EU index. In some embodiments of any of the above embodiments, the individual or patient is a human.

In certain aspects, provided herein is use of an anti-CD20 antibody for the manufacture of a medicament for use in treatment of rheumatoid arthritis (RA) or systemic lupus erythematosus (SLE) in an individual, wherein the antibody comprises a heavy chain variable region comprising an HVR-H1 sequence of SEQ ID NO: 1, an HVR-H2 sequence of SEQ ID NO: 2, and an HVR-H3 sequence of SEQ ID NO:3, and a light chain variable region comprising an HVR-L1 sequence of SEQ ID NO:4, an HVR-L2 sequence of SEQ ID NO:5, and an HVR-L3 sequence of SEQ ID NO:6.

In certain aspects, provided herein are kits or articles of manufacture for treating or delaying progression of rheumatoid arthritis (RA) or systemic lupus erythematosus (SLE) in an individual, comprising (a) a container comprising an anti-CD20 antibody, wherein the antibody comprises a heavy chain variable region comprising an HVR-H1 sequence of SEQ ID NO:1, an HVR-H2 sequence of SEQ ID NO:2, and an HVR-H3 sequence of SEQ ID NO:3, and a light chain variable region comprising an HVR-L1 sequence of SEQ ID NO:4, an HVR-L2 sequence of SEQ ID NO:5, and an HVR-L3 sequence of SEQ ID NO:6; and (b) a package insert with instructions for administering an effective amount of anti-CD20 antibody to treat or delay progression of rheumatoid arthritis (RA) or systemic lupus erythematosus (SLE) in an individual. In some embodiments, the package insert includes instructions for administering the antibody intravenously. In some embodiments, the antibody is a humanized or human antibody. In some embodiments, the antibody is afucosylated. In some embodiments, the heavy chain variable region comprises the amino acid sequence of SEQ ID NO:7. In some embodiments, the light chain variable region comprises the amino acid sequence of SEQ ID NO:8. In some embodiments, the heavy chain variable region comprises the amino acid sequence of SEQ ID NO: 7 and the light chain variable region comprises the amino acid sequence of SEQ ID NO:8. In some embodiments, the antibody is obinutuzumab. In some embodiments, the antibody comprises a modified Fc region. In some embodiments, the Fc region comprises a modification for attenuating effector function. In some embodiments, the Fc region is a human IgG1 Fc region. In some embodiments, the human IgG1 Fc region comprises L234A, L235A and P329G amino acid substitutions, numbering according to EU index.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE FIGURES

FIG. 2A shows whole blood samples from patients with RA (n=31) and SLE (n=34). Samples were incubated with or without anti-CD20 mAbs, RTX, $OBZ_{Gly}$ and OBZ for 24 hours before flow cytometry to analyze B cell death. Values are the mean of triplicate wells. The horizontal line in the box represents the median, the box represents the interquartile range and the whiskers represent the range. FIG. 2B shows the frequency of surface accessible mAbs. The frequency was assessed by flow cytometry after six hours of incubation with isolated B cells from patients with RA (n=5) and SLE (n=8) with or without prior incubation with anti-FcγRII blocking mAb, AT10. The horizontal line represents the median. FIG. 2C shows CDC induced by RTX and OBZ. Isolated B cells (Healthy control (HC), n=2; RA, n=2 and SLE, n=3) were incubated with RTX or OBZ for 30 minutes with normal healthy serum (NHS) or heat inactivated serum (HIS) before analyzing for the frequency of lysed CD19+Av+PI+ B cells. FIG. 2D shows the fold increase in CD19+Av+PI+ cells in samples incubated with NHS vs HIS representing the efficiency of CDC by mAbs. RTX, rituximab; OBZ, Obinutuzumab; RA, rheumatoid arthritis; SLE, systemic lupus erythematosus. HC, Healthy control * $p<0.05$; , $p<0.005$; *, $p<0.0001$ and ns, not significant.

FIG. 3A shows flow cytometry gating of forward scatter vs. side scatter. FIG. 3B shows flow cytometry gating of CD56 vs. CD3. FIG. 3C shows flow cytometry gating of forward scatter vs. CD107a. FIG. 3D shows flow cytometry gating of forward scatter vs. CD16. Three subpopulations of CD3−CD56+ NK cells were identified based on the relative expression of CD16 (boxed as high, medium, and low). The relative frequency of activated CD107a+ NK cells differed in these 3 subpopulations based on CD16 expression in a hierarchical manner CD16++<CD16+<CD16−. FIG. 3E shows flow cytometry gating of forward scatter vs. CD107a for the high box. FIG. 3F shows flow cytometry gating of forward scatter vs. CD107a for the medium box. FIG. 3G shows flow cytometry gating of forward scatter vs. CD107a for the low box.

FIG. 4A shows the frequency of CD3−CD56+ NK cells in the lymphocyte gate, CD3−CD56+CD107a+ NK cells and CD3−CD56−CD16+ NK cells as a percentage of total NK cells or CD19+ cells. Horizontal lines represent the median. FIG. 4B shows the frequency of CD3−CD56+CD107a+ NK cells and the fold increase in the frequency of CD3−CD56+CD107a+ NK cells and the frequency of CD3−CD56+16+ NK cells in samples incubated with RTX and OBZ, from patients with RA and SLE.

Horizontal lines represent the median. FIG. 4C shows the relationship between the frequency of CD3−CD56+ CD107a+ NK cells in samples incubated with or without RTX and OBZ in samples from patients with RA (n=18). FIG. 4D shows the relationship between the frequency of CD3−CD56+CD107a+ NK cells in samples incubated with or without RTX and OBZ in samples from patients with SLE (n=23).

FIG. 5A shows a whole blood B-cell depletion assay showing the percentage B-cell depletion by RTX, $OBZ_{Gly}$ and OBZ in samples from patients with RA (n=18) and SLE (n=23). Box and whiskers represent the interquartile range and the range, the horizontal line in the box represents the median. FIG. 5B shows the frequency of CD3−CD56+CD107a+ NK cells in whole blood samples from patients with RA and SLE after 24-hour incubation with or without mAbs, analyzed by flow cytometry. FIG. 5C shows the relative increase in the frequency of CD3−CD56+CD107a+ NK cells in whole blood samples incubated with or without mAbs, analyzed by flow cytometry. FIG. 5D shows the frequency of CD3−CD56+CD16+ NK cells in whole blood samples from patients with RA (n=18) and SLE (n=23) after 24 hour incubation with or without mAbs, analyzed by flow cytometry. For the bar graphs, the error bars represent the median and interquartile ranges. * $p<0.05$; , $p<0.005$; *, $p<0.0001$; and ns, not significant.

FIG. 6A shows the mean fluorescence intensity (MFI) of CD11b on CD15+ neutrophils after 24 hour incubation of whole blood samples from patients with RA (n=10) and SLE (n=22) incubated with or without mAbs (1 μg/ml). The Median and interquartile ranges are represented by the error bars. FIG. 6B shows the relationship between the MFI of CD11b on CD15+ neutrophils in samples incubated with or without mAbs in RA and SLE samples. FIG. 6C shows the MFI of CD62L on CD15+ neutrophils in samples incubated with or without mAbs in RA and SLE samples. FIG. 6D shows the relationship between the MFI of CD62L on CD15+ neutrophils, in samples incubated with or without mAbs in RA (n=10) and SLE (n=22) samples. * $p<0.05$; , $p<0.005$; *, $p<0.0001$. Spearman correlation coefficient, $r^2$ was considered significant when p was at least <0.05.

FIG. 7A shows the frequency of Annexin V+ cells as a proportion of all CD19+ B cells and also B-cell subpopulations based on the relative expression of IgD and CD27: (IgD+CD27− naïve cells; IgD+CD27+ unswitched memory cells; IgD-CD27+ switched memory cells; and IgD-CD27-double negative cells); in samples from patients with RA (n=5) and SLE (n=4) incubated with or without mAbs. FIG. 7B shows the mean fluorescence intensity (MFI) of CD20 on all CD19+ cells and B-cell subpopulations in samples from patients with SLE (n=9). FIG. 7C shows a surface fluorescence-quenching assay. The frequency of surface accessible mAbs after 6 hours of incubation with isolated B-cells, with or without prior incubation with anti-FcγRII mAb, AT10 from patients with SLE (n=9), in all CD19+ B-cells and B-cell subpopulations. FIG. 7D shows the MFI of FcγRIIb on all CD19+ B-cells and B-cell subpopulations in samples from patients with SLE (n=9). For the bar graphs, the error bars represent the median and interquartile ranges. Box and whiskers represent the interquartile range and the horizontal line in the box represents the median. * $p<0.05$; , $p<0.005$; *, $p<0.0001$.

DETAILED DESCRIPTION

Figure 1:
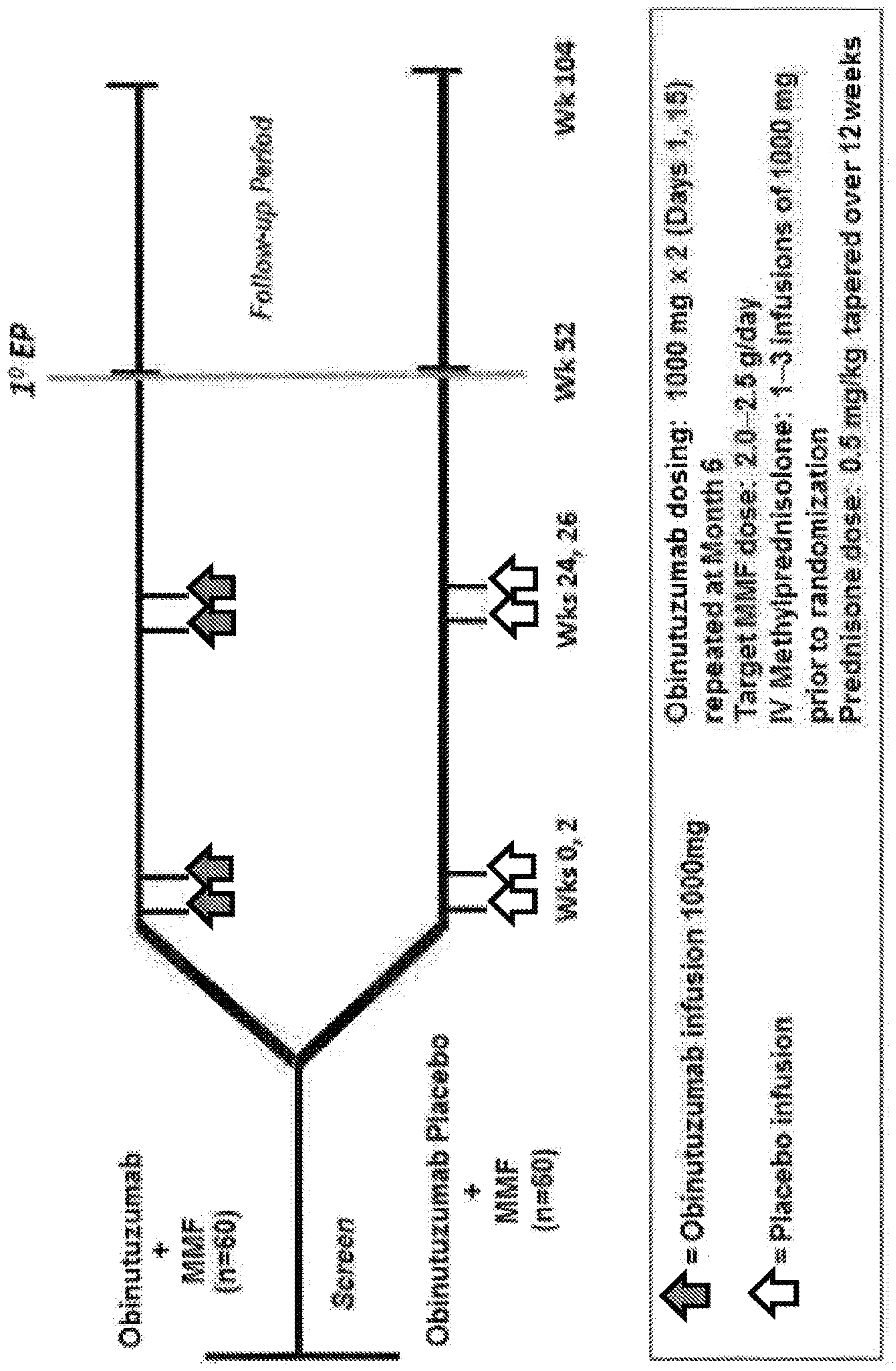
FIG. 1 shows the study design for a Phase II study examining obinutuzumab+mycophenolate mofetil vs. placebo+mycophenolate mofetil. EP=endpoint; MMF=mycophenolate mofetil.

In one aspect, provided herein are methods for treating or delaying progression of lupus nephritis in an individual, including administering to the individual at least a first antibody exposure to a type II anti-CD20 antibody and a second antibody exposure to the type II anti-CD20 antibody. In some embodiments, the individual has lupus. In some embodiments, the second antibody exposure is not provided until from about 18 weeks to about 26 weeks after the first antibody exposure. In some embodiments, the first antibody exposure includes one or two doses of the type II anti-CD20 antibody, the first antibody exposure containing a total exposure of between about 1800 mg and about 2200 mg of the type II anti-CD20 antibody. In some embodiments, the second antibody exposure includes one or two doses of the type II anti-CD20 antibody, the second antibody exposure containing a total exposure of between about 1800 mg and about 2200 mg of the type II anti-CD20 antibody. In some embodiments, the antibody comprises a heavy chain comprising HVR-H1 sequence of SEQ ID NO:1, HVR-H2 sequence of SEQ ID NO:2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO: 6.

In another aspect, provided herein are methods for treating or delaying progression of lupus nephritis in an individual that has lupus, including administering to the individual an effective amount of a type II anti-CD20 antibody.

In some embodiments, the antibody includes a heavy chain containing HVR-H1 sequence of SEQ ID NO: 1, HVR-H2 sequence of SEQ ID NO: 2, and HVR-H3 sequence of SEQ ID NO:3, and a light chain containing HVR-L1 sequence of SEQ ID NO:4, HVR-L2 sequence of SEQ ID NO:5, and HVR-L3 sequence of SEQ ID NO:6. In some embodiments, the individual has class III or class IV lupus nephritis.

In another aspect, provided herein are methods for treating or delaying progression of rheumatoid arthritis (RA) or systemic lupus erythematosus (SLE) in an individual, comprising administering to the individual an effective amount of an anti-CD20 antibody. In some embodiments, the antibody comprises a heavy chain variable region comprising an HVR-H1 sequence of SEQ ID NO: 1, an HVR-H2 sequence of SEQ ID NO:2, and an HVR-H3 sequence of SEQ ID NO:3, and a light chain variable region comprising an HVR-L1 sequence of SEQ ID NO: 4, an HVR-L2 sequence of SEQ ID NO:5, and an HVR-L3 sequence of SEQ ID NO:6.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2*: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); PCR: *The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "lupus nephritis (LN)" refers to a manifestation of lupus (e.g., systemic lupus erythematosus, drug-induced lupus, neonatal lupus, or discoid lupus) in the kidney(s).

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, $F(ab')_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., Hybridoma, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004), and technologies for producing human or human-like antibodies in animals that have parts or all of the human immunoglobulin loci or genes encoding human immunoglobulin sequences (sec, e.g., WO 1998/24893; WO 1996/34096; WO 1996/33735; WO 1991/10741; Jakobovits et al., *Proc. Natl. Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368: 856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', $F(ab')_2$ and Fv fragments; diabodies; linear antibodies (see U.S. U.S. Pat. No. 5,641,870, Example 2; Zapata et al., *Protein Eng.* 8 (10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90:6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147 (1): 86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the $V_H$ (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, NJ, 2003). Indeed, naturally occurring camelid antibodies consisting of a heavy chain only are functional and stable in the absence of light chain. See, e.g., *Hamers-Casterman et al., Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, M D. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82α, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* $5^{th}$ Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVOLVESGG-GLVQPGGSLRLSCAAS (HC-FR1) (SEQ ID NO:35), WVRQAPGKGLEWV (HC-FR2), (SEQ ID NO:36), RFTI-SADTSKNTAYLQMNSLRAEDTAVYYCAR (HC-FR3, SEQ ID NO:37), WGQGTLVTVSA (HC-FR4), (SEQ ID NO:38).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSL-SASVGDRVTITC (LC-FR1) (SEQ ID NO:39), WYQQKPGKAPKLLIY (LC-FR2) (SEQ ID NO:40), GVPSRFSGSGSGTDFTLTISSLQPEDFATYYC (LC-FR3) (SEQ ID NO:41), FGQGTKVEIKR (LC-FR4) (SEQ ID NO:42).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154 (7): 3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117:587 (1976) and Kim et al., *J. Immunol.* 24:249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9 (2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with lupus nephritis are mitigated or eliminated, including, but are not limited to, elevated serum creatinine, proteinuria, red cell casts, reduced renal function, nephrotic syndrome, granular casts, microhematuria, macrohematuria, hypertension, tubular abnormalities, hyperkalemia, rapidly progressive glomerulonephritis (RPGN), and acute renal failure (ARF).

As used herein, "delaying progression" of a disease (e.g., lupus nephritis) means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual, e.g., an individual at risk for developing the disease, does not develop the disease. For example, the progression of SLE in an individual before the onset of LN symptoms and/or pathology may be delayed such that the development of LN is postponed or prevented.

As used herein, "complete renal response (CRR)" refers to a response to treatment that includes a normalization of serum creatinine, inactive urinary sediment, and a urinary protein to creatinine ratio of less than 0.5.

As used herein, "partial renal response (PRR)" refers to a response to treatment that is less than a CRR but still includes mitigation of one or more symptoms including without limitation a reduction in serum creatinine, reduced urinary sediment, and a reduction in proteinuria.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of lupus nephritis, an effective amount of the drug may have the effect in and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

"CD20" as used herein refers to the human B-lymphocyte antigen CD20 (also known as CD20, B-lymphocyte surface antigen B1, Leu-16, Bp35, BM5, and LF5; the sequence is characterized by the SwissProt database entry P11836) is a hydrophobic transmembrane protein with a molecular weight of approximately 35 kD located on pre-B and mature B lymphocytes. (Valentine, M. A., et al., *J. Biol. Chem.* 264 (19) (1989 11282-11287; Tedder, T. F., et al, *Proc. Natl. Acad. Sci. U.S.A.* 85 (1988) 208-12; Stamenkovic, I., et al., *J. Exp. Med.* 167 (1988) 1975-80; Einfeld, D. A., et al., *EMBO J.* 7 (1988) 711-7; Tedder, T. F., et al., *J. Immunol.* 142 (1989) 2560-8). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: Cell death/apoptosis induction, ADCC and CDC.

Synonyms of CD20, as recognized in the art, include B-lymphocyte antigen CD20, B-lymphocyte surface antigen B1, Leu-16, Bp35, BM5, and LF5.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., *Blood* 103 (2004) 2738-2743; and Cragg, M. S., et al., *Blood* 101 (2003) 1045-1052, see Table 1 below.

TABLE 1

Properties of type I and type II anti-CD20 antibodies

| Type I anti-CD20 antibodies | type II anti-CD20 antibodies |
|---|---|
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

Examples of type II anti-CD20 antibodies include e.g. humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype.

Examples of type I anti-CD20 antibodies include e.g. rituximab, HI47 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312).

The afucosylated anti-CD20 antibodies according to the invention are preferably type II anti-CD20 antibodies, more preferably afucosylated humanized B-Ly1 antibodies as described in WO 2005/044859 and WO 2007/031875.

The "rituximab" antibody (reference antibody; example of a type I anti-CD20 antibody) is a genetically engineered chimeric human gamma 1 murine constant domain containing monoclonal antibody directed against the human CD20 antigen. However this antibody is not glycoengineered and not afucosylates and thus has an amount of fucose of at least 85%. This chimeric antibody contains human gamma 1 constant domains and is identified by the name "C2B8" in U.S. Pat. No. 5,736,137 (Andersen, et. al.) issued on Apr. 17, 1998, assigned to IDEC Pharmaceuticals Corporation. Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff, M. E., et. al, *Blood* 83 (2) (1994) 435-445). Additionally, it exhibits activity in assays that measure antibody-dependent cellular cytotoxicity (ADCC).

The term "GA101 antibody" as used herein refers to any one of the following antibodies that bind human CD20: (1) an antibody comprising an HVR-H1 comprising the amino acid sequence of SEQ ID NO:1, an HVR-H2 comprising the amino acid sequence of SEQ ID NO: 2, an HVR-H3 comprising the amino acid sequence of SEQ ID NO:3, an HVR-L1 comprising the amino acid sequence of SEQ ID NO:4, an HVR-L2 comprising the amino acid sequence of SEQ ID NO:5, and an HVR-L3 comprising the amino acid sequence of SEQ ID NO: 6; (2) an antibody comprising a $V_H$ domain comprising the amino acid sequence of SEQ ID NO: 7 and a $V_L$ domain comprising the amino acid sequence of SEQ ID NO:8, (3) an antibody comprising an amino acid sequence of SEQ ID NO:9 and an amino acid sequence of SEQ ID NO: 10; (4) an antibody known as obinutuzumab, or (5) an antibody that comprises an amino acid sequence that has at least 95%, 96%, 97%, 98% or 99% sequence identity with amino acid sequence of SEQ ID NO:9 and that comprises an amino acid sequence that has at least 95%, 96%, 97%, 98% or 99% sequence identity with an amino acid sequence of SEQ ID NO:10. In one embodiment, the GA101 antibody is an IgG1 isotype antibody. In some embodiments, the anti-CD20 antibody is a humanized B-Ly1 antibody.

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain ($V_H$): SEQ ID NO: 11; variable region of the murine light chain ($V_L$): SEQ ID NO: 12-see Poppema, S. and Visser, L., *Biotest Bulletin* 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

```
Variable region of the murine monoclonal anti-CD20 antibody B-Ly1 heavy chain (VH)
                                                                     (SEQ ID NO: 11)
Gly Pro Glu Leu Val Lys Pro Gly Ala Ser Val Lys Ile Ser Cys Lys
 1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

Variable region of the murine monoclonal anti-CD20 antibody B-Ly1 light chain (VL)
                                                                     (SEQ ID NO: 12)
Asn Pro Val Thr Leu Gly Thr Ser Ala Ser Ile Ser Cys Arg Ser Ser
 1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
            100
```

In one embodiment, the "humanized B-Ly1 antibody" has variable region of the heavy chain (VH) selected from group of SEQ ID NO:7, 8, and 13 to 33 (corresponding to, inter alia, B-HH2 to B-HH9 and B-HL8 to B-HL17 of WO 2005/044859 and WO 2007/031875). In one specific embodiment, such variable domain is selected from the group consisting of SEQ ID NOS: 14, 15, 7, 19, 25, 27, and 29 (corresponding to B-HH2, BHH-3, B-HH6, B-HH8, B-HL8, B-HL11 and B-HL13 of WO 2005/044859 and WO 2007/031875). In one specific embodiment, the "humanized B-Ly1 antibody" has variable region of the light chain (VL) of SEQ ID NO:8 (corresponding to B-KV1 of WO 2005/044859 and WO 2007/031875). In one specific embodiment, the "humanized B-Ly1 antibody" has a variable region of the heavy chain (VH) of SEQ ID NO:7 (corresponding to B-HH6 of WO 2005/044859 and WO 2007/031875) and a variable region of the light chain (VL) of SEQ ID NO:8 (corresponding to B-KV1 of WO 2005/044859 and WO 2007/031875). Furthermore in one embodiment, the humanized B-Ly1 antibody is an IgG1 antibody. According to the invention such afucosylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the afucosylated glyco-engineered humanized B-Ly1 is B-HH6-B-KV1 GE. In one embodiment, the anti-CD20 antibody is obinutuzumab (recommended INN, WHO Drug Information, Vol. 26, No. 4, 2012, p. 453). As used herein, obinutuzumab is synonymous for GA101 or RO5072759. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In some embodiments, the humanized B-Ly1 antibody is an antibody comprising a heavy chain comprising the amino acid sequence of SEQ ID NO:9 and a light chain comprising the amino acid sequence of SEQ ID NO: 10 or an antigen-binding fragment thereof. In some embodiments, the humanized B-Ly1 antibody comprises a heavy chain variable region comprising the three heavy chain CDRs of SEQ ID NO:9 and a light chain variable region comprising the three light chain CDRs of SEQ ID NO:10.

```
Heavy chain
                                                     (SEQ ID NO: 9)
QVQLVQSGAE VKKPGSSVKV SCKASGYAFS YSWINWVRQA PGQGLEWMGR     50

IFPGDGDTDY NGKFKGRVTI TADKSTSTAY MELSSLRSED TAVYYCARNV    100

FDGYWLVYWG QGTLVTVSSA STKGPSVFPL APSSKSTSGG TAALGCLVKD    150

YFPEPVTVSW NSGALTSGVH TFPAVLQSSG LYSLSSVVTV PSSSLGTQTY    200

ICNVNHKPSN TKVDKKVEPK SCDKTHTCPP CPAPELLGGP SVFLFPPKPK    250

DTLMISRTPE VTCVVVDVSH EDPEVKFNWY VDGVEVHNAK TKPREEQYNS    300

TYRVVSVLTV LHQDWLNGKE YKCKVSNKAL PAPIEKTISK AKGQPREPQV    350

YTLPPSRDEL TKNQVSLTCL VKGFYPSDIA VEWESNGQPE NNYKTTPPVL    400

DSDGSFFLYS KLTVDKSRWQ QGNVFSCSVM HEALHNHYTQ KSLSLSPG      449

Light chain
                                                     (SEQ ID NO: 10)
DIVMTQTPLS LPVTPGEPAS ISCRSSKSLL HSNGITYLYW YLQKPGQSPQ     50

LLIYQMSNLV SGVPDRFSGS GSGTDFTLKI SRVEAEDVGV YYCAQNLELP    100

YTFGGGTKVE IKRTVAAPSV FIFPPSDEQL KSGTASVVCL LNNFYPREAK    150

VQWKVDNALQ SGNSQESVTE QDSKDSTYSL SSTLILSKAD YEKHKVYACE    200

VTHQGLSSPV TKSFNRGEC                                      219
```

In some embodiments, the humanized B-Ly1 antibody is an afucosylated glyco-engineered humanized B-Ly1. Such glycoengineered humanized B-Ly1 antibodies have an altered pattern of glycosylation in the Fc region, preferably having a reduced level of fucose residues. Preferably the amount of fucose is 60% or less of the total amount of oligosaccharides at Asn297 (in one embodiment the amount of fucose is between 40% and 60%, in another embodiment the amount of fucose is 50% or less, and in still another embodiment the amount of fucose is 30% or less). Furthermore the oligosaccharides of the Fc region are preferably bisected. These glycoengineered humanized B-Ly1 antibodies have an increased ADCC.

The "ratio of the binding capacities to CD20 on Raji cells (ATCC-No. CCL-86) of an anti-CD20 antibodies compared to rituximab" is determined by direct immunofluorescence measurement (the mean fluorescence intensities (MFI) is measured) using said anti-CD20 antibody conjugated with Cy5 and rituximab conjugated with Cy5 in a FACSArray (Becton Dickinson) with Raji cells (ATCC-No. CCL-86), as described in Example No. 2, and calculated as follows:

$$\text{Ratio of the binding capacities to } CD20 \text{ on Raji cells } (ATCC\text{-}No.\ CCL\text{-}86) = \frac{MFI(Cy5\text{-anti}-CD20 \text{ antibody})}{MFI(Cy5\text{-rituximab})} \times \frac{Cy5\text{-labeling ratio } (Cy5\text{-rituximab})}{Cy5\text{-labeling ratio } (Cy5\text{-anti}-CD20 \text{ antibody})}$$

MFI is the mean fluorescent intensity. The "Cy5-labeling ratio" as used herein means the number of Cy5-label molecules per molecule antibody.

Typically said type II anti-CD20 antibody has a ratio of the binding capacities to CD20 on Raji cells (ATCC-No. CCL-86) of said second anti-CD20 antibody compared to rituximab of 0.3 to 0.6, and in one embodiment, 0.35 to 0.55, and in yet another embodiment, 0.4 to 0.5.

In one embodiment said type II anti-CD20 antibody, e.g., a GA101 antibody, has increased antibody dependent cellular cytotoxicity (ADCC).

By "antibody having increased antibody dependent cellular cytotoxicity (ADCC)", it is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5\times10^6$ cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of $^{51}Cr$, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (VN) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at 50×g for 1 minute and incubated for 1 hour at 4° C.;
   viii) 50 microliters of the PBMC suspension (point i above) are added to each well to yield an effector: target cell ratio of 25:1 and the plates are placed in an incubator under 5% CO2 atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point V above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. In one embodiment, the increase in ADCC is relative to the ADCC, measured with the above assay, mediated by the same antibody, produced by the same type of host cells, using the same standard production, purification, formulation and storage methods, which are known to those skilled in the art, except that the comparator antibody (lacking increased ADCC) has not been produced by host cells engineered to overexpress GnTIII and/or engineered to have reduced expression from the fucosyltransferase 8 (FUT8) gene (e.g., including, engineered for FUT8 knock out).

Said "increased ADCC" can be obtained by, for example, mutating and/or glycoengineering of said antibodies. In one embodiment, the antibody is glycoengineered to have a biantennary oligosaccharide attached to the Fc region of the antibody that is bisected by GlcNAc, e.g., in WO 2003/011878 (Jean-Mairet et al.); U.S. Pat. No. 6,602,684 (Umana et al.); US 2005/0123546 (Umana et al.), Umana, P., et al., Nature Biotechnol. 17 (1999) 176-180). In another embodiment, the antibody is glycoengineered to lack fucose on the carbohydrate attached to the Fc region by expressing the antibody in a host cell that is deficient in protein fucosylation (e.g., Lec13 CHO cells or cells having an alpha-1,6-fucosyltransferase gene (FUT8) deleted or the FUT gene expression knocked down (see, e.g., Yamane-Ohnuki et al. Biotech. Bioeng. 87:614 (2004); Kanda, Y. et al., Biotechnol. Bioeng., 94 (4): 680-688 (2006); and WO2003/085107). In yet another embodiment, the antibody sequence has been engineered in its Fc region to enhance ADCC (e.g., in one embodiment, such engineered antibody variant comprises an Fc region with one or more amino acid substitutions at positions 298, 333, and/or 334 of the Fc region (EU numbering of residues)).

The term "complement-dependent cytotoxicity (CDC)" refers to lysis of human tumor target cells by the antibody according to the invention in the presence of complement. CDC can be measured by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. In one embodiment, the assay is performed with $^{51}Cr$ or Eu labeled tumor cells and measurement of released $^{51}Cr$ or Eu. Controls include the incubation of the tumor target cells with complement but without the antibody.

The term "expression of the CD20" antigen is intended to indicate a significant level of expression of the CD20 antigen in a cell, e.g., a T- or B-Cell. In one embodiment, patients to be treated according to the methods of this invention express significant levels of CD20 on a B-cell. CD20 expression on a B-cell can be determined by standard assays known in the art. e.g., CD20 antigen expression is measured using immunohistochemical (IHC) detection, FACS or via PCR-based detection of the corresponding mRNA.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

III. Methods

In one aspect, provided herein are methods for treating or delaying progression of lupus nephritis in an individual that has lupus by administering an effective amount of a type II anti-CD20 antibody. In some embodiments, the individual has or is at risk for developing lupus nephritis. In some embodiments, the lupus nephritis is class III or class IV lupus nephritis. In some embodiments, the methods include administering to the individual at least a first antibody exposure to a type II anti-CD20 antibody and a second antibody exposure to the type II anti-CD20 antibody, the second antibody exposure not being provided until from about 18 weeks to about 26 weeks after the first antibody exposure; wherein the first antibody exposure comprises one or two doses of the type II anti-CD20 antibody, the first antibody exposure comprising a total exposure of between about 1800 mg and about 2200 mg of the type II anti-CD20 antibody; and wherein the second antibody exposure comprises one or two doses of the type II anti-CD20 antibody, the second antibody exposure comprising a total exposure of between about 1800 mg and about 2200 mg of the type II anti-CD20 antibody. As described below, in some embodiments, the antibody comprises a heavy chain comprising HVR-H1 sequence of SEQ ID NO: 1, HVR-H2 sequence of SEQ ID NO:2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO:6. In some embodiments, the antibody comprises a $V_H$ domain comprising the amino acid sequence of SEQ ID NO:7 and a $V_L$ domain comprising the amino acid sequence of SEQ ID NO:8. In some embodiments, the antibody comprises an amino acid sequence of SEQ ID NO:9 and an amino acid sequence of SEQ ID NO: 10. In some embodiments, the antibody comprises an antibody that comprises an amino acid sequence that has at least 95%, 96%, 97%, 98% or 99% sequence identity with amino acid sequence of SEQ ID NO: 9 and that comprises an amino acid sequence that has at least 95%, 96%, 97%, 98% or 99% sequence identity with an amino acid sequence of SEQ ID NO:10.

Anti-CD20 Antibodies

Certain aspects of the present disclosure relate to anti-CD20 antibodies, e.g., for use in methods for treating or preventing progression of lupus nephritis. In some embodiments, the anti-CD20 antibody is a type II antibody. In some embodiments, the anti-CD20 antibody is human or humanized. In some embodiments, the anti-CD20 antibody is afucosylated. In some embodiments, the anti-CD20 antibody is a GA101 antibody.

Examples of type II anti-CD20 antibodies include e.g. humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype.

Examples of type I anti-CD20 antibodies include e.g. rituximab, HI47 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312).

In some embodiments, the anti-CD20 antibody is a GA101 antibody described herein. In some embodiments, the anti-CD20 is any one of the following antibodies that bind human CD20: (1) an antibody comprising an HVR-H1 comprising the amino acid sequence of GYAFSY (SEQ ID NO:1), an HVR-H2 comprising the amino acid sequence of FPGDGDTD (SEQ ID NO:2), an HVR-H3 comprising the amino acid sequence of NVFDGYWLVY (SEQ ID NO: 3), an HVR-L1 comprising the amino acid sequence of RSSKSLLHSNGITYLY (SEQ ID NO: 4), an HVR-L2 comprising the amino acid sequence of QMSNLVS (SEQ ID NO:5), and an HVR-L3 comprising the amino acid sequence of AQNLELPYT (SEQ ID NO:6); (2) an antibody comprising a VH domain comprising the amino acid sequence of SEQ ID NO:7 and a VL domain comprising the amino acid sequence of SEQ ID NO:8, (3) an antibody comprising an amino acid sequence of SEQ ID NO:9 and an amino acid sequence of SEQ ID NO:10; (4) an antibody known as obinutuzumab, or (5) an antibody that comprises an amino acid sequence that has at least 95%, 96%, 97%, 98% or 99% sequence identity with amino acid sequence of SEQ ID NO: 9 and that comprises an amino acid sequence that has at least 95%, 96%, 97%, 98% or 99% sequence identity with an amino acid sequence of SEQ ID NO:10. In one embodiment, the GA101 antibody is an IgG1 isotype antibody. In some embodiments, the anti-CD20 antibody comprises an HVR-H1, HVR-H2, HVR-H3, HVR-L1, HVR-L2, and HVR-L3 of any of the antibodies described herein, e.g., 3 HVRs from SEQ ID NO:7 and 3 HVRs from SEQ ID NO:8, 3 HVRs from SEQ ID NO:9 and 3 HVRs from SEQ ID NO:10, or any HVRs of the amino acid sequences provided in Table 2.

In some embodiments, the anti-CD20 antibody comprises a heavy chain variable region (VH) comprising the amino acid sequence of SEQ ID NO:7, and a light chain variable region (VL) comprising the amino acid sequence of SEQ ID NO:8.

(SEQ ID NO: 7)

QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSS (SEQ ID NO: 8)

DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYC

AQNLELPYTFGGGTKVEIKRTV.

In some embodiments, the anti-CD20 antibody comprises a heavy chain comprising the amino acid sequence of SEQ ID NO:9, and a light chain comprising the amino acid sequence of SEQ ID NO:10.

(SEQ ID NO: 9)

QVQLVQSGAEVKKPGSSVKVSCKAS*GYAFSY*

SWINWVRQAPGQGLEWMGRI*FPGDGDTD*YNGK

FKGRVTITADKSTSTAYMELSSLRSEDTAVY

YCAR*NVFDGYWLVY*WGQGTLVTVSSASTKG

PSVFPLAPSSKSTSGGTAALGCLVKDYFPEP

VTVSWNSGALTSGVHTFPAVLQSSGLYSLSS

VVTVPSSSLGTQTYICNVNHKPSNTKVDKKV

EPKSCDKTHTCPPCPAPELLGGPSVFLFPPK

PKDTLMISRTPEVTCVVVDVSHEDPEVKFNW

YVDGVEVHNAKTKPREEQYNSTYRVVSVLTV

LHQDWLNGKEYKCKVSNKALPAPIEKTISKA

KGQPREPQVYTLPPSRDELTKNQVSLTCLVK

GFYPSDIAVEWESNGQPENNYKTTPPVLDSD

GSFFLYSKLTVDKSRWQQGNVFSCSVMHEAL

HNHYTQKSLSLSPG (SEQ ID NO: 10)

DIVMTQTPLSLPVTPGEPASISC*RSSKSLLH*

*SNGITYLY*WYLQKPGQSPQLLIY*QMSNLVS*G

VPDRFSGSGSGTDFTLKISRVEAEDVGVYYC

*AQNLELPYT*FGGGTKVEIKRTVAAPSVFIFP

PSDEQLKSGTASVVCLLNNFYPREAKVQWKV

-continued

DNALQSGNSQESVTEQDSKDSTYSLSSTLTL

SKADYEKHKVYACEVTHQGLSSPVTKSFNRG

EC

In some embodiments, the anti-CD20 antibody is a humanized B-Ly1 antibody. In some embodiments, the humanized B-Ly1 antibody comprises a heavy chain variable region comprising the three heavy chain CDRs of SEQ ID NO:9 and a light chain variable region comprising the three light chain CDRs of SEQ ID NO:10. In some embodiments, the humanized B-Ly1 antibody comprises a heavy chain comprising the sequence of SEQ ID NO:9 and a light chain comprising the sequence of SEQ ID NO:10.

In some embodiments, the anti-CD20 antibody comprises an amino acid sequence at least 80%, 85%, 90%, 95%, 96%, 97%, 98% or 99% identical to a polypeptide sequence listed in Table 2 below.

TABLE 2

Polypeptide sequences.

| CONSTRUCT | POLYPEPTIDE SEQUENCE | SEQ ID NO |
|---|---|---|
| B-HH1 | QVQLVQSGAEVKKPGSSVKVSCKASGYTFSYSWM SWVRQAPGQGLEWMGRIFPGDGDTDYAQKFQGRV TITADKSTSTAYMELSSLRSEDTAVYYCARNVFDG YWLVYWGQGTLVTVSS | 13 |
| B-HH2 | QVQLVQSGAEVKKPGSSVKVSCKASGYAFSYSWM NWVRQAPGQGLEWMGRIFPGDGDTDYNGKFKGR VTITADKSTSTAYMELSSLRSEDTAVYYCARNVFD GYWLVYWGQGTLVTVSS | 14 |
| B-HH3 | QVQLVQSGAEVKKPGSSVKVSCKASGYAFSYSWM NWVRQAPGQGLEWMGRIFPGDGDTDYNGKFKGR VTITADKSTSTAYMELSSLRSEDTAVYLCARNVFDG YWLVYWGQGTLVTVSS | 15 |
| B-HH4 | QVQLVQSGAEVKKPGASVKVSCKVSGYAFSYSWM NWVRQAPGQGLEWMGRIFPGDGDTDYNGKFKGR VTITADKSTSTAYMELSSLRSEDTAVYYCARNVFD GYWLVYWGQGTLVTVSS | 16 |
| B-HH5 | QVQLVQSGAEVKKPGSSVKVSCKASGYAFSYSWM SWVRQAPGQGLEWMGRIFPGDGDTDYNGKFKGRV TITADKSTSTAYMELSSLRSEDTAVYYCARNVFDG YWLVYWGQGTLVTVSS | 17 |
| B-HH6 | QVQLVQSGAEVKKPGSSVKVSCKASGYAFSYSWIN WVRQAPGQGLEWMGRIFPGDGDTDYNGKFKGRVT ITADKSTSTAYMELSSLRSEDTAVYYCARNVFDGY WLVYWGQGTLVTVSS | 7 |
| B-HH7 | QVQLVQSGAEVKKPGSSVKVSCKASGYAFSYSWIS WVRQAPGQGLEWMGRIFPGDGDTDYNGKFKGRVT ITADKSTSTAYMELSSLRSEDTAVYYCARNVFDGY WLVYWGQGTLVTVSS | 18 |
| B-HH8 | QVQLVQSGAEVKKPGASVKVSCKASGYTFTYSWM NWVRQAPGQGLEWMGRIFPGDGDTDYNGKFKGR VTITADKSTSTAYMELSSLRSEDTAVYYCARNVFD GYWLVYWGQGTLVTVSS | 19 |
| B-HH9 | QVQLVQSGAEVKKPGASVKVSCKASGYTFSYSWM NWVRQAPGQGLEWMGRIFPGDGDTDYNGKFKGR VTITADKSTSTAYMELSSLRSEDTAVYYCARNVFD GYWLVYWGQGTLVTVSS | 20 |

TABLE 2-continued

Polypeptide sequences.

| CONSTRUCT | POLYPEPTIDE SEQUENCE | SEQ ID NO |
|---|---|---|
| B-HL1 | QVQLVQSGAEVKKPGASVKVSCKASGYTFTYSWM HWVRQAPGQGLEWMGRIFPGDGDTDYAQKFQGR VTMTRDTSTSTVYMELSSLRSEDTAVYYCARNVFD GYWLVYWGQGTLVTVSS | 21 |
| B-HL2 | EVQLVQSGAEVKKPGATVKISCKVSGYTFTYSWMH WVQQAPGKGLEWMGRIFPGDGDTDYAEKFQGRVT ITADTSTDTAYMELSSLRSEDTAVYYCATNVFDGY WLVYWGQGTLVTVSS | 22 |
| B-HL3 | EVQLVQSGAEVKKPGATVKISCKVSGYTFTYSWMN WVQQAPGKGLEWMGRIFPGDGDTDYNGKFKGRVT ITADTSTDTAYMELSSLRSEDTAVYYCATNVFDGY WLVYWGQGTLVTVSS | 23 |
| B-HL4 | QMQLVQSGAEVKKTGSSVKVSCKASGYTFTYSWM SWVRQAPGQGLEWMGRIFPGDGDTDYAQKFQGRV TITADKSTSTAYMELSSLRSEDTAVYYCARNVFDG YWLVYWGQGTLVTVSS | 24 |
| B-HL8 | EVQLVESGGGLVKPGGSLRLSCAASGFTFSYSWMN WVRQAPGKGLEWVGRIFPGDGDTDYNGKFKGRVT ITADKSTSTAYMELSSLRSEDTAVYYCARNVFDGY WLVYWGQGTLVTVSS | 25 |
| B-HL10 | EVQLVESGGGLVKPGGSLRLSCAASGFAFSYSWMN WVRQAPGKGLEWVGRIFPGDGDTDYNGKFKGRVT ITADKSTSTAYMELSSLRSEDTAVYYCARNVFDGY WLVYWGQGTLVTVSS | 26 |
| B-HL11 | QVQLVESGGGLVKPGGSLRLSCAASGFTFSYSWMN WVRQAPGKGLEWVGRIFPGDGDTDYNGKFKGRVT ITADKSTSTAYMELSSLRSEDTAVYYCARNVFDGY WLVYWGQGTLVTVSS | 27 |
| B-HL12 | EVQLVESGAGLVKPGGSLRLSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 28 |
| B-HL13 | EVQLVESGGGVVKPGGSLRLSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 29 |
| B-HL14 | EVQLVESGGGLKKPGGSLRLSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 30 |
| B-HL15 | EVQLVESGGGLVKPGSSLRLSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 31 |
| B-HL16 | EVQLVESGGGLVKPGGSLRVSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 32 |
| B-HL17 | EVQLVESGGGLVKPGGSLRLSCAASGFTFSYSWMN WVRQAPGKGLEWMGRIFPGDGDTDYNGKFKGRVT ITADKSTSTAYMELSSLRSEDTAVYYCARNVFDGY WLVYWGQGTLVTVSS | 33 |
| VH Signal Sequence | MDWTWRILFLVAAATGAHS | 34 |
| B-KV1 | DIVMTQTPLSLPVTPGEPASISCRSSKSLLHSNGIT YLYWYLQKPGQSPQLLIYQMSNLVSGVPDRFSGSGS GTDFTLKISRVEAEDVGVYYCAQNLELPYTFGGGTK VEIKRTV | 8 |

TABLE 2-continued

Polypeptide sequences.

| CONSTRUCT | POLYPEPTIDE SEQUENCE | SEQ ID NO |
|---|---|---|
| VL Signal Sequence | MDMRVPAQLLGLLLLWFPGARC | 43 |

In some embodiments, the anti-CD20 antibody (e.g., a type II anti-CD20 antibody) is an afucosylated glyco-engineered antibody. Such glycoengineered antibodies have an altered pattern of glycosylation in the Fc region, preferably having a reduced level of fucose residues. Preferably the amount of fucose is 60% or less of the total amount of oligosaccharides at Asn297 (in one embodiment the amount of fucose is between 40% and 60%, in another embodiment the amount of fucose is 50% or less, and in still another embodiment the amount of fucose is 30% or less). Furthermore the oligosaccharides of the Fc region are preferably bisected. These glycoengineered humanized anti-CD20 (e.g., B-Ly1) antibodies have an increased ADCC.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins, N., et al., *Nature Biotechnol.* 14 (1996) 975-81).

Mammalian cells are the preferred hosts for production of therapeutic glycoproteins, due to their capability to glycosylate proteins in the most compatible form for human application. (Cumming, D. A., et al., *Glycobiology* 1 (1991) 115-30; Jenkins, N., et al., *Nature Biotechnol.* 14 (1996) 975-81). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum free media, and permit the development of safe and reproducible bioprocesses. Other commonly used animal cells include baby hamster kidney (BHK) cells, NSO- and SP2/0-mouse myeloma cells. More recently, production from transgenic animals has also been tested. (Jenkins, N., et al., *Nature Biotechnol.* 14 (1996) 975-981).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15 (1997) 26-32). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15 (1997) 26-32). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R., et al., *Glycobiology* 5 (8) (1995) 813-22).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P., et al., *Nature Biotechnol.* 17 (1999) 176-180 and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5 (1995) 813-822; Jefferis, R., et al., *Immunol. Rev.* 163 (1998) 59-76; Wright, A., and Morrison, S. L., *Trends Biotechnol.* 15 (1997) 26-32).

It was previously shown that overexpression in Chinese hamster ovary (CHO) cells of β (1,4)-N-acetylglucosaminyltransferase 111 ("GnTII17y), a glycosyltransferase catalyzing the formation of bisected oligosaccharides, significantly increases the in vitro ADCC activity of an antineuroblastoma chimeric monoclonal antibody (chCE7) produced by the engineered CHO cells. (See Umana, P., et al., *Nature Biotechnol.* 17 (1999) 176-180; and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umana, P., et al., *Nature Biotechnol.* 17 (1999) 176-180). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

In some embodiments, the anti-CD20 antibody (e.g., a type II anti-CD20 antibody) comprises a human Fc region (e.g., a human IgG1 Fc region). In some embodiments, the Fc region comprises an N-linked oligosaccharide that has been modified. In some embodiments, the N-linked oligosaccharides of the Fc region have reduced fucose residues as compared to an antibody with non-modified N-linked oligosaccharides. In some embodiments, the bisected oligosaccharide is a bisected complex oligosaccharide. In some embodiments, the N-linked oligosaccharides have been modified to have increased bisected, nonfucosylated oligosaccharides. In some embodiments, the bisected, nonfucosylated oligosaccharides are the hybrid type. In some embodiments, the bisected, nonfucosylated oligosaccharides are the complex type. For more detailed description, see, e.g., WO 2003/011878 (Jean-Mairet et al.); U.S. Pat. No. 6,602,684 (Umana et al.); US 2005/0123546 (Umana et al.); and U.S. Pat. No. 8,883,980 (Umana et al.).

In some embodiments, the anti-CD20 antibody (e.g., a type II anti-CD20 antibody) is a multispecific antibody or a bispecific antibody.

Antibody Preparation

An antibody according to any of the above embodiments (e.g., a type II anti-CD20 antibody of the present disclosure) may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to 10-13 M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN- 20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90:6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5:368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133:3001 (1984); Brodeur et al., *Monoclonal Antibody Production Techniques and Applications*, pp. 51-63 (Marcel Dekker, Inc., New York, 1987); and Boerner et al., *J. Immunol.,* 147:86 (1991).) Human antibodies generated via human B-cell hybridoma technology are also described in Li et al., *Proc. Natl. Acad. Sci. USA.* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26 (4): 265-268 (2006) (describing human-human hybridomas). Human hybridoma technology (Trioma technology) is also described in Vollmers and Brandlein, *Histology and Histopathology,* 20 (3): 927-937 (2005) and Vollmers and Brandlein, *Methods and Findings in Experimental and Clinical Pharmacology,* 27 (3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352:624-628 (1991); Marks et al., *J. Mol. Biol.* 222:581-597 (1992); Marks and Bradbury, in *Methods in Molecular Biology* 248:161-175 (Lo, ed., Human Press, Totowa, NJ, 2003); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CD20 and the other is for any other antigen. In certain embodiments, bispecific antibodies may bind to two different epitopes of CD20. Bispecific antibodies may also be used to localize cytotoxic agents to cells which express CD20. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305:537 (1983)), WO 93/08829, and Traunecker et al., *EMBO J.* 10:3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229:81 (1985)); using leucine zippers to produce bi-specific antibodies (see, e.g., Kostelny et al., *J. Immunol.,* 148 (5): 1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147:60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to CD20 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant $V_H$ and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. Sec, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.,* 94 (4): 680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express Fc (RI, Fc (RII and Fc (RIII. FcR expression on hematopoietic cells is summarized in Table 3 on of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18 (12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, the Fc variants described herein further comprise one or more amino acid modifications for attenuating effector function (such as CDC and/or ADCC). In exemplary embodiments, the modification to attenuate effector function is a modification that does not alter the glycosylation pattern of the Fc region. In certain embodiments, the modification to attenuate effector function reduces or eliminates binding to human effector cells, binding to one or more Fc receptors, and/or binding to cells expressing an Fc receptor. In an exemplary embodiment, the Fc variants described herein comprise the following modifications: L234A, L235A and P329G in the Fc region of human IgG1, that result in attenuated effector function. Substitutions L234A, L235A, and P329G (the L234A/L235A/P329G triple variant is referred to as LALAPG) have previously been shown to reduce binding to Fc receptors and complement (see e.g., US Publication No. 2012/0251531).

In various embodiments, Fc variants having reduced effector function refer to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wild-type Fc region (e.g., an Fc region not having a mutation to reduce effector function, although it may have other mutations). In certain embodiments, Fc variants having reduced effector function refer to Fc variants that eliminate all detectable effector function as compared to a wild-type Fc region. Assays for measuring effector function are known in the art and described below.

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity). The primary cells for mediating ADCC, NK cells, express FcγRIII only, whereas monocytes express FcγRI, FcγRII and FcγRIII. FcR expression on hematopoietic cells is summarized in Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)).

Certain antibody variants with improved or diminished binding to FcRs are described. (See, e.g., U.S. Pat. No. 6,737,056; WO 2004/056312, and Shields et al., *J. Biol. Chem.* 9 (2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164:4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102:11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

A. Recombinant Methods and Compositions

Antibodies may be produced using recombinant methods and compositions, e.g., as described in U.S. Pat. No. 4,816,567. In one embodiment, isolated nucleic acid encoding an anti-CD20 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD20 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD20 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B.K.C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, NJ), pp. 255-268 (2003).

B. Assays

Anti-CD20 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc. CD20 binding may be determined using methods known in the art and exemplary methods are disclosed herein. In one embodiment, binding is measured using radioimmunoassay. An exemplary radioimmunoassay is provided below. CD20 antibody is iodinated, and competition reaction mixtures are prepared containing a fixed concentration of iodinated antibody and decreasing concentrations of serially diluted, unlabeled CD20 antibody. Cells expressing CD20 (e.g., BT474 cells stably transfected with human CD20) are added to the reaction mixture. Following an incubation, cells are washed to separate the free iodinated CD20 antibody from the CD20 antibody bound to the cells. Level of bound iodinated CD20 antibody is determined, e.g., by counting radioactivity associated with cells, and binding affinity determined using standard methods. In another embodiment, ability of CD20 antibody to bind to surface-expressed CD20 (e.g., on B cell subsets) is assessed using flow cytometry. Peripheral white blood cells are obtained (e.g., from human, cynomolgus monkey, rat or mouse) and cells are blocked with serum. Labeled CD20 antibody is added in serial dilutions, and T cells are also stained to identify T cell subsets (using methods known in the art). Following incubation of the samples and washing, the cells are sorted using flow cytometer, and data analyzed using methods well known in the art. In another embodiment, CD20 binding may be analyzed using surface plasmon resonance. An exemplary surface plasmon resonance method is exemplified in the Examples.

In another aspect, competition assays may be used to identify an antibody that competes with any of the anti-CD20 antibodies disclosed herein for binding to CD20. In certain embodiments, such a competing antibody binds to the same epitope (e.g., a linear or a conformational epitope) that is bound by any of the anti-CD20 antibodies disclosed herein. Detailed exemplary methods for mapping an epitope to which an antibody binds are provided in Morris (1996) "Epitope Mapping Protocols," in *Methods in Molecular Biology vol.* 66 (Humana Press, Totowa, NJ).

In an exemplary competition assay, immobilized CD20 is incubated in a solution comprising a first labeled antibody that binds to CD20 (e.g., rituximab, a GA101 antibody, etc.) and a second unlabeled antibody that is being tested for its ability to compete with the first antibody for binding to CD20. The second antibody may be present in a hybridoma supernatant. As a control, immobilized CD20 is incubated in a solution comprising the first labeled antibody but not the second unlabeled antibody. After incubation under conditions permissive for binding of the first antibody to CD20, excess unbound antibody is removed, and the amount of label associated with immobilized CD20 is measured. If the amount of label associated with immobilized CD20 is substantially reduced in the test sample relative to the control sample, then that indicates that the second antibody is competing with the first antibody for binding to CD20. See Harlow and Lane (1988) *Antibodies: A Laboratory Manual* ch. 14 (Cold Spring Harbor Laboratory, Cold Spring Harbor, NY).

2. Activity Assays

Anti-CD20 antibodies of the present disclosure (e.g., a type II antibody) may be identified and/or characterized by one or more activity assays known in the art. For example, a complement-dependent cytotoxicity (CDC) and/or antibody-dependent cellular cytotoxicity (ADCC) may be used, as described herein.

It is understood that any of the above assays may be carried out using an immunoconjugate of the invention in place of or in addition to an anti-CD20 antibody.

It is understood that any of the above assays may be carried out using anti-CD20 antibody and an additional therapeutic agent.

C. Immunoconjugates

The invention also provides immunoconjugates comprising an anti-CD20 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. Sec WO94/11026. The linker may be a “cleavable linker” facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Methods for Treating or Delaying Progression of Lupus Nephritis

Certain aspects of the present disclosure relate to methods for treating or delaying progression of lupus nephritis (LN) in an individual that has lupus. In some embodiments, the individual or patient is a human.

LN is known in the art as a manifestation of lupus (e.g., systemic lupus erythematosus, drug-induced lupus, neonatal lupus, or discoid lupus) in the kidney(s). The most common type of lupus that manifests in the kidneys is systemic lupus erythematosus (SLE). It is thought that 25-50% of SLE patients have abnormalities in the urine and/or renal function early in the course of their disease, with up to 60% of adults and 80% of children eventually developing LN (for more details, see Cameron, J. S. (1999) *J. Am. Soc. Nephrol.* 10:413-424). LN is thought to account for at least 50% of the morbidity and mortality associated with SLE.

In addition, renal manifestations have also been noted in other types of lupus, such as discoid (Roujeau, J. C. et al. (1984) *Acta Derm. Venereol.* 64:160-163) and drug-induced lupus (Smith, P. R. et al. (1999) *Rheumatology* (*Oxford*) 38:1017-1018). In some embodiments, the individual has SLE, discoid lupus, or drug-induced lupus.

Diagnosis of SLE may be according to current American College of Rheumatology (ACR) criteria. Active disease may be defined by one British Isles Lupus Activity Group's (BILAG) "A" criteria or two BILAG "B" criteria; SLE Disease Activity Index (SLEDAI); or systemic lupus erythematosus (SLE) responder index (SRI) as noted in the Examples below and described in Furie et al., *Arthritis Rheum.* 61 (9): 1143-51 (2009). Some signs, symptoms, or other indicators used to diagnose SLE adapted from: Tan et al. "The Revised Criteria for the Classification of SLE" Arth Rheum 25 (1982) may be malar rash such as rash over the checks, discoid rash, or red raised patches, photosensitivity such as reaction to sunlight, resulting in the development of or increase in skin rash, oral ulcers such as ulcers in the nose or mouth, usually painless, arthritis, such as non-erosive arthritis involving two or more peripheral joints (arthritis in which the bones around the joints do not become destroyed), serositis, pleuritis or pericarditis, renal disorder such as excessive protein in the urine (greater than 0.5 gm/day or 3+ on test sticks) and/or cellular casts (abnormal elements derived from the urine and/or white cells and/or kidney tubule cells), neurologic signs, symptoms, or other indicators, seizures (convulsions), and/or psychosis in the absence of drugs or metabolic disturbances that are known to cause such effects, and hematologic signs, symptoms, or other indicators such as hemolytic anemia or leukopenia (white blood count below 4,000 cells per cubic millimeter) or lymphopenia (less than 1,500 lymphocytes per cubic millimeter) or thrombocytopenia (less than 100,000 platelets per cubic millimeter). The leukopenia and lymphopenia must be detected on two or more occasions. The thrombocytopenia must be detected in the absence of drugs known to induce it. The invention is not limited to these signs, symptoms, or other indicators of lupus.

The presence of autoantibodies may be tested as an indication for lupus. Autoantibodies may include without limitation anti-dsDNA antibodies, anti-complement antibodies, and antinuclear antibodies (e.g., an ENA panel). ENA refers to Extractable Nuclear Antigens, i.e., a group of nuclear antigens including, e.g., RNP, Ro/SS-A, La/SS-B, Sm, SCL-70, Jo-1, as described in McNeilage et al., J., Clin. Lab. Immunol. 15:1-17 (1984); Whittingham, Ann. Acad. Med. 17 (2): 195-200 (1988); Wallace and Hahn, DUBOIS' LUPUS ERYTHEMATOSUSz, $7^{TH}$ ED. LIPPINCOTT (2007); Tang et al., Medicine 89 (1): 62-67 (2010). Antibodies to ENA have been correlated to lupus. McNeilage et al., 1984; Whittingham 1988; Asherson et al., Medicine 68 (6): 366-374 (1989); and Tang et al., 2010. Reduced complement activity may also be associated with lupus, e.g., as measured by C3 levels, C4 levels, and/or a CH50 assay.

As described above in reference to SLE, it is known in the art that LN often manifests progressively in patients with lupus (e.g., systemic lupus erythematosus, drug-induced lupus, neonatal lupus, or discoid lupus). That is to say, a patient may be diagnosed with lupus without a clinical or pathological manifestation of one or more LN symptoms. Nonetheless, the patient may still be considered to be at risk for developing LN due to the high frequency of lupus patients that eventually develop LN. Therefore, in some embodiments, the methods of the present disclosure may find use in delaying progression of LN, or preventing LN, in a patient with lupus. In some embodiments, the methods of the present disclosure may find use in postponing or preventing the onset of LN in a patient with lupus (e.g., a form of lupus that lacks a manifestation in the kidney(s)).

LN pathology may be classified according to the International Society of Nephrology/Renal Pathology Society (ISN/RPS) 2003 classification system, as shown in the table below (see Markowitz G S, D'Agati V D (2007) *Kidney Int* 71:491-495 and Weening, JJ (2004) *Kidney Int* 65:521-530 for further descriptions and definitions of terms).

TABLE 3

| ISN/RPS 2003 Classification of Lupus Nephritis. | |
|---|---|
| Class I | Minimal mesangial LN<br>(Normal glomeruli by light microscopy, but mesangial immune deposits by immunofluorescence) |
| Class II | Mesangial proliferative LN<br>(Purely mesangial hypercellularity of any degree or mesangial matrix expansion by light microscopy, with mesangial immune deposits. A few isolated subepithelial or subendothelial deposits may be visible by immunofluorescence or electron microscopy, but not by light microscopy) |
| Class III | Focal LN<br>(Active or inactive focal, segmental or global endo- or extracapillary glomerulonephritis involving <50% of all glomeruli, typically with focal subendothelial immune deposits, with or without mesangial alterations)<br>III (A): active lesions (focal proliferative LN)<br>III (A/C): active and chronic lesions (focal proliferative and sclerosing LN)<br>III (C): chronic inactive lesions with glomerular scars (focal sclerosing LN) |
| Class IV | Diffuse LN<br>(Active or inactive diffuse, segmental or global endo- or extracapillary glomerulonephritis involving ≥50% of all glomeruli, typically with diffuse subendothelial immune deposits, with or without mesangial alterations. This class is divided into diffuse segmental (IV-S) LN when ≥50% of the involved glomeruli have segmental lesions, and diffuse global (IV-G) LN when ≥50% of the involved glomeruli have global lesions. Segmental is defined as a glomerular lesion that involves less than half of the glomerular tuft. This class includes cases with diffuse wire loop deposits but with little or no glomerular proliferation.)<br>IV-S (A): active lesions (diffuse segmental proliferative LN)<br>IV-G (A): active lesions (diffuse global proliferative LN)<br>IV-S (A/C): active and chronic lesions (diffuse segmental proliferative and sclerosing LN)<br>IV-G (A/C): active and chronic lesions (diffuse global proliferative and sclerosing LN)<br>IV-S (C): chronic inactive lesions with scars (diffuse segmental sclerosing LN)<br>IV-G (C): chronic inactive lesions with scars (diffuse global sclerosing LN) |

TABLE 3-continued

| ISN/RPS 2003 Classification of Lupus Nephritis. | |
|---|---|
| Class V | Membranous LN<br>(Global or segmental subepithelial immune deposits or their morphologic sequelae by light microscopy and by immunofluorescence or electron microscopy, with or without mesangial alterations.) |
| Class VI | Advanced sclerotic LN<br>(≥90% of glomeruli globally sclerosed without residual activity) |

LN = lupus nephritis;
A = active;
C = chronic;
G = global;
S = segmental.
Note:
Class V may occur in combination with Class III or IV, in which case both will be diagnosed. Class V LN may show advanced sclerosis.

In some embodiments, the patient has class III or class IV LN. In some embodiments, the patient has class III LN. For example, in some embodiments, the patient has class III (A) or class III (A/C) LN. In some embodiments, the patient has class IV LN. For example, in some embodiments, the patient has class IV-S(A), IV-G (A), IV-S(A/C), or IV-G (A/C) LN. As shown in Table 3 above, class V LN may also occur concomitantly with class III or class IV LN. In some embodiments, the methods of the present disclosure are used to treat a patient with class III or class IV LN and concomitant class V LN.

As discussed above, a high frequency of patients with lupus (e.g., SLE) eventually develop LN. In some embodiments, the patient is at risk for developing LN. In some embodiments, the patient is at risk for developing class III or class IV LN. In some embodiments, the patient is at risk for developing class III or class IV LN with concomitant class V LN.

In some embodiments, the patient does not have class III (C) LN (e.g., as described in Table 3 above). In some embodiments, the patient does not have class IV (C) LN, such as class IV-S(C) or IV-G (C) LN (e.g., as described in Table 3 above).

Several lab tests known in the art may be used to diagnose and/or monitor the presence, progression, and/or response to treatment in lupus nephritis. In some embodiments, serum creatinine may be measured. In some embodiments, the normal range for serum creatinine may be from about 0.6 to about 1.3 mg/dL, with some variation seen by age, between men and women, and from lab to lab. In some embodiments, the presence of urinary sediment and/or casts may be measured, e.g., by microscopic examination of urine. For example, the number of red blood cells in a urine sample may be assayed by microscopic examination. In some embodiments, a normal value for urinary sediment may be about 4 red blood cells (RBC) or less per high power field (HPF). Urinary casts may include without limitation red blood cell casts, white blood cell casts, renal tubular epithelial cell casts, waxy casts, hyaline casts, granular casts, and fatty casts. In some embodiments, a urinary protein to creatinine ratio (UPCR) may be measured. The presence of protein in the urine (proteinuria) may also be assayed by tests including without limitation a urine albumin to creatinine ratio (UACR) and dipstick urinalysis. Other tests and/or measures that may be useful for examining renal function include without limitation a renal panel, creatinine clearance, sodium, potassium, chloride, bicarbonate, phosphorus, calcium, albumin, blood urea nitrogen (BUN), creatinine, glucose, estimated glomerular filtration rate (eGFR), BUN/creatinine ratio, and anion gap, and may include a measurement of the above parameters in the blood and/or urine, where appropriate. For more detailed description, see, e.g., the American College of Rheumatology Guidelines for Screening, Case Definition, Treatment and Management of Lupus Nephritis (Hahn, B. et al. (2012) *Arthritis Care Res.* 64:797-808).

In some embodiments, the methods of the present disclosure include administering to the individual at least a first antibody exposure to a type II anti-CD20 antibody of the present disclosure and a second antibody exposure to the type II anti-CD20 antibody. Any of the type II anti-CD20 antibodies described herein may be used, e.g., a GA101 antibody such as obinutuzumab. In some embodiments, the second antibody exposure is not provided until from about 18 weeks to about 26 weeks after the first antibody exposure. In some embodiments, the second antibody exposure is not provided until about 18 weeks after the first antibody exposure, about 19 weeks after the first antibody exposure, about 20 weeks after the first antibody exposure, about 21 weeks after the first antibody exposure, about 22 weeks after the first antibody exposure, about 23 weeks after the first antibody exposure, about 24 weeks after the first antibody exposure, about 25 weeks after the first antibody exposure, or about 26 weeks after the first antibody exposure. In some embodiments, the second antibody exposure is not provided until less than about any of the following weeks after the first antibody exposure: 26, 25, 24, 23, 22, 21, 20, or 19. In some embodiments, the second antibody exposure is not provided until greater than about any of the following weeks after the first antibody exposure: 18, 19, 20, 21, 22, 23, 24, or 25. That is, the second antibody exposure is not provided until any of a range of weeks having an upper limit of 26, 25, 24, 23, 22, 21, 20, or 19 and an independently selected lower limit of 18, 19, 20, 21, 22, 23, 24, or 25, wherein the lower limit is less than the upper limit.

The dosing regimens described herein use a consistent system for tracking time between doses whereby the first dose is administered to the patient on Day 1. As described herein, an antibody exposure of the present disclosure may include one or two doses. In cases where the antibody exposures contain one dose, references to a second antibody exposure not provided until a period of time has elapsed after a first antibody exposure (as described herein) refer to the amount of time elapsed between the dose of the first antibody exposure (e.g., Day 1) and the dose of the second antibody exposure. If the first antibody exposure includes two doses, the first dose of the first antibody exposure is provided on Day 1. In cases where the antibody exposures contain two doses, references to a second antibody exposure not provided until a period of time has elapsed after a first antibody exposure (as described herein) refer to the amount of time elapsed between the first of the two doses of the first antibody exposure (e.g., Day 1) and the first dose of the two doses of the second antibody exposure. For example, if a method of the present disclosure includes a first antibody exposure with two doses and a second antibody exposure with two doses, and the second antibody exposure is not provided until about 22 weeks after the first antibody exposure, then the interval between the first dose of the first antibody exposure and the first dose of the second antibody exposure is about 22 weeks.

In some embodiments, a first antibody exposure of the present disclosure includes one or two doses of a type II anti-CD20 antibody of the present disclosure. In some embodiments, the first antibody exposure contains a total exposure of between about 1800 mg and about 2200 mg of the type II anti-CD20 antibody. In some embodiments, the first antibody exposure contains a total exposure of about 1800 mg, about 1900 mg, about 2000 mg, about 2100 mg, or about 2200 mg of the type II anti-CD20 antibody.

In some embodiments, the first antibody exposure includes two doses. In some embodiments, the first antibody exposure includes a first dose of between about 900 mg and about 1100 mg of the type II anti-CD20 antibody and a second dose of between about 900 mg and about 1100 mg of the type II anti-CD20 antibody. In some embodiments, the first dose of the first antibody exposure contains about 1000 mg of the type II anti-CD20 antibody. In some embodiments, the second dose of the first antibody exposure contains about 1000 mg of the type II anti-CD20 antibody. In some embodiments, the second dose of the first antibody exposure is not provided until about 1.5 weeks to about 2.5 weeks after the first dose of the first antibody exposure. In some embodiments, the second dose of the first antibody exposure is not provided until about 2 weeks after the first dose of the first antibody exposure.

In some embodiments, a second antibody exposure of the present disclosure includes one or two doses of a type II anti-CD20 antibody of the present disclosure. In some embodiments, the second antibody exposure contains a total exposure of between about 1800 mg and about 2200 mg of the type II anti-CD20 antibody. In some embodiments, the second antibody exposure contains a total exposure of about 1800 mg, about 1900 mg, about 2000 mg, about 2100 mg, or about 2200 mg of the type II anti-CD20 antibody.

In some embodiments, the second antibody exposure includes two doses. In some embodiments, the second antibody exposure includes a first dose of between about 900 mg and about 1100 mg of the type II anti-CD20 antibody and a second dose of between about 900 mg and about 1100 mg of the type II anti-CD20 antibody. In some embodiments, the first dose of the second antibody exposure contains about 1000 mg of the type II anti-CD20 antibody. In some embodiments, the second dose of the second antibody exposure contains about 1000 mg of the type II anti-CD20 antibody. In some embodiments, the second dose of the second antibody exposure is not provided until about 1.5 weeks to about 2.5 weeks after the first dose of the second antibody exposure. In some embodiments, the second dose of the second antibody exposure is not provided until about 2 weeks after the first dose of the second antibody exposure.

In some embodiments, a type II anti-CD20 antibody of the present disclosure is administered intravenously (e.g., by IV infusion).

In some embodiments, the methods of the present disclosure further include administering an effective amount of an immunosuppressive agent (e.g., in conjunction with a type II anti-CD20 antibody as described herein). Several classes of immunosuppressive agents are known in the art, including without limitation cytostatics (e.g., cytotoxic agents such as antibiotics, alkylating agents (e.g., cyclophosphamide, also known as cytophosphane), inosine monophosphate dehydrogenase inhibitors, antimetabolites such as protein synthesis inhibitors, folic acid analogs, purine analogs, pyrimidine analogs, and the like), immunosuppressive antibodies, glucocorticoids, drugs targeting immunophilins (e.g., tacrolimus, sirolimus, rapamycin and analogs thereof, ciclosporin, and the like), mTOR active site inhibitors, mycophenolic acid and derivatives or salts thereof, TNF binding proteins, interferons, opioids, and other small molecules (e.g., fingolimod). In some embodiments, the immunosuppressive agent includes mycophenolic acid, a derivative of mycophenolic acid, or a salt of mycophenolic acid. In some embodiments, the immunosuppressive agent includes mycophenolate mofetil. In some embodiments, the immunosuppressive agent includes CellCept® (Roche). In some embodiments, the immunosuppressive agent includes Myfortic® (Novartis). Effective amounts of the immunosuppressive agents of the present disclosure are known in the art and readily ascertainable by standard assays. For example, mycophenolate mofetil may be administered at 2.0-2.5 g/day as illustrated in FIG. 1. In some embodiments, mycophenolate mofetil may be administered starting at 1000 mg/day in divided doses (2 times/day) and titrating up to 2.0-2.5 g/day in divided doses (2 times/day) by week 4.

In some embodiments, an immunosuppressive agent may be administered before, during, or after administration of a type II anti-CD20 antibody of the present disclosure, e.g., as a treatment for lupus. In some embodiments, an immunosuppressive agent may be administered throughout the period of treatment with a type II anti-CD20 antibody of the present disclosure. In some embodiments, mycophenolate mofetil may be administered as described above throughout the period of treatment with the type II anti-CD20 antibody.

In some embodiments, the methods of the present disclosure further include administering an effective amount of a glucocorticoid or corticosteroid (e.g., in conjunction with a type II anti-CD20 antibody as described herein). A variety of naturally occurring and synthetic glucocorticoids/corticosteroids are known in the art, including without limitation beclometasone, triamcinolone, dexamethasone, betamethasone, prednisone, methylprednisolone, prednisolone, cortisone, and cortisol. In some embodiments, the glucocorticoids/corticosteroid includes methylprednisolone. In some embodiments, the glucocorticoids/corticosteroid includes prednisone. Effective amounts of the glucocorticoids/corticosteroids of the present disclosure are known in the art and readily ascertainable by standard assays. For example, methylprednisolone may be administered at 750-1000 mg doses once daily by IV. As another example, prednisone may be administered orally at 0.5 mg/kg and optionally tapered to 7.5 mg/day.

In some embodiments, a glucocorticoid may be administered before, during, or after administration of a type II anti-CD20 antibody of the present disclosure, e.g., to treat LN clinical activity. In some embodiments, a glucocorticoid may be administered prior to administration of a type II anti-CD20 antibody of the present disclosure, e.g., 30-60 minutes before the type II anti-CD20 antibody. In some embodiments, 80 mg methylprednisolone may be administered by IV 30-60 minutes before administration of a type II anti-CD20 antibody of the present disclosure. In some embodiments, prednisone (e.g., orally administered) and/or methyl prednisolone (e.g., IV administered) may be administered with treatment, followed by a maintenance treatment (e.g., mycophenolate mofetil or cyclophosphamide).

In some embodiments, the methods of the present disclosure further include administering an effective amount of an antihistamine (e.g., in conjunction with a type II anti-CD20 antibody as described herein). Antihistamines known in the art and currently in clinical use include histamine Hi-receptor and histamine H2-receptor antagonists or inverse agonists. In some embodiments, the antihistamine includes diphenhydramine. Effective amounts of the antihistamines of the present disclosure are known in the art and readily ascertainable by standard assays. For example, diphenhydramine may be administered in 50 mg oral doses.

In some embodiments, an antihistamine may be administered before, during, or after administration of a type II anti-CD20 antibody of the present disclosure, e.g., as a prophylactic treatment. In some embodiments, an antihistamine may be administered prior to administration of a type II anti-CD20 antibody of the present disclosure, e.g., 30-60 minutes before the type II anti-CD20 antibody. In some embodiments, 50 mg diphenhydramine may be administered orally 30-60 minutes before administration of a type II anti-CD20 antibody of the present disclosure.

In some embodiments, the methods of the present disclosure further include administering an effective amount of a non-steroidal anti-inflammatory drug or NSAID (e.g., in conjunction with a type II anti-CD20 antibody as described herein). NSAIDs known in the art include acetic acid derivatives, propionic acid derivatives, salicylates, enolic acid derivatives, anthranilic acid derivatives, selective COX-2 inhibitors, sulfonanilides, and the like. In some embodiments, the NSAID includes acetaminophen. Effective amounts of the NSAIDs of the present disclosure are known in the art and readily ascertainable by standard assays. For example, acetaminophen may be administered in 650-1000 mg oral doses.

In some embodiments, an NSAID may be administered before, during, or after administration of a type II anti-CD20 antibody of the present disclosure, e.g., as a prophylactic treatment. In some embodiments, an NSAID may be administered prior to administration of a type II anti-CD20 antibody of the present disclosure, e.g., 30-60 minutes before the type II anti-CD20 antibody. In some embodiments, 650-1000 mg acetaminophen may be administered orally 30-60 minutes before administration of a type II anti-CD20 antibody of the present disclosure.

In some embodiments, the methods of the present disclosure further include administering an effective amount of an anti-malarial agent (e.g., in conjunction with a type II anti-CD20 antibody as described herein). Examples of anti-malarial agents that may be used include without limitation hydroxychloroquine, chloroquine, and quinacrine. In some embodiments, an anti-malarial agent may be administered before, during, or after administration of a type II anti-CD20 antibody of the present disclosure, e.g., as a treatment for one or more symptoms of lupus.

In some embodiments, the methods of the present disclosure further include administering an effective amount of an integrin antagonist (e.g., in conjunction with a type II anti-CD20 antibody as described herein). Examples of integrin antagonists that may be used include without limitation an LFA-1 antibody, such as efalizumab (RAPTIVA®) commercially available from Genentech, or an alpha 4 integrin antibody such as natalizumab (ANTEGREN®)) available from Biogen. or diazacyclic phenylalanine derivatives, phenylalanine derivatives, phenylpropionic acid derivatives, enamine derivatives, propanoic acid derivatives, alkanoic acid derivatives, substituted phenyl derivatives, aromatic amine derivatives, ADAM disintegrin domain polypeptides, antibodies to alphavbeta3 integrin, aza-bridged bicyclic amino acid derivatives, etc. In some embodiments, an integrin antagonist may be administered before, during, or after administration of a type II anti-CD20 antibody of the present disclosure, e.g., as a treatment for one or more symptoms of lupus.

In some embodiments, the methods of the present disclosure further include administering an effective amount of a cytokine antagonist (e.g., in conjunction with a type II anti-CD20 antibody as described herein). Examples of cytokine antagonists that may be used include without limitation an antagonist (e.g., an antagonist antibody) against IL-1, IL-1α, IL-2, IL-3, IL-4, IL-5. IL-6, IL-7, IL-8, IL-9. IL-11, IL-12, IL-15; a tumor necrosis factor such as TNF-α or TNF-β; and other polypeptide factors including LIF and kit ligand (KL). In some embodiments, a cytokine antagonist may be administered before, during, or after administration of a type II anti-CD20 antibody of the present disclosure, e.g., as a treatment for one or more symptoms of lupus.

In some embodiments, the methods of the present disclosure further include administering an effective amount of a hormone (e.g., in conjunction with a type II anti-CD20 antibody as described herein). In some embodiments, a hormone (e.g., for hormone replacement therapy) may be administered before, during, or after administration of a type II anti-CD20 antibody of the present disclosure, e.g., for a medical treatment in a women with lupus.

In some embodiments, the methods of the present disclosure further include administering a standard of care treatment (e.g., in conjunction with a type II anti-CD20 antibody as described herein). In some embodiments, a standard of care treatment may be administered before, during, or after administration of a type II anti-CD20 antibody of the present disclosure, e.g., for treating or preventing one or more symptoms of lupus. In certain embodiments, a standard of care treatment may be administered after a second antibody exposure of the present disclosure. For example, a type II anti-CD20 antibody of the present disclosure may be administered as described herein to a patient as an induction therapy, then the patient may be treated according to standard of care as a maintenance therapy. Standard of care treatments for lupus are well known in the art and include without limitation an angiotensin-converting enzyme (ACE) inhibitor, an angiotensin-receptor blocker, cyclophosphamide, mycophenolate mofetil (e.g., at a dose as described herein, such as 2.0-2.5 g/day), azathioprine, and a glucocorticoid or corticosteroid (e.g., prednisone, such as a prednisone taper).

In some embodiments, the methods of the present disclosure further include administering an anti-hypertensive agent (e.g., in conjunction with a type II anti-CD20 antibody as described herein). In some embodiments, an anti-hypertensive agent may be administered before, during, or after administration of a type II anti-CD20 antibody of the present disclosure, e.g., for treating or preventing hypertension. In some embodiments, anti-hypertensive agents includes without limitation ACE inhibitors and angiotensin-receptor blockers. In some embodiments, an anti-hypertensive agent listed in Table 5 is administered, e.g., at a dose within the ranges described in Table 5.

In some embodiments, the methods of the present disclosure result in a complete renal response (CRR) in an individual. In some embodiments, a CRR comprises all of the following: a normalization of serum creatinine, an inactive urinary sediment, and a urinary protein to creatinine ratio of <0.5. In some embodiments, a normalization of serum creatinine is characterized by serum creatinine less than or equal to the upper limit of normal (ULN) range of central laboratory values, and/or serum creatinine ≤15% above baseline and less than or equal to the ULN range of central laboratory values if baseline (e.g., Day 1) serum creatinine is within the normal range of the central laboratory values. In some embodiments, an inactive urinary sediment is characterized by <10 RBCs/high-power field (HPF) and/or the absence of red cell casts. For more detailed discussion of CRR and partial renal response (PRR) in LN, see, e.g., Chen, Y. E. et al. (2008) *Clin. J. Am. Soc. Nephrol.* 3:46-53.

In some embodiments, the methods of the present disclosure result in a complete renal response (CRR) or a partial renal response (PRR) in an individual. In some embodiments, a PRR comprises one or more of the following: a normalization of serum creatinine, an inactive urinary sediment, and a urinary protein to creatinine ratio of <0.5. In some embodiments, a PRR comprises one or more of the following: mitigation of one or more symptoms including without limitation a reduction in serum creatinine, reduced urinary sediment, a reduction in proteinuria, and any other improvement in renal function. In some embodiments, a CRR or PRR comprises a reduction in one or more biomarkers of lupus activity, including without limitation anti-dsDNA antibodies, antinuclear antibodies/ENA, anti-complement antibodies, reduced levels of complement C3 and/or C4, and reduced complement activity (e.g., as measured by CH50 assay).

In some embodiments, the methods of the present disclosure result in a depletion of circulating peripheral B cells in an individual. In some embodiments, after administration of a type II anti-CD20 antibody of the present disclosure (e.g., according to any of the methods described herein), circulating peripheral B cells are present in peripheral blood at about 10 cells/μL or fewer, about 9 cells/μL or fewer, about 8 cells/μL or fewer, about 7 cells/μL or fewer, about 6 cells/μL or fewer, about 5 cells/μL or fewer, about 4 cells/μL or fewer, about 3 cells/μL or fewer, about 2 cells/μL or fewer, or about 1 cell/μL or fewer. In some embodiments, circulating peripheral B cells in the individual are depleted by at least about 10%, at least about 20%, at least about 30%, at least about 40%, at least about 50%, at least about 60%, at least about 70%, at least about 80%, at least about 90%, or about 100%. In some embodiments, depletion of circulating peripheral B cells refers to a measurement of circulating peripheral B cells taken after a first antibody exposure (e.g., including 1 or 2 doses of an anti-CD20 antibody as described herein), after a second antibody exposure (e.g., including 1 or 2 doses of an anti-CD20 antibody as described herein), 3 months after treatment (e.g., after receiving a first and/or a second antibody exposure as described herein), 6 months after treatment (e.g., after receiving a first and/or a second antibody exposure as described herein), 9 months after treatment (e.g., after receiving a first and/or a second antibody exposure as described herein), or 12 months after treatment (e.g., after receiving a first and/or a second antibody exposure as described herein), e.g., as compared to a corresponding measurement in the same individual before treatment, or as compared to a corresponding measurement in a control individual (e.g., an individual that has not received treatment).

Methods for assaying depletion of circulating peripheral B cells in an individual are known in the art, e.g., flow cytometry using one or more antibodies that recognize a B cell marker. In some embodiments, highly sensitive flow cytometry (HSFC) may be used to assay depletion of circulating peripheral B cells (see, e.g., Vital, E. M. et al. (2011) *Arthritis Rheum.* 63:3038-3047). In some embodiments, the B cells are CD19+ B cells. In some embodiments, the B cells are naïve B cells (e.g., CD19+CD27− B cells), memory B cells (e.g., CD19+CD27+ B cells), or plasmablasts (e.g., CD19+CD27+CD38++ B cells).

IV. Articles of Manufacture or Kits

In another aspect of the invention, an article of manufacture or kit containing materials useful for the treatment, prevention and/or diagnosis of the disorders described above is provided. The article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody described herein (e.g., a type II anti-CD20 antibody of the present disclosure). The label or package insert indicates that the composition is used for treating the condition of choice, e.g., according to any of the methods described herein. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, provided herein is a kit comprising a container comprising a type II anti-CD20 antibody of the present disclosure and an optional pharmaceutically acceptable carrier, and, optionally, a package insert comprising instructions for treating or delaying progression of lupus nephritis in an individual, e.g., wherein the instructions indicate that at least a first antibody exposure to a type II anti-CD20 antibody and a second antibody exposure to the type II anti-CD20 antibody are administered to the individual, the second antibody exposure not being provided until from about 18 weeks to about 26 weeks after the first antibody exposure; wherein the first antibody exposure comprises one or two doses of the type II anti-CD20 antibody, the first antibody exposure comprising a total exposure of between about 1800 mg and about 2200 mg of the type II anti-CD20 antibody; and wherein the second antibody exposure comprises one or two doses of the type II anti-CD20 antibody, the second antibody exposure comprising a total exposure of between about 1800 mg and about 2200 mg of the type II anti-CD20 antibody. In some embodiments, provided herein is a kit comprising a container comprising a type II anti-CD20 antibody of the present disclosure and an optional pharmaceutically acceptable carrier, and, optionally, a package insert comprising instructions for treating or delaying progression of class III or class IV lupus nephritis in an individual. In some embodiments of any of the above embodiments, the type II anti-CD20 antibody comprises a heavy chain comprising HVR-H1 sequence of SEQ ID NO:1, HVR-H2 sequence of SEQ ID NO: 2, and HVR-H3 sequence of SEQ ID NO:3, and a light chain comprising HVR-L1 sequence of SEQ ID NO:4, HVR-L2 sequence of SEQ ID NO:5, and HVR-L3 sequence of SEQ ID NO:6. In some embodiments of any of the above embodiments, the type II anti-CD20 antibody is obinutuzumab.

The article of manufacture may still further comprise a second or third container comprising a second medicament, wherein the anti-CD20 antibody (e.g., a type II anti-CD20 antibody of the present disclosure) is a first medicament, where the article further comprises instructions on the package insert for treating the subject with the second medicament. Exemplary second medicaments include a chemotherapeutic agent, an immunosuppressive agent, an anti-malarial agent, a cytotoxic agent, an integrin antagonist, a cytokine antagonist, a hormone, and any of the treatments that may be used in conjunction with a type II anti-CD20 antibody as described herein. The article of manufacture in these embodiments may further comprise a package insert indicating that the compositions can be used to treat a particular condition.

It is understood that any of the above articles of manufacture may include an immunoconjugate of the invention in place of or in addition to an anti-CD20 antibody.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: A Pharmacology Study of Obinutuzumab Administered with Mycophenolate Mofetil in Patients with Class III/IV Lupus Nephritis Study Design This Phase II study is designed to assess the safety and efficacy of obinutuzumab (i.e., a type II anti-CD20 antibody) as an add-on therapy to mycophenolate mofetil (MMF) in patients with active ISN/RPS Class III/IV lupus nephritis (LN). The Phase II study is a parallel-group, double-blind, randomized, placebo-controlled study comparing the efficacy and safety of obinutuzumab plus MMF with placebo plus MMF in Class III and IV patients with proliferative LN (FIG. 1).

The study is also a prospective, multicenter study. Patients diagnosed with ISN/RPS Class III or IV LN, in some embodiments with a diagnosis of SLE according to current ACR criteria (at least 4 criteria must be present, one of which must be a positive anti-nuclear antibody), are enrolled in centers throughout the world. The study includes standard-of-care therapy with angiotensin-converting enzyme (ACE) inhibitors/angiotensin II receptor blockers, MMF (dosed at 2.0-2.5 g/day), and a prednisone taper.

As described in greater detail below, patients are 18-75 years of age and have ISN/RPS 2003 Class III or IV proliferative LN (see Weening, JJ (2004) *J. Am. Soc. Nephrol.* 15:241-250) as evidenced by renal biopsy performed within 6 months prior to screening and may have concomitant Class V disease (e.g., Class III/V or Class IV/V). Patients with Class III (C) or Class IV (C) disease are excluded because of the lower likelihood of response within these categories.

Inclusion criteria for the study include:

(a) Signed Informed Consent Form;

(b) Age 18-75 years;

(c) Ability to comply with study protocol;

(d) Diagnosis of systemic lupus erythematosus (SLE) according to current ACR criteria (at least 4 criteria must be present, one of which must be a positive anti-nuclear antibody);

(e) Diagnosis of ISN/RPS 2003 Class III or IV LN as evidenced by renal biopsy performed within 6 months prior to screening (patients may also co-exhibit Class V disease in addition to either Class III or Class IV disease);

(f) Demonstration of active urinary sediment as evidenced by ≥10 RBCs/HPF or the presence of red cell casts; and (g) Proteinuria (urine protein to creatinine ratio >1.0, based on a 24-hour urine collection).

Key exclusion criteria include:

(a) Retinitis, poorly controlled seizure disorder, acute confusional state, myelitis, stroke or stroke syndrome, cerebellar ataxia, or dementia that is currently active and resulting from SLE;

(b) Presence of rapidly progressive glomerulonephritis (defined by the presence of crescent formation in ≥50% of glomeruli assessed on renal biopsy or the doubling of serum creatinine within 12 weeks of screening);

(c) Severe renal impairment as defined by estimated GFR <30 mL/min or the need for dialysis or renal transplant;

(d) Greater than 50% of glomeruli with sclerosis on renal biopsy;

(e) Treatment with cyclophosphamide or calcineurin inhibitors within the 3 months prior to randomization; and (f) Unstable disease with thrombocytopenia or at high risk for developing clinically significant bleeding or organ dysfunction requiring therapies such as plasmapheresis or acute blood or platelet transfusions.

Patients receive an initial 1000 mg of methylprednisolone intravenously (IV) prior to or during screening, and may receive up to 3000 mg methylprednisolone IV prior to randomization for severe clinical activity according to guidelines of routine care for these patients. Patients receive 80 mg methylprednisolone (or methylprednisolone placebo) IV on the day of the obinutuzumab/placebo infusion to reduce infusion-related events. The oral prednisone taper is 0.5 mg/kg and is reduced over 12 weeks. This modified taper is initiated in recognition that prednisone doses above 10 mg/day are associated with significant adverse events, including increased risk of cardiovascular events (Bichile, T. and Petri, M. (2014) *Presse Med.* 43: e187-195). Prior experience with rituximab suggests that it can potentially enable complete and partial renal responses in the absence of oral prednisone or a prednisone taper, thus allowing the use of lower doses of corticosteroids (Condon, M. B. et al. (2013) *Ann. Rheum. Dis.* 72:1280-1286).

Patients are followed for 12 months until the primary endpoint evaluation, and an interim analysis at 6 months is performed to evaluate early differences in CRR. All patients have central reading of the renal biopsy histopathology and also receive repeat renal biopsy as available on the basis of clinical status and local practice. All patients are evaluated by high sensitivity flow cytometry (HSFC) to evaluate the ability of obinutuzumab to deplete circulating peripheral B cells, and an interim PD analysis is performed to assess whether patients do not fully deplete peripheral CD19+ B cells as anticipated.

Dosing and Non-Investigational Medicinal Products

The dosing regimen for the study is obinutuzumab administered by IV infusion at a dose of 1000 mg on Days 1, 15, 168, and 182 (test group); or obinutuzumab placebo (e.g., saline IV, corresponding to the obinutuzumab 1000-mg dose) administered by IV infusion on Days 1, 15, 168, and 182. The obinutuzumab/placebo is administered in a hospital or clinic environment where full resuscitation facilities are immediately available and under close supervision of the investigator or designee. After the end of the infusion, the IV line remains in place for at least 1 hour to enable administration of IV drugs if necessary. If no adverse events occur during this period of time, the IV line may be removed.

After screening, patients who are not already receiving MMF receive 1500 mg/day MMF in divided doses (2-3 times/day), and all patient doses are titrated up to a target dose of 2.0-2.5 g/day in divided doses (2-3 times/day) by Week 4, as tolerated. If reductions in dose are necessary, decreases are allowed in 250-500 mg decrements. During screening or at randomization, if clinically indicated, patients may receive 750-1000 mg methylprednisolone IV once daily for up to three days to treat underlying LN clinical activity. Patients receive 0.5 mg/kg oral prednisone during screening or at randomization, tapering this prednisone dose, per protocol, starting on Day 16 and reducing the prednisone dosage to 7.5 mg/day by Week 12. These treatments are described in further detail below.

Concomitant Therapy and Clinical Practice

Patients who are not already taking vitamin D (400 IU/day) and calcium supplements (1200 mg/day of calcium citrate or 1500 mg/day of calcium carbonate) begin taking these supplements at randomization. All patients take either an angiotensin-converting enzyme inhibitor or an angiotensin receptor blocker titrated to adequate blood pressure control as recommended by the National Kidney Foundation for chronic kidney disease. Other agents that affect proteinuria are not allowed to be initiated during the study, including but not limited to non-dihydropyridine calcium antagonists, dihydropyridine calcium antagonists, aldosterone antagonists, and direct renin antagonists.

Mycophenolate Mofetil (MMF)

All patients continue on or initiate use of MMF during screening or no later than Day 1. The initial dosage is 1500 mg/day by mouth, given in two or three divided doses and titrated upward to 2.0-2.5 g/day in divided doses by Week 4. MMF may be increased by 500 mg/week, as tolerated up to a maximum dosage of 2.5 g/day. Reductions are allowed because of adverse effects.

Newly diagnosed patients with LN with no prior exposure to MMF are recommended to initiate an induction agent (MMF or cyclophosphamide) and then be re-assessed for eligibility. A proportion of patients who are initially treated with MMF or cyclophosphamide achieve CRR and therefore have minimal need for added immunosuppression (Dall'Era, M. et al. (2011) *Arthritis Care Res.* 63:351-357).

For those patients who enter the study already receiving a dosage of MMF higher than 1500 mg/day, MMF will be titrated upward, as tolerated, to a goal of 2.5 g/day, given in divided doses, by Week 4. A patient's current dose of MMF is given in 2 or 3 divided doses and increased by 500 mg/week as tolerated.

Corticosteroid Administration

All patients receive a combination of IV and oral corticosteroids as part of their initial therapy for LN. Methylprednisolone (e.g., Solu-Medrol®) is implemented for two purposes: as part of the usual care for patients with active Class III or IV LN and also to reduce infusion-related reactions (IRRs) on the days of obinutuzumab/placebo infusions. Up to three doses of IV methylprednisolone 1000 mg are given on the basis of investigator judgement and local practice. Up to three 1000 mg infusions may have been initiated prior to screening or during the screening interval.

On Days 1, 15, 168, and 186, patients receive 80 mg IV methylprednisolone or placebo 30-60 minutes prior to study drug infusion to prevent IRRs. Additionally, oral prednisone may be initiated before or during the screening interval, and a taper commences on Day 2. From Days 2 to 16, 0.50 mg/kg/day oral prednisone is given (maximum dose 60 mg), except on the day of IV methylprednisolone/placebo infusions, and will continue until Day 16. From Day 16 onward, a prednisone taper commences.

All patients undergo a scheduled corticosteroid taper commencing on Day 16. Patients fractionally reduce their prednisone dose over 12 weeks until the dose is 7.5 mg/day by Week 12. After 14 weeks of tapering, patients continue on prednisone at 7.5 mg/day or less. In patients whose disease is too clinically active for the patient to make the first step in their prednisone taper, as evidenced by active urinary sediment, rising serum creatinine, or moderate-to-severe extra-renal symptoms, these patients may continue to receive their initial prednisone dose for up to an additional 28 days.

To maintain consistency in the treatment of renal flares, retreatment with higher doses of corticosteroids is permitted if judged clinically appropriate by the investigator and if patients meet criteria for a renal flare. Patients may be treated with prednisone (up to 0.5 mg/kg; not to exceed 60 mg/day) for 2 weeks. Prednisone is then tapered to achieve 10 mg/day within 6 weeks after initial corticosteroid increase. Patients are allowed to receive corticosteroids for emergent illness (trauma, severe asthma) or surgery, if clinically warranted; the corticosteroid use is limited to a total of ≤7 days, if possible. Investigators are then allowed to increase the prednisone dose by ≤2.5 mg/day to treat symptoms of adrenal insufficiency or corticosteroid withdrawal, after the patient's dosage has been tapered to 10 mg/day.

Patients who experience a severe extra-renal SLE flare may receive treatment with additional oral corticosteroids, if judged clinically appropriate by the investigator. These patients may be retreated with prednisone (up to 1.0 mg/kg) for up to 2 weeks on the basis of the severity of disease and organ system involvement and the dosage is tapered to 7.5 mg/day. Patients experiencing a mild or moderate extra-renal flare may temporarily increase their prednisone dose by up to 20 mg per day and taper this dose over 4 weeks, if judged clinically appropriate by the investigator. IV corticosteroids in equivalent doses are allowed if gastrointestinal involvement temporarily precludes treatment with oral corticosteroids.

Anti-Malarial Medications

Patients taking anti-malarial medications at study entry maintain a constant dosage throughout the study. Patients not previously on anti-malarial medications may be enrolled in the study but should not initiate anti-malarial medications unless experiencing a disease flare that is unresponsive to corticosteroids. Table 4 lists anti-malarial medications and dose ranges expected to be used during the course of the study.

TABLE 4

| Anti-malarial medications | |
|---|---|
| Anti-malarial Medication | Dose Range (oral) |
| Hydroxychloroquine | 200-400 mg daily |
| Chloroquine | 500 mg every day or every other day |
| Quinacrine | 100 mg every day |

Antihypertensive Therapy

All patients who are not currently taking either an ACE inhibitor or an angiotensin-receptor blocker should be started on one at screening. Patients are on either an ACE inhibitor or angiotensin-receptor blocker for at least 10 days prior to randomization. Combination therapy with the two agents is not allowed.

During screening, every effort is made to adequately control patients' blood pressures. The dose of the ACE inhibitor or angiotensin-receptor blocker may be titrated upward to the maximum recommended dose in the current package insert to achieve adequate blood pressure control as recommended by the Eighth Report of the Joint National Committee on the Prevention, Detection, Evaluation, and Treatment of High Blood Pressure (James, P. A. et al. (2014) JAMA 311:507-520). If adequate blood pressure control is not achieved, patients may be started on additional antihypertensive agents but not on agents that affect proteinuria (e.g., nondihydropyridine calcium channel blockers, aldosterone antagonists, direct renin antagonists). Additional agents that specifically target the renin-angiotensin system are not initiated during the study. Suggested dose ranges for specific ACE inhibitors and angiotensin-receptor blockers are listed in Table 5. If patients are intolerant to ACE inhibitors and angiotensin-receptor blockers, they may use either a direct renin inhibitor or aldosterone antagonists, but not in combination.

TABLE 5

| Suggested Dose Ranges for ACE Inhibitors and Angiotensin-Receptor Blockers | |
|---|---|
| ACE Inhibitor or Angiotensin-Receptor Blocker | Dose Range (Oral), mg/day |
| ACE Inhibitors | |
| Benazepril | 10-80 |
| Ramipril | 2.5-10 |
| Lisinopril | 10-80 |
| Enalapril | 10-40 |
| Quinapril | 10-80 |
| Captopril | 75-450 |
| Perindopril | 4-16 |
| Trandolapril | 1-8 |
| Moexipril | 7.5-30 |

TABLE 5-continued

| Suggested Dose Ranges for ACE Inhibitors and Angiotensin-Receptor Blockers | |
|---|---|
| ACE Inhibitor or Angiotensin-Receptor Blocker | Dose Range (Oral), mg/day |
| Angiotensin-Receptor Blockers | |
| Eprosartan | 400-600 |
| Valsartan | 80-320 |
| Olmesartan | 20-40 |
| Candesartan | 8-32 |
| Telmisartan | 20-80 |
| Losartan | 25-100 |
| Irbesartan | 75-300 |

Study Objectives and Outcome Measures

The primary objective of this proof-of-concept study is to measure complete renal response (CRR) at 52 weeks with administration of obinutuzumab. The ability of obinutuzumab plus MMF to achieve a CRR at week 52 is compared to placebo plus MMF and assessed by improvements in renal function, urinary sediment, and proteinuria. Secondary objectives include evaluations of the safety of obinutuzumab in this patient population, the ability of obinutuzumab to induce an overall response (CRR+PRR) at Week 52, the ability of obinutuzumab to improve time-to-response (CRR+PRR) over the course of 52 weeks, and the ability of obinutuzumab to improve biomarkers of LN disease activity (e.g., reduced anti-dsDNA antibody levels, increased C3 and C4 levels; see Tew, G. W. et al. (2010) *Lupus* 19:146-157).

The primary efficacy outcome measure is the proportion of subjects who achieve a CRR, evaluated at 52 weeks. In this study, CRR is defined by attainment of all of the following:

(a) Normalization of serum creatinine as evidenced by the following:
  (i) Serum creatinine less than or equal to the upper limit of normal (ULN) range of central laboratory values if the baseline (Day 1) is not within the normal range of the central laboratory values; and
  (ii) Serum creatinine ≤15% above baseline and less than or equal to the ULN range of central laboratory values if baseline (Day 1) serum creatinine is within the normal range of the central laboratory values;
(b) Inactive urinary sediment (as evidenced by <10 RBCs/high-power field (HPF) and the absence of red cell casts); and
(c) Urinary protein to creatinine ratio <0.5.

Any patient who switches to rescue medication prior to Week 52 is considered a non-responder. The proportions of patients achieving CRR across treatment groups is compared using a Cochrane-Mantel-Haenzel (CMH) test with race (Afro-Caribbean/African-American versus others) and region (United States versus non-United States) as stratification factors. If the test result is in favor of the obinutuzumab group at α<0.1-level (one-sided), a shift toward better renal response associated with the obinutuzumab group is concluded.

The secondary efficacy outcome measures are the following:

(a) Proportional analysis of patients who achieve an overall response at Week 52 (CRR+PRR);
(b) Time to overall response (CRR+PRR) over the course of 52 weeks;

(c) Percent reduction or increase from baseline and mean and median assessments of biomarkers of LN disease activity (e.g., reduction in anti-dsDNA antibody levels, increased C3 and C4 levels);

(d) Proportion of patients that achieve a PRR at week 52 as defined by attainment of all of the following:

(i) serum creatinine ≤15% above baseline levels;

(ii) RBCs/HPF ≤50% above baseline and no red cell casts;

(iii) 50% improvement in the urine protein to creatinine ratio, with one of the following conditions met:

(A) if the baseline urine protein to creatinine ratio is ≤3.0, then a urine protein to creatine ratio of <1.0;

(B) if the baseline protein to creatinine ratio is >3.0, then a urine protein to creatinine ratio of <3.0;

(e) Proportion of patients who achieve a CRR at Week 24;

(f) Time to CRR, over the course of 52 weeks;

(g) Proportion of patients that achieve a modified CRR (mCRR1) at Week 52 employing the primary-efficacy measure definition and removing the urinary sediment analysis criteria mCRR1 refers to attainment of normalization of serum creatinine as evidenced by the following:

(i) Serum creatinine less than or equal to the ULN range of central laboratory values;

(ii) Serum creatinine ≤15% above baseline and less than or equal to the ULN range of central laboratory values if baseline (Day 1) serum creatinine is within the normal range of the central laboratory values;

(iii) Urinary protein to creatinine ratio <0.5;

(h) Proportion of patients that achieve a second CRR (mCRR2) at Week 52 as defined by attainment of the following:

(i) Normalization of serum creatinine as evidenced by the following:

(A) Serum creatinine ≤the ULN range of central laboratory values;

(B) Serum creatinine ≤15% above baseline if baseline (Day 1) serum creatinine is above the normal range of the central laboratory values OR S ≤the ULN range of central laboratory values if baseline (Day 1) serum creatinine is within the normal range of the central laboratory values;

(ii) Inactive urinary sediment (as evidenced by <10 RBCs/HPF and the absence of red cell casts);

(iii) Urinary protein to creatinine ratio <0.5.

The pharmacodynamic (PD) objective is to compare changes in CD19+ B cells in the peripheral blood following treatment with obinutuzumab versus placebo. Levels of circulating CD19+ B-cells are measured at screening and Days 15, 28, 84, 168, 364, and 728.

The pharmacokinetic (PK) objectives are to characterize the pharmacokinetics of obinutuzumab in the LN population and to assess potential PK interactions between obinutuzumab and concomitant medications, including mycophenolate mofetil (MMF). Non-linear mixed-effects modeling (with software NONMEM) is used to analyze the dose-concentration-time data of obinutuzumab. The PK profile data is used to further develop a PK model, including the effect of major covariates (e.g., sex, race/ethnicity, weight, biochemical and hematological parameters at baseline, degree of underlying disease), on the main parameters (e.g., clearance). Derivation of individual measures of exposure, such as area under the concentration-time curve (AUC) and maximum concentration observed ($C_{max}$) depend on the final PK model used. Serum obinutuzumab is summarized (mean, minimum, maximum, SD, and geometric mean) and reported.

The exploratory objectives for the study include evaluation of pre-dose levels of exploratory biomarkers (including but not limited to B-cell subsets and levels of protein and/or mRNA in serum, blood, and urine) and potential associations with outcome, evaluation of changes in exploratory biomarkers (including but not limited to B-cell subsets and levels of protein and/or mRNA in serum, blood, and urine) over time in patients dosed with obinutuzumab versus placebo, evaluation of the occurrence of extrarenal flares, evaluation of the impact of therapy on patient and physician-reported outcomes, and assessment of renal biopsy histopathology (e.g., for the presence of CD19+ B cells at the screening and/or subsequent biopsies). The exploratory outcome measures include:

(a) levels of circulating B-cell subsets at Screen and Days 15, 28, 84, 168, 364, and 728;

(b) levels of exploratory biomarkers (including but not limited to B-cell subsets and levels of protein and/or mRNA in serum, blood, and urine) at Screen and Days 1, 15, 28, 84, 168, 252, 364, 532, and 728;

(c) proportion of patients experiencing a Systemic Lupus Erythematosus Disease Activity Index (SLEDAI)-2K flare;

(d) proportion of patients experiencing a renal flare over 52 weeks and 104 weeks;

(e) proportion of patients achieving CRR, mCRR1, mCRR2 at additional timepoints (including Week 12 and 36);

(f) Physician's Global Assessment (visual analog scale captured in screening, at the baseline visit, and at several timepoints during study conduct); and (g) renal biopsy evaluations.

Laboratory, Biomarker, and Other Biological Samples

The following laboratory assessments are recorded during the study:

(a) Hematology: hemoglobin, hematocrit, RBC, mean corpuscular volume, mean corpuscular hemoglobin, WBC (absolute and differential), and quantitative platelet count;

(b) Blood chemistry: AST/SGOT, ALT/SGPT, alkaline phosphatase, amylase, lipase, total protein, albumin, cholesterol, total bilirubin, urea, uric acid, creatinine, random glucose, potassium, sodium, chloride, calcium, phosphorus, lactic dehydrogenase, CPK, and triglycerides;

(c) Urinalysis: dipstick for blood, nitrate, protein, and glucose and urine microscopy;

(d) 24-hour urine collection (analyzed for total protein, total creatinine, and creatinine clearance) to be performed at randomization and at Months 3, 6, 9, and 12;

(e) Flow cytometry: B cell (including CD19, CD27, CD38, and IgD), T cell (CD3, CD4, CD8), and NK cells (CD16, CD56);

(f) Autoantibody profile: anti-nuclear antibody (ANA), anti-dsDNA, anti-Sm, anti-RNP, anti-Ro, anti-La, and anti-C1q;

(g) Anti-dsDNA antibody: measured by ELISA at all visits as part of SLEDAI-2K assessment;

(h) Quantitative immunoglobulin: total Ig levels including IgG, IgM, and IgA isotypes;

(i) Complement: C3, C4, and CH50;

(j) Antibody titers: antibody titers to common antigens (rubella, tetanus, influenza, *S. pneumoniae*); and (k) Pregnancy test: urine pregnancy test performed at screening and prior to each study drug infusion. Infusion is not administered unless test is negative. At all other timepoints, urine pregnancy test is performed on the basis of menstrual history and pregnancy risk.

The following samples are sent for analysis: cells from blood and urine for B-cell and lupus-related biomarkers (including but not limited to CD19+ B cells and mRNA associated with B-cell activity), serum and urine for B-cell and lupus-related biomarkers (including but not limited to B-cell activating factor or BAFF), and renal biopsy slides for immunohistopathology assessment.

Infusions

Prior to each infusion of either study drug or placebo, patients receive prophylactic treatment with acetaminophen (650-1000 mg) and diphenhydramine (50 mg; or equivalent dose of a similar agent) by mouth, given 30-60 minutes before the start of the infusion period. The patients who are receiving obinutuzumab receive 80 mg methylprednisolone IV and patients who are receiving placebo receive placebo-methylprednisolone IV given 30-60 minutes before the start of the obinutuzumab/placebo infusion. If a patient experiences a mild infusion-related reaction (IRR) that is deemed by the investigator to be clinically significant, the infusion rate should be reduced to half of the initial infusion rate (in compliance with non-Hodgkin's lymphoma protocol infusion rates and schedules). After the reaction has resolved, the infusion should be kept at the reduced rate for an additional 30 minutes. If the reduced rate is tolerated, then the infusion rate may be increased to the next closest rate on the infusion schedule. Patients who experience a severe IRR should have their infusion interrupted immediately and should receive aggressive symptomatic treatment. The infusion should not be restarted until all of the symptoms have disappeared. Upon restarting the infusion, the rate should be half of that which precipitated the reaction. Instructions for administration of obinutuzumab infusions are provided in Table 6 below.

TABLE 6

Administration of obinutuzumab infusions.

| First Infusion (Day 1) | Subsequent Infusions |
|---|---|
| Begin infusion at an initial rate of 50 mg/hr.<br>If no infusion reaction occurs, increase the infusion rate in 50-mg/hr increments every 30 minutes to a maximum of 400 mg/hr.<br>If an infusion reaction develops, stop or slow the infusion. Administer infusion-reaction medications and supportive care in accordance with institutional protocol.<br>Resume the infusion at a 50% reduction in rate (the rate being used at the time that the hypersensitivity or infusion-related reaction occurred) if the reaction has resolved. | If a patient experienced an infusion reaction during the prior infusion, start at the same rate as the first infusion (50 mg/hr) and follow those directions as noted.<br>If the patient tolerated the prior infusion well, begin infusion at a rate of 100 mg/hr.<br>If no infusion reaction occurs, increase the infusion rate in 100-mg/hr increments every 30 minutes to a maximum of 400 mg/hr.<br>If an infusion reaction develops, stop or slow the infusion. Administer infusion-reaction medications and supportive care in accordance with institutional protocol.<br>Resume the infusion at a 50% reduction in rate (the rate being used at the time that the hypersensitivity or infusion-related reaction occurred) if the reaction has resolved. |

All renal biopsies and reports that are obtained as part of study entry are photomicrographed and sent to an online central reading portal for oversight of the histopathologic assessment performed by the local renal histopathologist. An expert panel assesses these biopsies and adjudicates a final interpretation. Every effort is made to complete this process while patients are in screening but is not mandatory for completion of screening activities. All new biopsies obtained during screening or during the study are processed in a manner to enable immunohistochemical staining of the tubulointerstitium for the presence of B cells. The study encourages but does not mandate the performance of repeat renal biopsies for patients that have not achieved a CRR, and seeks to enrich for study centers that perform repeat renal biopsies.

Example 2: Obinutuzumab Outperforms Rituximab at Inducing B-Cell Cytotoxicity in Rheumatoid Arthritis and Systemic Lupus Erythematosus Patient Samples Through Fc Gamma Receptor-Dependent and Independent Effector Mechanisms A proportion of Rheumatoid Arthritis (RA) and Systemic Lupus Erythematosus (SLE) patients treated with standard doses of rituximab (RTX) display inefficient B cell deletion and poor clinical responses which can be augmented by delivering higher doses, indicating that standard-dose RTX is a sub-optimal therapy in these patients. To investigate whether better responses could be achieved with other anti-CD20 mAbs, a comparison was made between RTX with Obinutuzumab (OBZ), a new-generation, glycoengineered type II anti-CD20 mAb in a series of in vitro assays measuring B cell cytotoxicity in SLE and RA samples. It was found that OBZ was at least 2-fold more efficient than RTX at inducing B-cell cytotoxicity in in-vitro whole blood assays. Dissecting this difference it was found that RTX elicited more potent complement-dependent cellular cytotoxicity (CDC) than OBZ. In contrast, OBZ was more effective at evoking Fc gamma receptor (FcγR)-mediated effector mechanisms including activation of NK cells and neutrophils. OBZ was also more efficient at inducing direct cell death. This was true for all CD19+ B-cells as a whole and in naïve (IgD+CD27−); and switched (IgD-CD27+) memory B-cells specifically, a higher frequency of which is associated with poor clinical response after RTX.

Materials and Methods

Patients

All participants of this study provided consent according to the declaration of Helsinki approved by the local research ethics committee. All patients with RA satisfied the American College of Rheumatology (ACR)/European League Against Rheumatism classification criteria (Aletaha D. et al. 2010 Ann Rheum Dis. 2010; 69 (9): 1580-8) and all patients with SLE met the ACR classification criteria (Petri M. et al. Arthritis Rheum. 2012; 64 (8): 2677-86).

Antibodies and Reagents

Anti-CD20 mAbs used in the studies included RTX, OBZ and non-glycoengineered, wild type glycosylated OBZ ($OBZ_{Gly}$) and in some experiments OBZ with a mutated Fc portion (P329G LALA) that does not engage any Fc related effector functions (Herter S. et al. Cancer Research. 2015; 75 (15 Supplement): 2460), OBZ-PG LALA. Roche Innovation Center Zürich, Switzerland generated all anti-CD20 mAbs except RTX, which was a kind gift from the pharmacy of University College Hospital, U.K. AT10, an FcγRII antagonist (Greenman J. et al. Mol Immunol. 1991; 28 (11): 1243-54), was produced in-house.

Flow Cytometry and B Cell Isolation

Fluorochrome-conjugated mAb were procured from Becton Dickinson biosciences or Biolegend, U.K.): CD3 (phycoerythrin [PE]-Cy 7), CD15 (fluorescein isothiocyanate, FITC): CD16 (Allophycocyanin, APC), CD19 (Alexa Fluor 700), CD45 (PE), CD56 (PE), CD107a (Brilliant Violet 421), CD11b (PE), CD62L (APC), propidium iodide and Annexin V (FITC). Flow cytometry was performer using a Becton Dickinson LSR Fortessa cell analyzer. Lymphocytes were identified based on forward- and side-scatter characteristics. B cells were identified as CD19+ or CD20+, T cells as CD3+ and NK cells as CD3−56+. Neutrophils were identified based on forward- and side-scatter characteristics and CD15 positivity. The mean fluorescent intensity (MFI) of CD11b and CD62L in samples incubated with mAbs was compared with that in samples incubated without antibodies.

In all experiments, peripheral blood mononuclear cells (PBMC) were separated from whole blood samples by Ficoll-Hypaque density gradient and B-cells were isolated from PBMC using EasySep™ Human B Cell Enrichment Kit (Cambridge, U.K.).

Whole Blood B-cell Depletion Assays

Briefly, 300 μl of freshly drawn whole blood anticoagulated with heparin was incubated with or without mAbs at 1 μg/mL for 24 hours at 37° C. and 5% $CO_2$. Samples were then stained with anti-CD3, anti-CD19 and anti-CD45 before lysing red cells and analyzing on flow cytometer, as described previously (Reddy V. et al. Arthritis & rheumatology. 2015; 67 (8): 2046-55). The % B-cell depletion was calculated from the proportion of B cells to T cells remaining after treatment and defined as the cytotoxicity index (CTI) as described previously (Mossner E. et al. Blood. 2010; 115 (22): 4393-402, and Reddy V. et al. Arthritis & rheumatology. 2015; 67 (8): 2046-55).

Surface Fluorescence-Quenching Assays

Surface fluorescence-quenching assays were performed as described previously (Beers S. A. et al. Blood. 2008; 112 (10): 4170-7, and Reddy V. et al. Arthritis & rheumatology. 2015; 67 (8): 2046-55) to assess internalization of mAbs by B-cells. Isolated B-cells were incubated for 6 hours with Alexa-488 conjugated mAbs at a concentration of 5 μg/mL before analyzing by flow cytometry.

Complement-Dependent Cellular Cytotoxicity Assays

CDC assays were performed as previously described (Cragg M. S. et al. Blood. 2004; 103 (7): 2738-43). Isolated B cells were incubated with mAbs at a concentration of 10 μg/mL for 30 minutes at 37° C. and 5% $CO_2$. Samples were stained with fluorescence conjugated anti-CD19 antibodies, Annexin V (Av) and propidium iodide (PI) and the frequency of CD19+Av+PI+ cells assessed by flow cytometry. Freshly collected normal healthy human serum was used as a source of complement. To define the activity relating to complement, part of the scrum was heat inactivated (HIS) at 56° C. for 30 minutes. The ability of mAbs to activate complement and lyse target cells was assessed by the relative frequency of CD19+Av+PI+ cells in samples incubated either with normal healthy serum or HIS.

Direct Cell Death

Isolated B-cells were incubated in RPMI supplemented with 10% heat inactivated foetal calf serum with or without mAbs at a concentration of 10 μg/mL for 6 hours at 37° C. and 5% $CO_2$. The frequency of CD19+Av+ cells in samples with mAbs compared with that in samples without mAbs represented the ability of mAbs to induce direct cell death.

NK Cell Degranulation Assays

NK cell degranulation was assessed using samples from the whole blood B-cell depletion assay by measuring the expression of CD107a or LAMP-1 (a lysosome associated membrane protein 1), which is up regulated upon activation of NK cells and correlates with NK cell mediated ADCC (Alter G. et al. J Immunol Methods. 2004; 294 (1-2): 15-22, and Aktas E. et al. Cell Immunol. 2009; 254 (2): 149-54). Therefore, the frequency of CD3−56+107a+ NK cells in samples with mAbs were compared with that in samples incubated without mAbs. Activation of NK cells is associated with an increased activity of metalloproteinase, which cleaves CD16 reducing its expression upon NK cell activation (Romee R. et al. Blood. 2013; 121 (18): 3599-608). Therefore the extent of CD16 loss was also used as an indirect measure of NK cell activation (Grzywacz B. et al. Leukemia. 2007; 21 (2): 356-9; author reply 9, and Bowles J. A. et al. Blood. 2006; 108 (8): 2648-54).

Neutrophil Activation Assays

Neutrophil activation was assessed in the whole blood assay by measuring increases in CD11b or decreases in CD62L on CD15+ neutrophils by flow cytometry (Golay J. et al. Blood. 2013; 122 (20): 3482-91, and Wittmann S. et al. Cytometry A. 2004; 57 (1): 53-62). The ability of mAbs to induce neutrophil activation was assessed by comparing the mean fluorescent intensity (MFI) of CD11b and CD62L on CD15+ neutrophils in samples incubated with or without mAbs.

Statistical Analysis

Data was analyzed using Graph Pad Prism Software version 5.0. Mann Whitney test or Wilcoxon matched-pairs signed rank test were used to compare between groups as appropriate. Spearman correlation coefficient was used to analyze for correlation.

Results

Type II mAbs are More Efficient than Type I at Inducing B-Cell Cytotoxicity

Figure 2B:
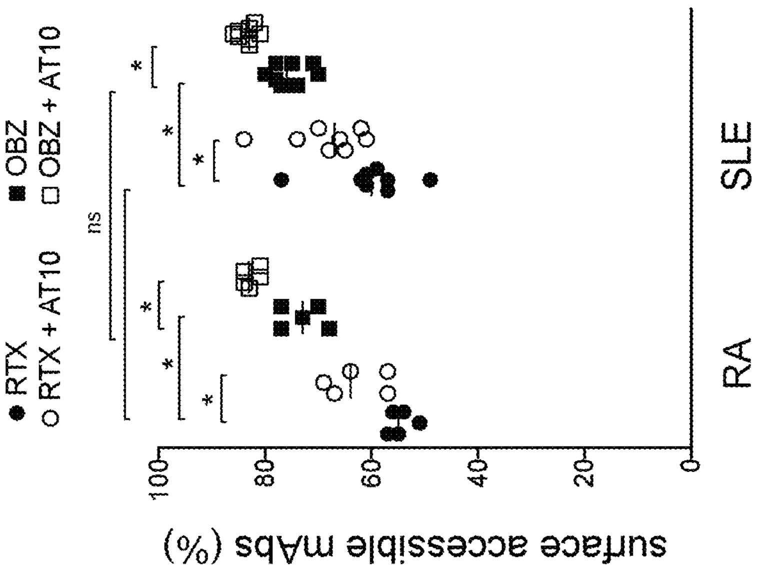
FIG. 2A-2D show whole blood B-cell-depletion, internalization and complement-dependent cellular cytotoxicity elicited by Obinutuzumab or Rituximab in RA and SLE patient samples.
Figure 2A:
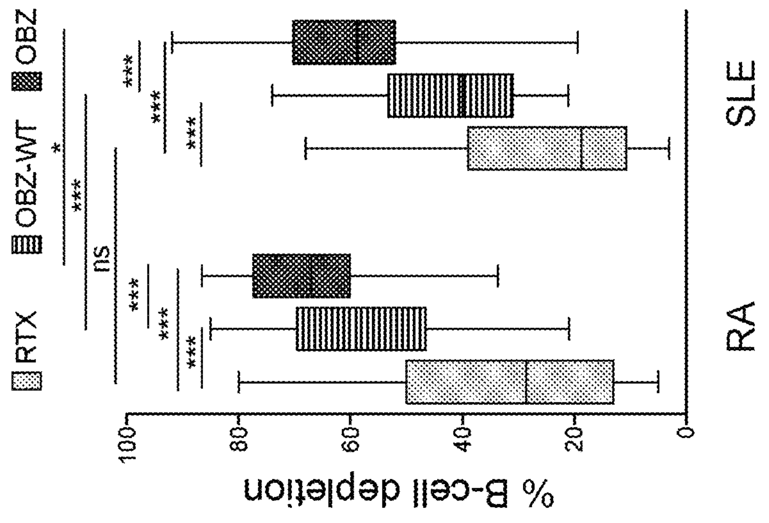

To assess the effect of Type I and II mAbs on B cell cytotoxicity in RA and SLE samples, whole blood B-cell depletion assays were performed as described previously (Reddy V. et al. Arthritis & rheumatology. 2015; 67 (8): 2046-55). OBZ was >2-fold more efficient than RTX at deleting B-cells from patients with RA (n=31) and SLE (n=34) with both non-glycomodified $OBZ_{Gly}$ and OBZ more efficient than RTX in all samples tested (FIG. 2A). In both RA and SLE, the median CTI of OBZ was significantly greater than the CTI of $OBZ_{Gly}$ and RTX and the CTI of $OBZ_{Gly}$ was significantly higher than the CTI of RTX in both RA and SLE. In RA, the median (interquartile range) CTI of RTX, $OBZ_{Gly}$ and OBZ was 29 (13-50), 60 (47-70) and 67 (60-77), respectively and in SLE was 19 (11-39), 40 (31-53) and 59 (52-70), respectively. Thus, in both RA and SLE, there was a hierarchy of mAb-induced B cell depletion: RTX<$OBZ_{Gly}$<OBZ. The remarkable inter-sample variability in B-cell depletion, particularly with RTX was also noted. The superior efficiency of $OBZ_{Gly}$ (having a non-glycomodified Fc similar to RTX) suggests that its type II nature accounts for the difference between the two types of mAbs in the efficiency of B-cell depletion in the whole blood assay; whereas the increased efficiency of OBZ compared to $OBZ_{Gly}$ is attributable to afucosylation of the Fc portion.

B-Cells Internalize RTX More Rapidly than OBZ

Next, it was investigated whether the superior efficiency of type II mAbs in B cell depletion was consistent with their type II nature, and so it assessed whether B-cells from patients with RA and SLE internalized RTX to a greater extent than OBZ. It was found that RTX internalized more extensively than OBZ after 6 hours of incubation with a median (range) percentage of surface accessible RTX vs OBZ of: 55 (51-57) versus 83 (81-84), respectively in RA (n=5); and 60 (49-77) versus 76 (70-80), respectively in SLE (n=8) (FIG. 2B). To assess the role of FcγRIIb in this internalization, experiments were performed in the presence of the FcγRII-blocking mAb AT10, which partially inhibited internalization of RTX and to a smaller extent, OBZ (FIG. 2B), similar to previous observations using a non-glycomodified Type II antibody variant of OBZ (Reddy V. et al. Arthritis & rheumatology. 2015; 67 (8): 2046-55).

Figure 2D:
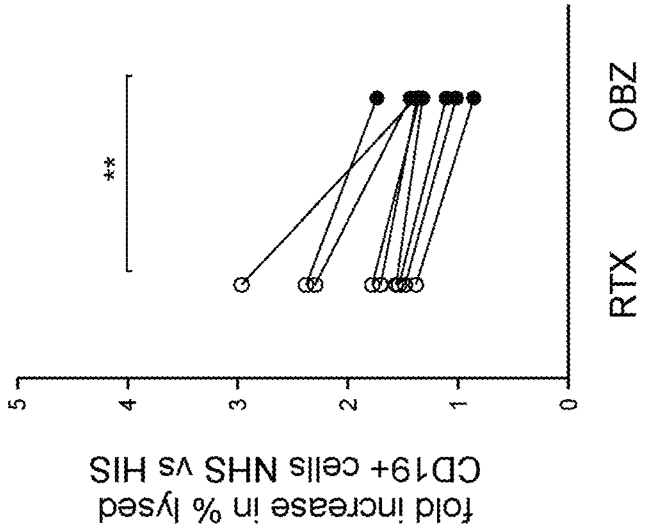
Figure 2C:
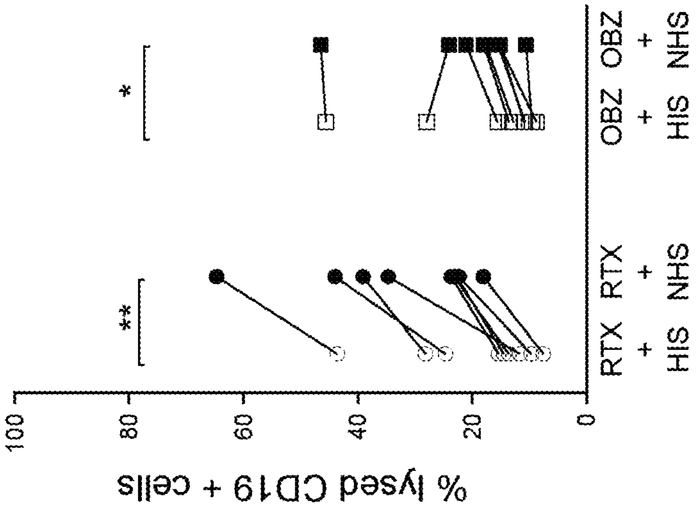

RTX is More Efficient than OBZ at Inducing Complement-Dependent Cellular Cytotoxicity The ability of these mAbs to elicit CDC was also investigated. It was found that the frequency of lysed B cells (CD19+Av+PI+) was significantly greater in samples incubated with RTX in the presence of normal healthy serum (NHS) compared to heat inactivated serum (HIS) with a median (range) difference of 10.9% (8.1-21) whereas the difference for OBZ was 4.8% (0.9-6.5) (FIG. 2C). The mean±SD fold increase in lysed cells in samples incubated with NHS vs HIS was 1.9±0.5 and 1.2±0.2 for RTX and OBZ, respectively (FIG. 2D). Thus, the data suggests that RTX was superior to OBZ at evoking CDC.

OBZ is More Efficient than RTX at Activating NK Cells

Figures 3A, 3B, 3C, 3D:
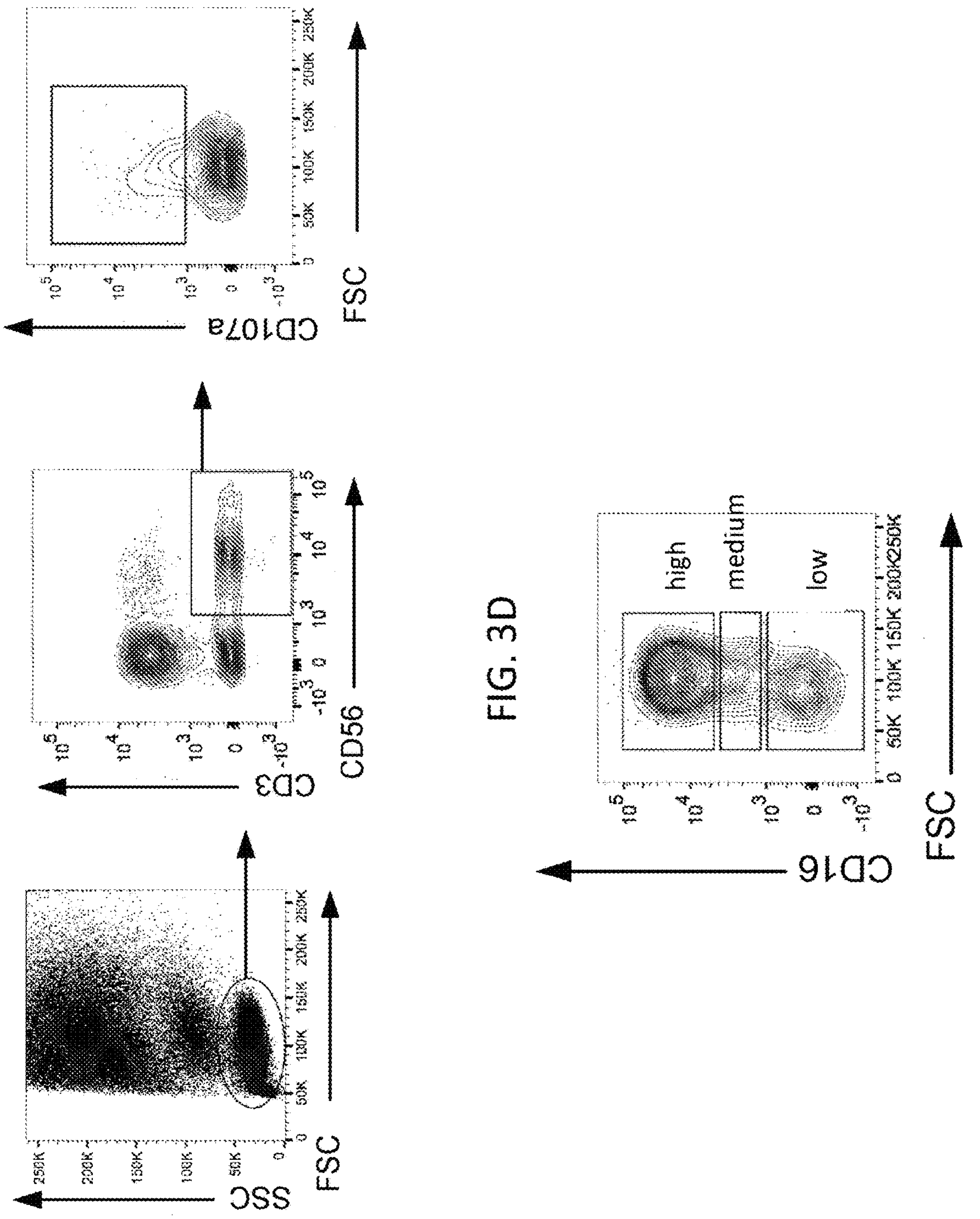
FIG. 3A-3G show the flow cytometry-gating strategy to assess NK cell degranulation, describing the relationship between NK cell expression of CD107a and CD16. Whole blood samples were incubated with or without mAbs for 24 hours before analyzing by flow cytometry. NK cells were identified based on forward- and side-scatter properties and expression of CD56 but not CD3. The frequency of CD3−CD56+CD107a+ cells represented activated/degranulated NK cells. FSC, forward-scatter; SSC, side-scatter.
Figures 3E, 3F, 3G:
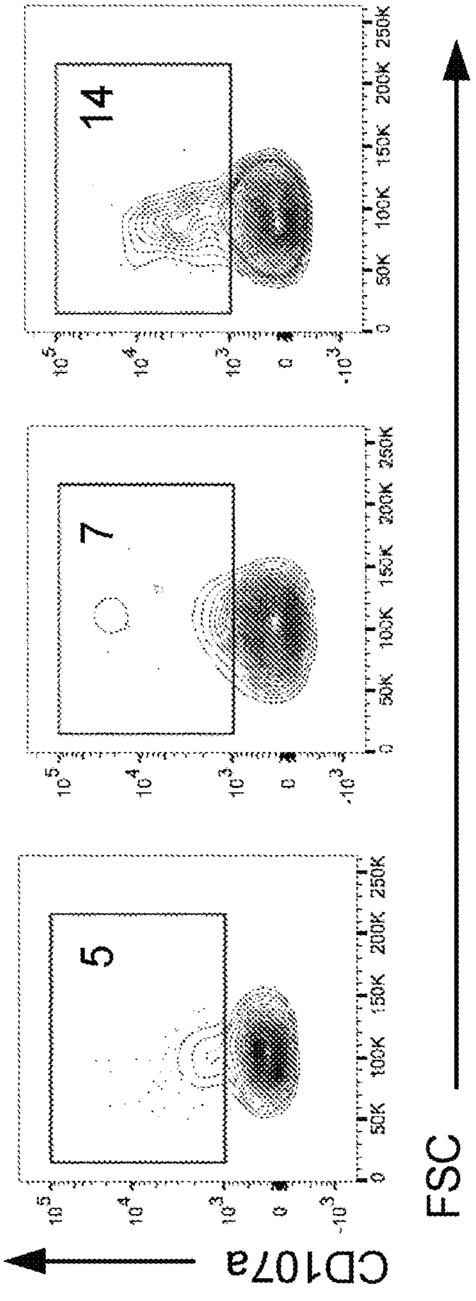

These CDC results were consistent with the type I and II nature of the mAbs but at odds with the superior efficiency of type II mAbs in the whole blood assay. Next, the ability of the mAbs to elicit FcγR-mediated effector mechanisms was investigated; first assessing NK activation in the whole blood B-cell depletion assay. Gating as indicated in FIG. 3E, allowed assessment of NK degranulation (CD107a increase) relative to expression of CD16. The highest proportion of CD107a+ NK (CD3−CD56+) cells was seen in the CD56+ CD16− fraction (FIG. 3A-3G) suggesting that degranulating NK cells had down regulated CD16 as previously reported (Grzywacz B. et al. Leukemia. 2007; 21 (2): 356-9; author reply 9).

Figure 4A:
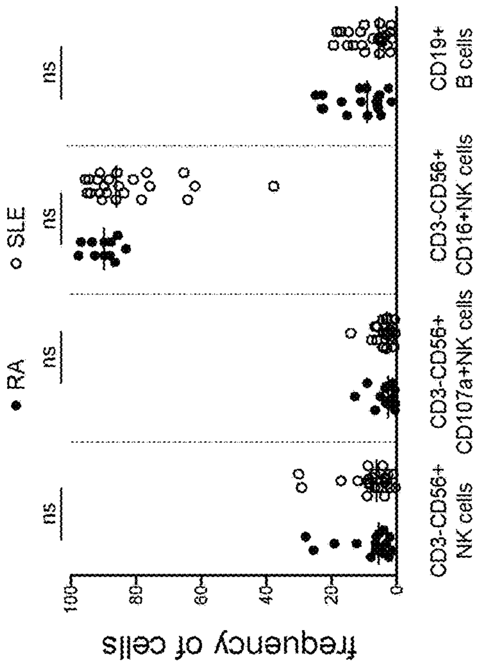
FIG. 4A-4D show that OBZ is more efficient than RTX at activating NK cells in RA and SLE patient samples. NK cell activation was assessed in whole blood samples from patients with RA (n=18) and SLE (n=23) incubated for 24 hours in the presence or absence of mAbs. *, $p<0.05$; , $p<0.005$; *, $p<0.0001$; ns, not significant and Spearman correlation coefficient, $r^2$ was considered significant when p was at least <0.05.
Figure 4B:
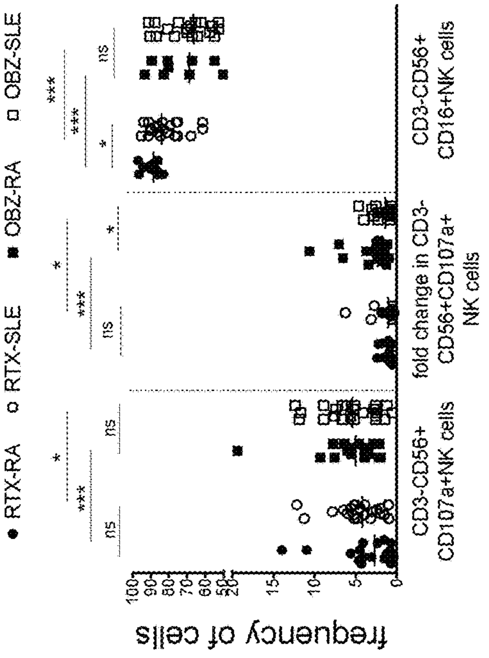
Figure 4C:
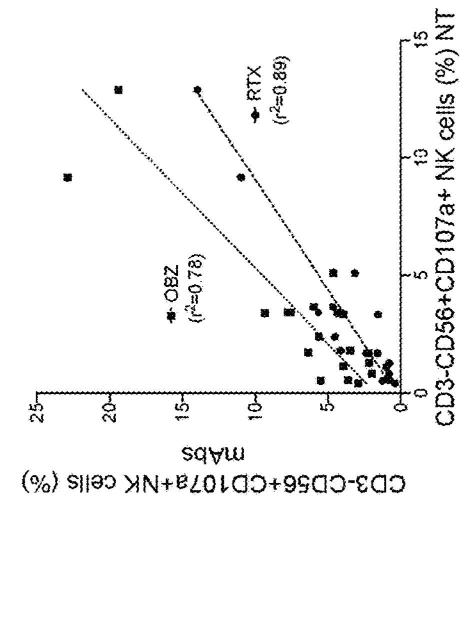
Figure 4D:
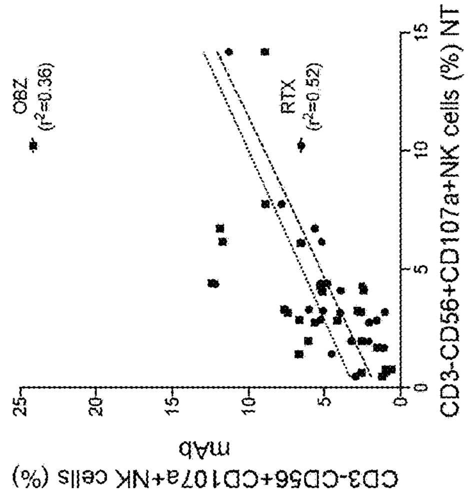

Having established these parameters, equivalent assays were performed comparing RTX and OBZ. After 24 hours of incubation in the absence of mAbs there was no significant difference in the frequency of NK cells, CD107a+ NK cells, CD16+ NK cells or B-cells between patients with RA (n=18) and SLE (n=23) (FIG. 4A). However, the median (range) frequency of CD3−CD56+CD107a+ activated NK cells was significantly higher in samples incubated with OBZ compared to RTX 5.1% (1.9-22) vs 2.8% (0.3-14) and 5.5% (0.6-12) vs 4.3% (1.2-8.9), respectively) but there was significantly lower median (range) frequency of CD16+ NK cells, in both RA and SLE 69 (36-94) vs 89 (83-97) and 66 (42-91) vs 84 (61-95), respectively (FIG. 4B). Also, there was a significantly higher fold-increase in the frequency of CD3−CD56+CD107a+ NK cells in samples incubated with OBZ compared to those incubated with RTX in SLE (FIG. 4B). Furthermore, it was found that NK cell activation, as assessed by either gain of CD107a or loss of CD16; or the fold increase in the frequency of CD3−CD56+CD107a+ NK cells, was greater in RA compared to SLE (FIG. 4B). NK cell activation, as assessed by the frequency of CD3−CD56+ CD107a+ NK cells by RTX and OBZ, correlated significantly with that in samples incubated without mAbs with $r^2$=0.89, p<0.05; $r^2$=0.78, p<0.05, respectively, in RA (FIG. 4C) and $r^2$=0.52, p<0.05; $r^2$=0.36, p<0.05, respectively, in SLE (FIG. 4D). However, correlations were stronger in RA compared to SLE. Taken together, these data suggest disease related defects in the activation of NK cells in SLE may contribute to inefficient B-cell depletion noted in whole blood depletion assays (FIG. 2A) and that baseline activation status of NK cells may influence response to activation by mAbs in both RA and SLE (FIGS. 4B and 4C).

Figure 5A:
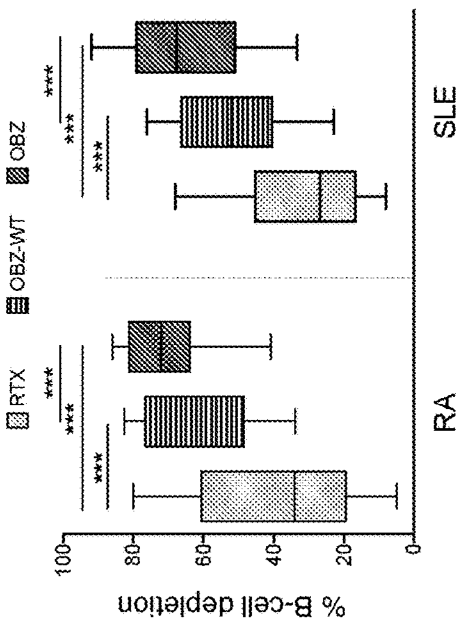
FIG. 5A-5D show that Obinutuzumab is more efficient than Rituximab at evoking NK cell-mediated cellular cytotoxicity in RA and SLE patient samples.
Figure 5B:
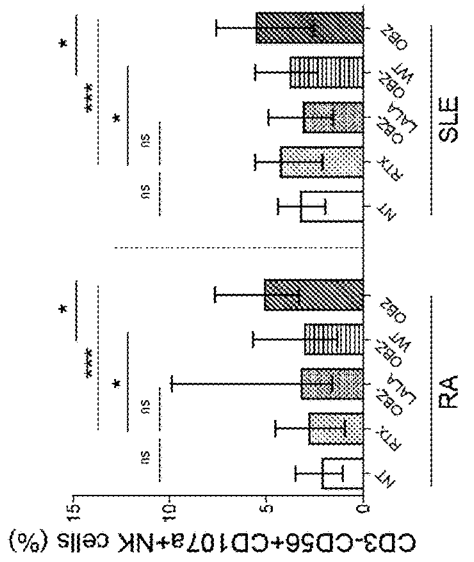
Figure 5C:
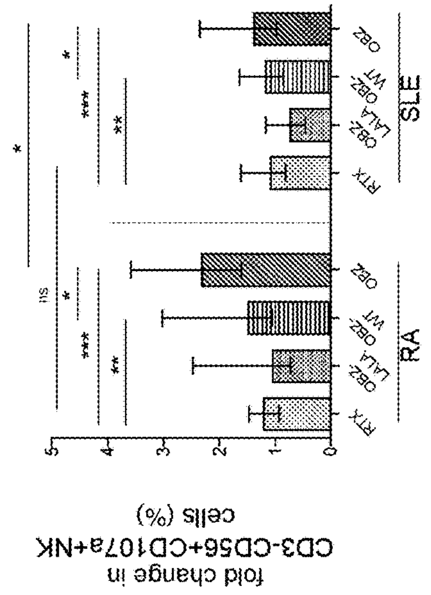
Figure 5D:
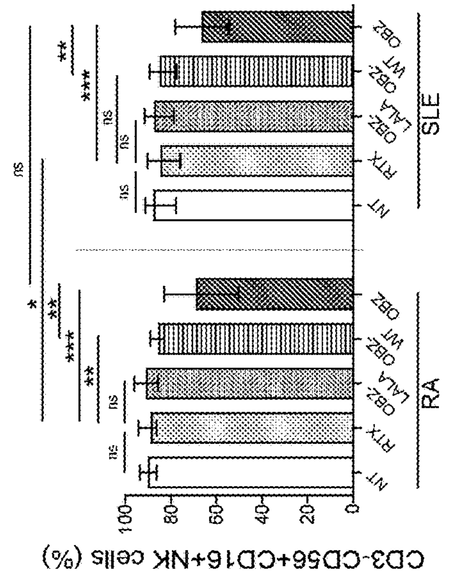

It was next investigated whether differential activation of NK cells by RTX and OBZ was due to type I and type II characteristics and/or due to the effect of Fc engineering using either OBZ with wild-type glycosylation ($OBZ_{Gly}$) or completely lacking FcγR engagement (OBZ-PG LALA), consequently, less/in-efficient at inducing ADCC and CDC (Hessell A. J. et al. Nature. 2007; 449 (7158): 101-4). Significant differences were not found in the frequency of CD3−CD56+CD107a+ or CD3−CD56+CD16+ NK cells in samples incubated without mAbs compared to samples incubated with OBZ-PG LALA in both RA (n=6) and SLE (n=12) showing that FcγR-engagement is essential as expected. In these samples also OBZ was more efficient than $OBZ_{Gly}$ and RTX at depleting B cells in the whole blood assay in both RA (n=18) and SLE (n=23) (FIG. 5A), but an increasing hierarchy was noted in the frequency of, and fold-increase in, CD3−CD56+CD107a+ NK cells as follows: no mAbs=OBZ-PG LALA<RTX<OBZ (FIGS. 5B and 5C). The frequency of CD3−CD56+CD16+ NK cells was significantly lower in samples incubated with OBZ when compared with other samples (FIG. 5D). The frequency of CD3−CD56+CD16+ NK cells was also lower in samples incubated with $OBZ_{Gly}$ compared to RTX in RA, but not SLE (FIG. 5D).

Thus, the ability of mAbs to up-regulate the expression of CD107a on CD3−CD56+ NK cells was greater in RA compared with SLE, such that the mean fold difference in samples incubated with RTX, OBZ-PG LALA, $OBZ_{Gly}$ and OBZ when compared with samples incubated without mAbs was 1.2, 1.5, 1.9 and 3.1, respectively, in RA and 1.5, 0.8, 1.4 and 1.8, respectively, in SLE (FIG. 5C). Although the pattern of B-cell depletion achieved by mAbs in RA and SLE (FIG. 5A) was similar to the pattern of NK cell activation by mAbs (FIGS. 5B and 5D) there was no direct correlation between % B-cell depletion achieved by mAbs and the frequency of CD3−CD56+CD107a+ NK cells in individual samples (data not shown).

OBZ is More Efficient than RTX at Activating Neutrophils

Figure 6A:
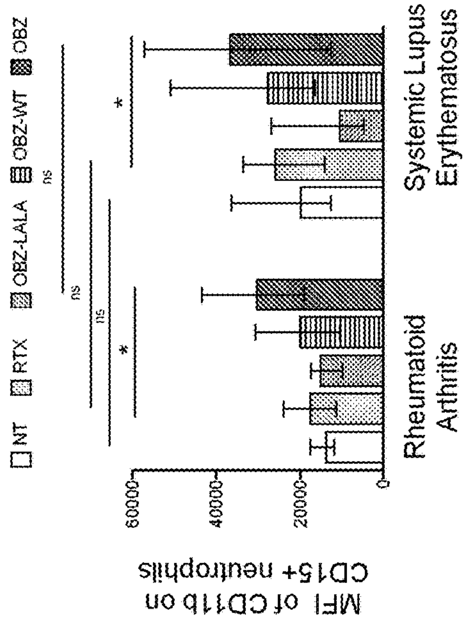
FIG. 6A-6D show that Obinutuzumab is more efficient than Rituximab at activating neutrophils in RA and SLE patient samples.
Figure 6B:
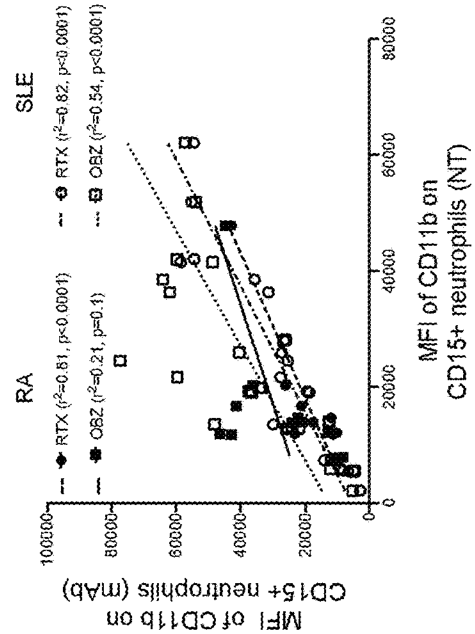
Figure 6C:
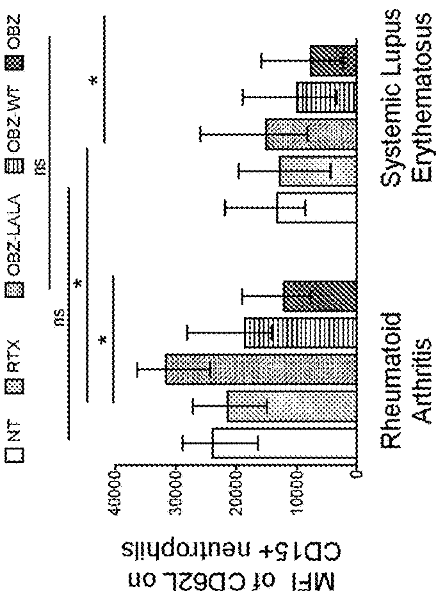
Figure 6D:
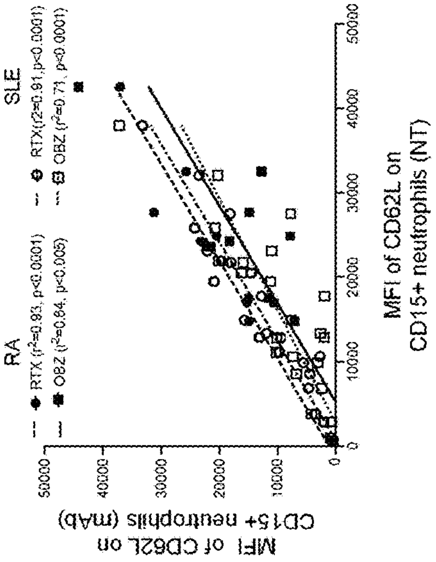
Figure 9:
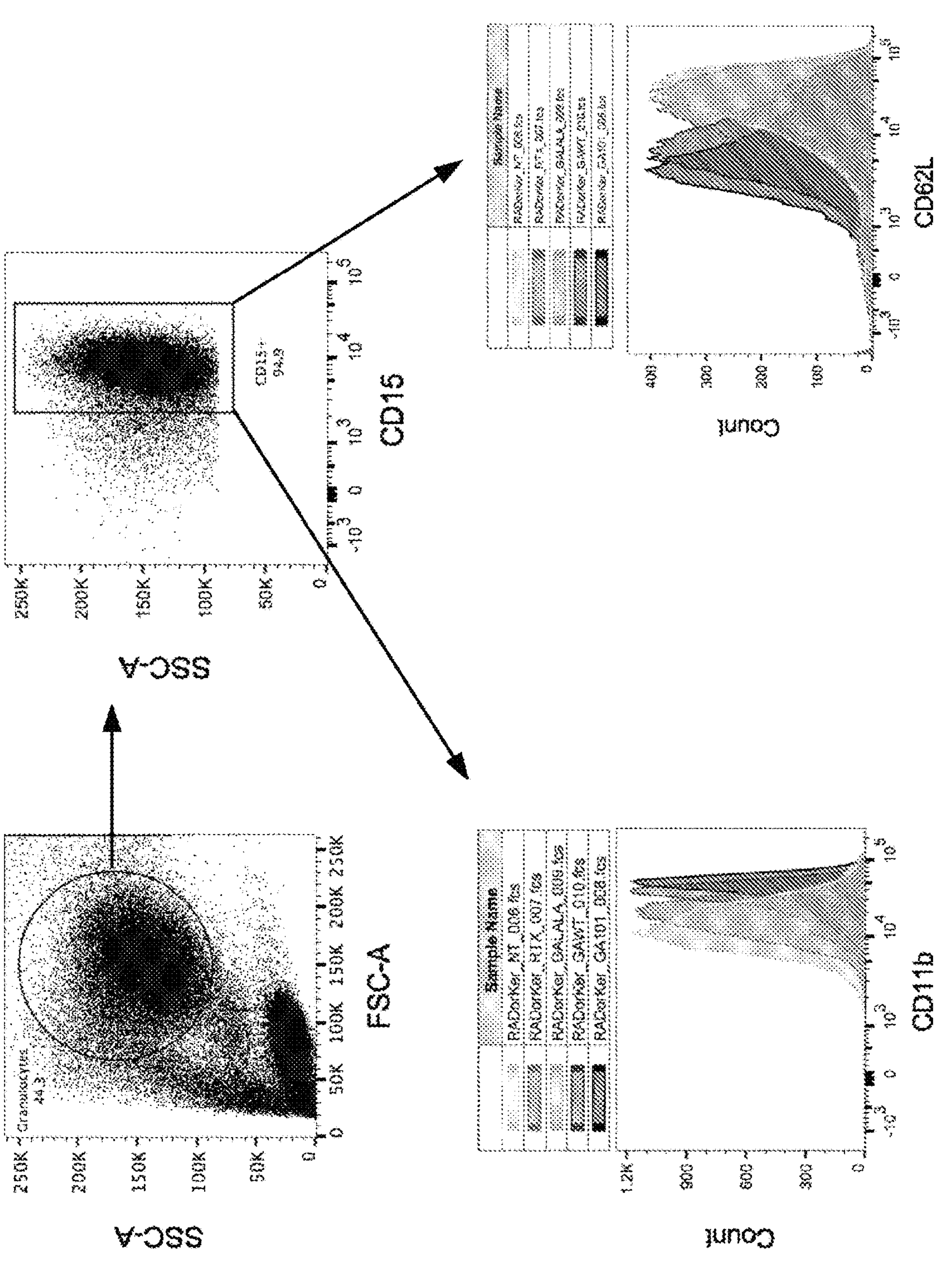
FIG. 9 shows the flow cytometry-gating strategy to assess neutrophil activation. After 24 hours of incubation, whole blood samples were analysed by flow cytometry. Neutrophils were identified by forward- and side-scatter and CD15 positivity. The mean fluorescence intensity of CD11b and CD62L was analyzed on gated neutrophils positive for CD15.

In addition to NK cells, neutrophils have also been proposed as mAb effector cells (Golay J. et al. Blood. 2013; 122 (20): 3482-91). Therefore, next, the ability of mAbs to induce neutrophil activation was assessed by measuring the expression of CD11b and CD62L, as described previously (Wittmann S. et al. Cytometry A. 2004; 57 (1): 53-62) and shown in FIG. 9. CD11b forms part of the β integrin (Mac-1) complex and several genetic variants of this complex have been associated with lupus-related phagocytic defects (Bologna L. et al. J Immunol. 2011; 186 (6): 3762-9). Upon neutrophil activation the surface expression of CD11b is up regulated whereas the expression of the adhesion molecule CD62L is down regulated (Golay J. et al. Blood. 2013; 122 (20): 3482-91, and Wittmann S. et al. Cytometry A. 2004; 57 (1): 53-62). It was found that the MFI of CD11b in samples incubated with mAbs was significantly higher in both RA (n=10) and SLE (n=22) (FIG. 6A) when compared with samples incubated without mAbs. In both RA and SLE, significant correlations were noted between the MFI of CD11b in samples incubated in the absence of mAbs and that in samples incubated with RTX ($r^2$=0.81, 0.82, respectively) whereas significant correlation for OBZ was noted in SLE ($r^2$=0.81), but not RA (FIG. 6B). A hierarchy was also noted in the ability of mAbs to up-regulate CD11b such that the MFI of CD11b was lower in samples incubated with RTX<$OBZ_{Gly}$<OBZ, as in the case of NK cell activation. Also, the MFI of CD62L was greater in samples incubated with RTX>$OBZ_{Gly}$>OBZ (FIG. 6C). In both RA and SLE, significant correlations were noted between the MFI of CD62L in samples incubated in the absence of mAbs and that in samples incubated with RTX ($r^2$=0.93, 0.91, respectively) and OBZ ($r^2$=0.64, 0.71, respectively) (FIG. 6D). Thus, the hierarchy of mAbs in their ability to activate neutrophils was OBZ>$OBZ_{Gly}$>RTX. Taken together, these data suggested that type II mAbs are superior to RTX in activating neutrophils in the whole blood assay for both RA and SLE samples. OBZ-PG LALA did not elicit significant changes for either marker in both RA (n=7) and SLE (n=12) compared to samples incubated in the absence of mAbs.

OBZ is More Efficient than RTX at Inducing Direct Cell Death

Figure 7A:
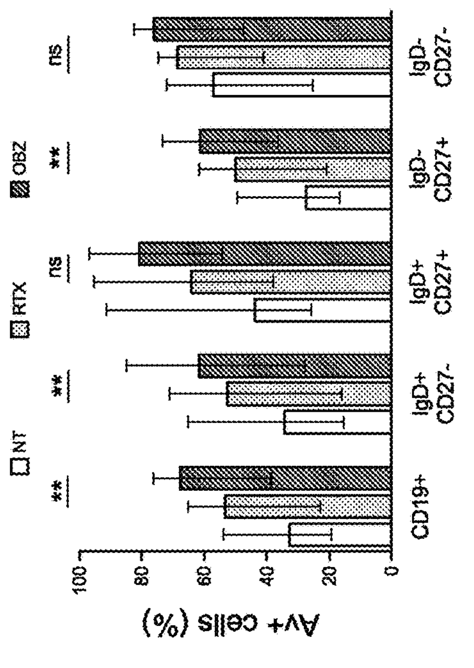
FIG. 7A-7D show assessment of direct cell death, internalization and expression of CD20 and FcγRIIb in B-cell subpopulations from RA and SLE samples.
Figure 7B:
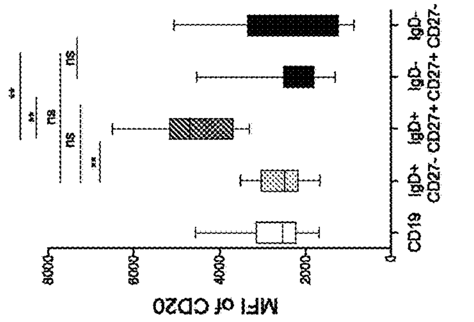
Figure 7C:
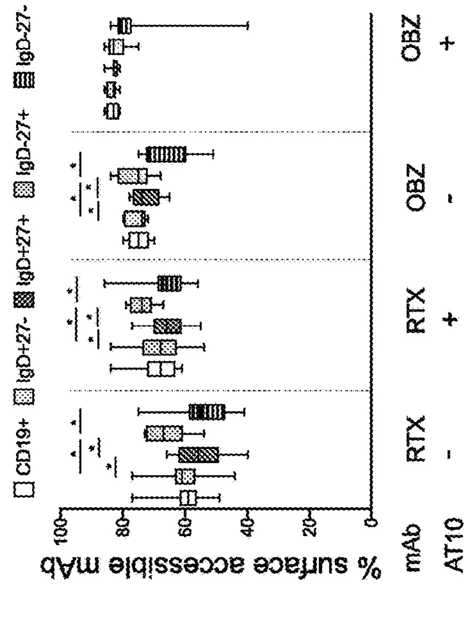
Figure 7D:
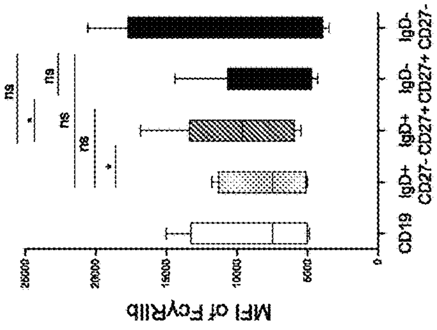
Figure 8:
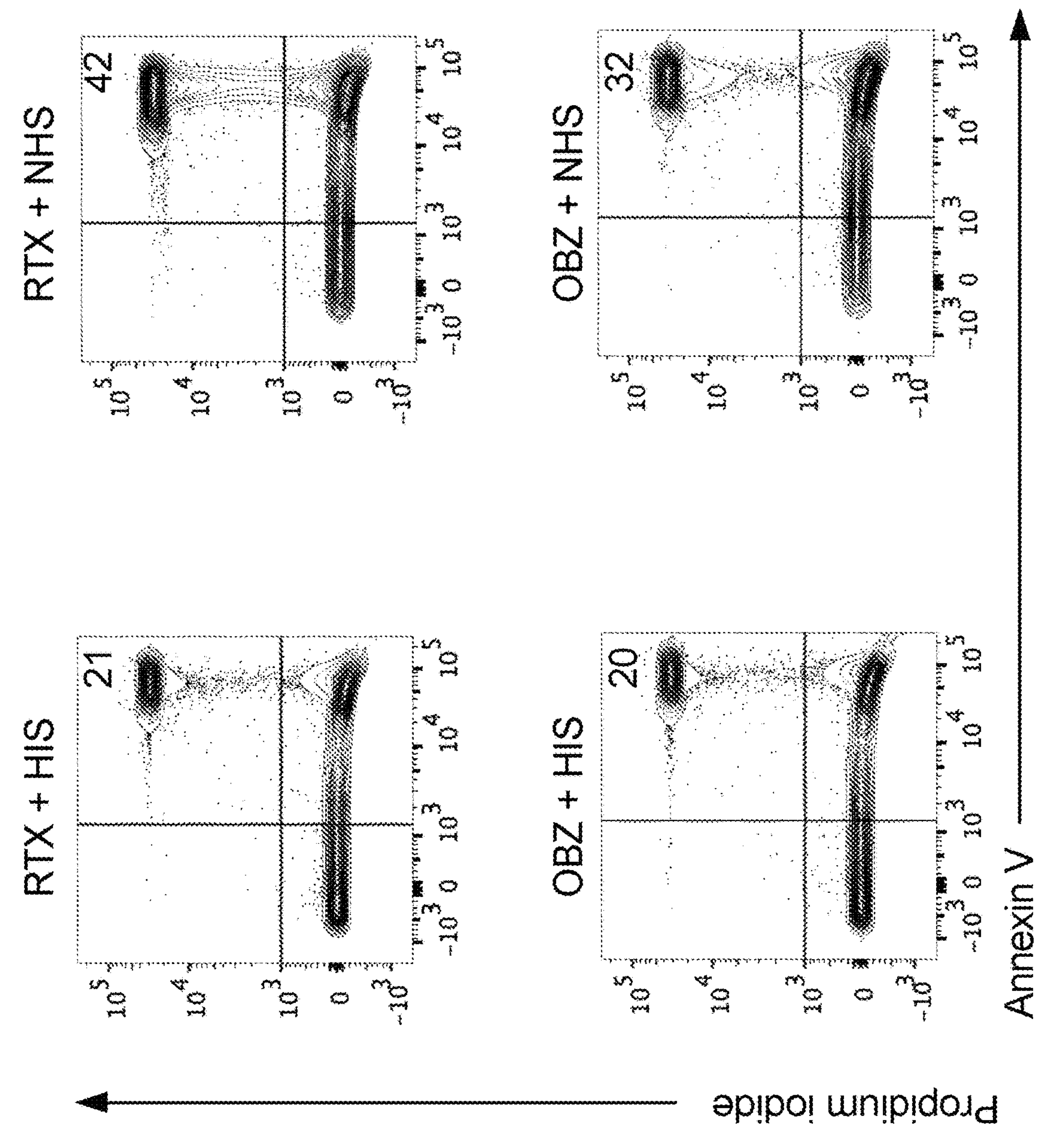
FIG. 8 shows the gating strategy for the complement-dependent cytotoxicity assay, and CDC by RTX and OBZ. Isolated B cells were incubated with mAbs either with NHS or HIS for 30 minutes at room temperature before analyzing by flow cytometry. The frequency of An V+ PI+ cells represented cell death. HIS, heat inactivated serum; NHS, normal healthy serum; RTX, rituximab; OBZ, Obinutuzumab; An V, Annexin V and PI, propidium iodide.
Figure 10:
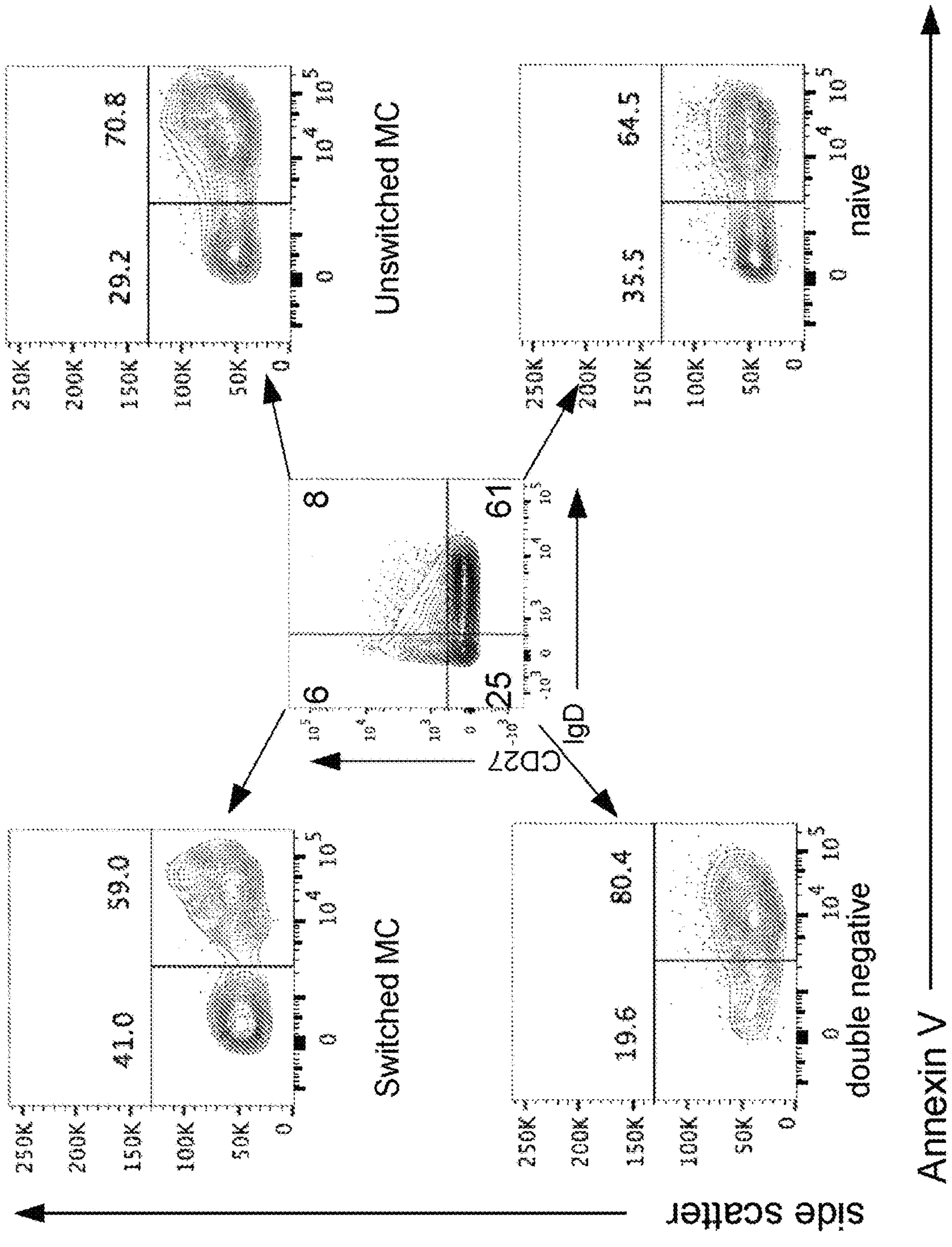
FIG. 10 shows the flow cytometry-gating strategy to assess direct cell death. After 6 hours of incubation with or without mAbs at 37° C. and 5% $CO_2$, isolated B-cells were analyzed by flow cytometry. CD19+ B-cells were categorized into naïve (IgD+CD27−), unswitched memory cells (IgD+CD27+), switched memory cells (IgD-CD27+) and double negative cells (IgD-CD27−). The frequency of Annexin V+ cells represented direct cell death.
Figure 11:
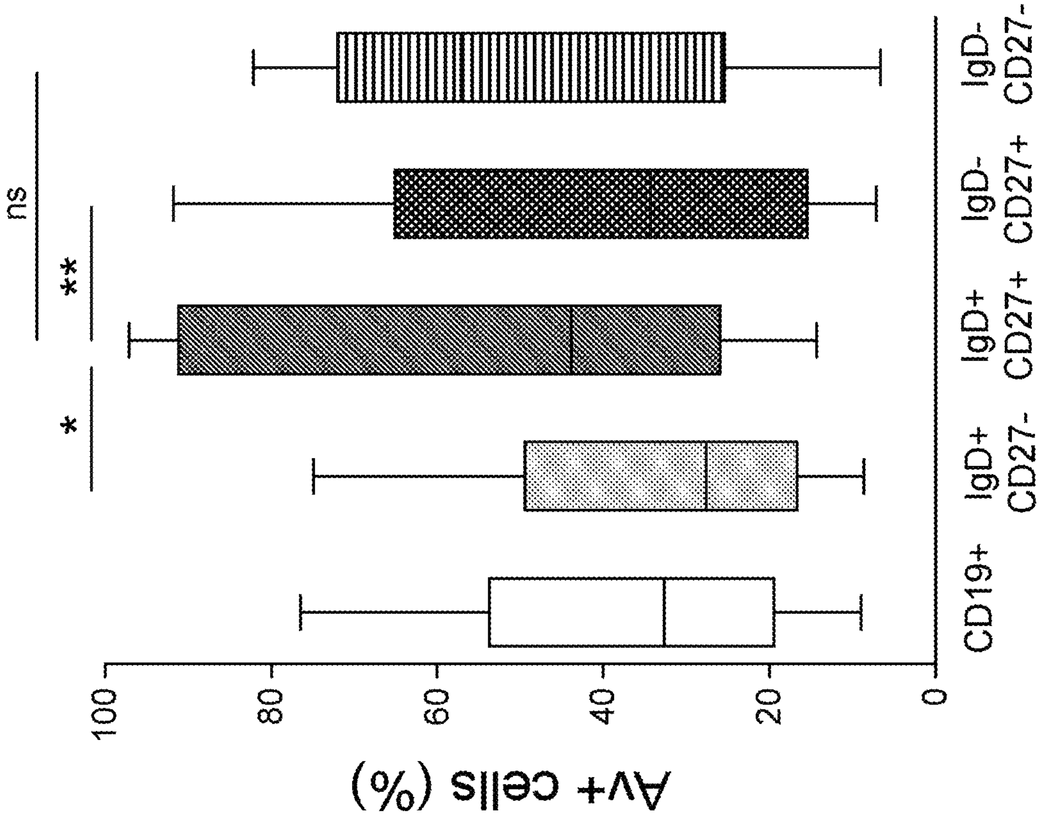
FIG. 11 shows the inherent susceptibility to spontaneous cell death in B-cell subpopulations. Isolated B-cells incubated in RPMI supplemented with 10% foetal calf serum for 6 hours at at 37° C. and 5% $CO_2$ were analyzed by flow cytometry. The frequency of Annexin V+ cells represented direct cell death in CD19+ cells as a whole and also in B-cell subpopulations categorized into naïve (IgD+CD27−), unswitched memory cells (IgD+CD27+), switched memory cells (IgD-CD27+) and double negative cells (IgD-CD27−). Av, Annexin V; * $p<0.05$; ***, $p<0.0001$; ns, not significant.

Next, direct cell death (DCD) was assessed, using the Annexin V assay as shown in FIG. 10. The ability of OBZ to induce direct cell death was greater than that of RTX for both CD19+ cells as a whole and also B-cell subpopulations; IgD+CD27− naïve cells and IgD-CD27+ switched memory cells, FIG. 7A (RA, n=5 and SLE, n=4). The proportion of Annexin V+ cells was highest for DN cells >IgD+CD27+ unswitched memory cells >IgD-CD27+ switched memory cells >IgD+CD27− naïve cells, even in samples incubated without mAbs. Nonetheless, OBZ was superior to RTX at inducing DCD.

B-Cell Subpopulations: Expression of CD20, FcγRIIb and Internalization of mAbs

It was next investigated whether differences between B-cell subpopulations in the expression of CD20, FcγRIIb and/or their ability to internalize mAbs provided explanations for the differential sensitivity to mAb-induced DCD. B-cell subpopulations displayed varying ability to internalize mAbs such that IgD-CD27+ switched memory cells internalized mAbs less than other B-cell subpopulations; and IgD+CD27+ unswitched memory cells internalized mAbs to a greater extent than other B-cell subpopulations. Antagonizing the effects of FcγRIIb with AT10 significantly reduced internalization in both cases. When compared to naïve and IgD-CD27+ switched memory cells, IgD+CD27+ unswitched memory cells had significantly greater expression of CD20 and FcγRIIb and displayed significantly greater ability to internalize mAbs whereas naïve and IgD-CD27+ switched memory cells had significantly lower expression of CD20 and FcγRIIb and displayed significantly lower levels of internalization. DN cells had remarkably variable levels of expression of CD20 and FcγRIIb, but internalized RTX to a significantly greater extent than IgD-CD27+ switched memory cells. B cells from both RA and SLE samples consistently displayed low levels of OBZ internalization. Taking these data together, there was no clear relationship between the susceptibility of B-cell subpopulations to mAb-induced DCD and the ability to internalize mAbs or to express CD20 or FcγRIIb.

Here, it was shown that Obinutuzumab, a type II anti-CD20 mAb with a glycomodified Fc demonstrated at least 2-fold greater potency at deleting B-cells from whole blood samples of patients with both RA and SLE compared to the RTX. This increased activity of OBZ was affected predominantly through Fc gamma receptor (FcγR)-mediated effector mechanisms and DCD. In contrast, RTX recruited complement more efficiently for CDC, but was rapidly internalized and significantly less efficient at evoking ADCC and DCD. The subsequent analysis revealed that the expression of the CD20 target molecule was less on IgD-CD27+ switched memory and DN cells; perhaps accounting for their relative resistance to removal by RTX.

What is claimed is:

1. A method for treating lupus nephritis in an individual that has active lupus nephritis, comprising administering to the individual at least a first antibody exposure to obinutuzumab and a second antibody exposure to obinutuzumab;

wherein the first antibody exposure comprises two doses of obinutuzumab administered about 2 weeks apart, wherein both doses of the first antibody exposure are about 1000 mg of obinutuzumab administered intravenously;

wherein the second antibody exposure comprises two doses of obinutuzumab administered about 2 weeks apart, wherein both doses of the second antibody exposure are about 1000 mg of obinutuzumab administered intravenously;

wherein the first dose of the second antibody exposure is not provided until about 24 weeks after the first dose of the first antibody exposure; and wherein the individual is a human.

2. The method of claim 1, wherein the individual has class III or class IV lupus nephritis.

3. The method of claim 2, wherein the individual has concomitant class V lupus nephritis.

4. The method of claim 1, further comprising administering to the individual an effective amount of an immunosuppressive agent.

5. The method of claim 4, wherein the immunosuppressive agent comprises mycophenolic acid, a derivative thereof, or a salt thereof.

6. The method of claim 4, wherein the immunosuppressive agent comprises mycophenolate mofetil (MMF).

7. The method of claim 1, further comprising administering to the individual an effective amount of a glucocorticoid or corticosteroid.

8. The method of claim 7, wherein the glucocorticoid or corticosteroid comprises methylprednisolone or prednisone.

9. The method of claim 1, further comprising administering to the individual a standard of care treatment.

10. The method of claim 9, wherein the standard of care treatment comprises treatment with one or more of an angiotensin-converting enzyme (ACE) inhibitor, an angiotensin-receptor blocker, cyclophosphamide, mycophenolate mofetil (MMF), azathioprine, and a glucocorticoid or corticosteroid.

11. The method of claim 1, wherein the method results in a complete renal response (CRR) in the individual.

12. The method of claim 11, wherein the method results in the individual achieving a urinary protein to creatinine ratio (UPCR) of <0.5 g/g.

13. A method for treating lupus nephritis in an individual that has active class III or class IV lupus nephritis, comprising administering to the individual: (a) at least a first antibody exposure to obinutuzumab and a second antibody exposure to obinutuzumab, and (b) a standard of care treatment;

wherein the first antibody exposure comprises two doses of obinutuzumab administered about 2 weeks apart, wherein both doses of the first antibody exposure are about 1000 mg of obinutuzumab administered intravenously;

wherein the second antibody exposure comprises two doses of obinutuzumab administered about 2 weeks apart, wherein both doses of the second antibody exposure are about 1000 mg of obinutuzumab administered intravenously;

wherein the first dose of the second antibody exposure is not provided until about 24 weeks after the first dose of the first antibody exposure; and wherein the individual is a human.

14. The method of claim 13, wherein the standard of care treatment comprises treatment with one or more of an angiotensin-converting enzyme (ACE) inhibitor, an angiotensin-receptor blocker, cyclophosphamide, mycophenolate mofetil (MMF), azathioprine, and a glucocorticoid or corticosteroid.

15. The method of claim 14, wherein the standard of care treatment comprises treatment with MMF and oral prednisone.

16. The method of claim 13, further comprising, prior to intravenous administration of one or more doses of obinutuzumab, administering to the individual an effective amount of: a glucocorticoid or corticosteroid, an antihistamine, and a non-steroidal anti-inflammatory drug (NSAID).

17. The method of claim 16, wherein the glucocorticoid or corticosteroid is methylprednisolone, the antihistamine is diphenhydramine, and the NSAID is acetaminophen.

18. The method of claim 17, further comprising, prior to intravenous administration of one or more doses of obinutuzumab, administering to the individual: 80 mg methylprednisolone, 50 mg diphenhydramine, and 650-1000 mg acetaminophen.

19. The method of claim 13, wherein the first dose of the first antibody exposure is administered intravenously to the individual starting at a rate of 50 mg obinutuzumab/hour and increasing in 50 mg obinutuzumab/hour increments every 30 minutes to a maximum of 400 mg obinutuzumab/hour.

20. The method of claim 19, wherein the second dose of the first antibody exposure and both doses of the second antibody exposure are administered intravenously to the individual starting at a rate of 100 mg obinutuzumab/hour and increasing in 100 mg obinutuzumab/hour increments every 30 minutes to a maximum of 400 mg obinutuzumab/hour.

21. A method for treating lupus nephritis in an individual that has active class III or class IV lupus nephritis, comprising administering to the individual: (a) at least a first antibody exposure to obinutuzumab and a second antibody exposure to obinutuzumab, (b) mycophenolate mofetil (MMF), and (c) a glucocorticoid or corticosteroid;

wherein the first antibody exposure comprises two doses of obinutuzumab administered about 2 weeks apart, wherein both doses of the first antibody exposure are about 1000 mg of obinutuzumab administered intravenously;

wherein the second antibody exposure comprises two doses of obinutuzumab administered about 2 weeks apart, wherein both doses of the second antibody exposure are about 1000 mg of obinutuzumab administered intravenously;

wherein the first dose of the second antibody exposure is not provided until about 24 weeks after the first dose of the first antibody exposure;

wherein the individual is a human; and wherein the method results in the individual achieving a urinary protein to creatinine ratio (UPCR) of <0.5 g/g.

22. The method of claim 21, wherein the glucocorticoid or corticosteroid is methylprednisolone or prednisone.

23. The method of claim 21, wherein the glucocorticoid or corticosteroid is oral prednisone.

24. The method of claim 10, wherein the standard of care treatment comprises treatment with MMF and oral prednisone.

25. The method of claim 21, further comprising, prior to intravenous administration of one or more doses of obinutuzumab, administering to the individual an effective amount of: a glucocorticoid or corticosteroid, an antihistamine, and a non-steroidal anti-inflammatory drug (NSAID).

26. The method of claim 25, wherein the glucocorticoid or corticosteroid is methylprednisolone, the antihistamine is diphenhydramine, and the NSAID is acetaminophen.

27. The method of claim 26, further comprising, prior to intravenous administration of one or more doses of obinutuzumab, administering to the individual: 80 mg methylprednisolone, 50 mg diphenhydramine, and 650-1000 mg acetaminophen.

28. The method of claim 21, wherein the first dose of the first antibody exposure is administered intravenously to the individual starting at a rate of 50 mg obinutuzumab/hour and increasing in 50 mg obinutuzumab/hour increments every 30 minutes to a maximum of 400 mg obinutuzumab/hour.

29. The method of claim 28, wherein the second dose of the first antibody exposure and both doses of the second antibody exposure are administered intravenously to the individual starting at a rate of 100 mg obinutuzumab/hour and increasing in 100 mg obinutuzumab/hour increments every 30 minutes to a maximum of 400 mg obinutuzumab/hour.

30. The method of claim 1, further comprising, prior to intravenous administration of one or more doses of obinutuzumab, administering to the individual an effective amount of: a glucocorticoid or corticosteroid, an antihistamine, and a non-steroidal anti-inflammatory drug (NSAID).

31. The method of claim 30, wherein the glucocorticoid or corticosteroid is methylprednisolone, the antihistamine is diphenhydramine, and the NSAID is acetaminophen.

32. The method of claim 31, further comprising, prior to intravenous administration of one or more doses of obinutuzumab, administering to the individual: 80 mg methylprednisolone, 50 mg diphenhydramine, and 650-1000 mg acetaminophen.

33. The method of claim 1, wherein the first dose of the first antibody exposure is administered intravenously to the individual starting at a rate of 50 mg obinutuzumab/hour and increasing in 50 mg obinutuzumab/hour increments every 30 minutes to a maximum of 400 mg obinutuzumab/hour.

34. The method of claim 33, wherein the second dose of the first antibody exposure and both doses of the second antibody exposure are administered intravenously to the individual starting at a rate of 100 mg obinutuzumab/hour and increasing in 100 mg obinutuzumab/hour increments every 30 minutes to a maximum of 400 mg obinutuzumab/hour.

35. A method for treating lupus nephritis in an individual that has active lupus nephritis, comprising administering to the individual at least four intravenous infusions of obinutuzumab;

wherein each infusion comprises 1,000 mg of obinutuzumab;

wherein the infusions are administered at weeks 0, 2, 24, and 26; and wherein the individual is a human.

36. The method of claim 35, wherein the method results in the individual achieving a urinary protein to creatinine ratio (UPCR) of <0.5 g/g.

37. The method of claim 35, wherein the method results in a complete renal response (CRR) in the individual.

38. The method of claim 35, wherein the method results in (a) a normalization of serum creatinine, (b) an inactive urinary sediment, and (c) a urinary protein to creatinine ratio of <0.5; wherein:

(i) the normalization of serum creatinine is characterized by serum creatinine less than or equal to the upper limit of normal (ULN) range of central laboratory values, and/or serum creatinine ≤15% above baseline and less than or equal to the ULN range of central laboratory values if the individual's baseline serum creatinine is within the normal range of the central laboratory values; and wherein (ii) the inactive urinary sediment is characterized by fewer than 10 red blood cells per high power field and/or absence of red cell casts.

39. The method of claim 35, further comprising administering to the individual an effective amount of an immunosuppressive agent.

40. The method of claim 39, wherein the immunosuppressive agent comprises mycophenolic acid, a derivative thereof, or a salt thereof.

41. The method of claim 39, wherein the immunosuppressive agent comprises mycophenolate mofetil (MMF).

42. The method of claim 35, further comprising administering to the individual an effective amount of a glucocorticoid or corticosteroid.

43. The method of claim 42, wherein the glucocorticoid or corticosteroid comprises methylprednisolone or prednisone.

44. The method of claim 35, further comprising administering to the individual a standard of care treatment.

45. The method of claim 44, wherein the standard of care treatment comprises treatment with one or more of an angiotensin-converting enzyme (ACE) inhibitor, an angiotensin-receptor blocker, cyclophosphamide, mycophenolate mofetil (MMF), azathioprine, and a glucocorticoid or corticosteroid.

46. The method of claim 45, wherein the standard of care treatment comprises treatment with MMF and oral prednisone.

47. The method of claim 35, further comprising, prior to infusion of one or more doses of obinutuzumab, administering to the individual an effective amount of: a glucocorticoid or corticosteroid, an antihistamine, and a non-steroidal anti-inflammatory drug (NSAID).

48. The method of claim 47, wherein the glucocorticoid or corticosteroid is methylprednisolone, the antihistamine is diphenhydramine, and the NSAID is acetaminophen.

49. The method of claim 48, further comprising, prior to infusion of one or more doses of obinutuzumab, administering to the individual: 80 mg methylprednisolone, 50 mg diphenhydramine, and 650-1000 mg acetaminophen.

50. The method of claim 35, wherein the first dose of the first infusion is administered to the individual starting at a rate of 50 mg obinutuzumab/hour and increasing in 50 mg obinutuzumab/hour increments every 30 minutes to a maximum of 400 mg obinutuzumab/hour.

51. The method of claim 50, wherein the second, third and fourth infusions are administered to the individual starting at a rate of 100 mg obinutuzumab/hour and increasing in 100 mg obinutuzumab/hour increments every 30 minutes to a maximum of 400 mg obinutuzumab/hour.

* * * * *

SEQUENCE LISTING

```
Sequence total quantity: 43
SEQ ID NO: 1            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 1
GYAFSY                                                              6

SEQ ID NO: 2            moltype = AA  length = 8
FEATURE                 Location/Qualifiers
REGION                  1..8
                        note = Synthetic Construct
source                  1..8
                        mol_type = protein
                        organism = synthetic construct
SEQUENCE: 2
FPGDGDTD                                                            8

SEQ ID NO: 3            moltype = AA  length = 10
FEATURE                 Location/Qualifiers
REGION                  1..10
                        note = Synthetic Construct
```

-continued

```
source                  1..10
                        mol_type = protein
                        organism = synthetic construct
SEQUENCE: 3
NVFDGYWLVY                                                  10

SEQ ID NO: 4            moltype = AA  length = 16
FEATURE                 Location/Qualifiers
REGION                  1..16
                        note = Synthetic Construct
source                  1..16
                        mol_type = protein
                        organism = synthetic construct
SEQUENCE: 4
RSSKSLLHSN GITYLY                                           16

SEQ ID NO: 5            moltype = AA  length = 7
FEATURE                 Location/Qualifiers
REGION                  1..7
                        note = Synthetic Construct
source                  1..7
                        mol_type = protein
                        organism = synthetic construct
SEQUENCE: 5
QMSNLVS                                                     7

SEQ ID NO: 6            moltype = AA  length = 9
FEATURE                 Location/Qualifiers
REGION                  1..9
                        note = Synthetic Construct
source                  1..9
                        mol_type = protein
                        organism = synthetic construct
SEQUENCE: 6
AQNLELPYT                                                   9

SEQ ID NO: 7            moltype = AA  length = 119
FEATURE                 Location/Qualifiers
REGION                  1..119
                        note = Synthetic Construct
source                  1..119
                        mol_type = protein
                        organism = synthetic construct
SEQUENCE: 7
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 8            moltype = AA  length = 115
FEATURE                 Location/Qualifiers
REGION                  1..115
                        note = Synthetic Construct
source                  1..115
                        mol_type = protein
                        organism = synthetic construct
SEQUENCE: 8
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IKRTV       115

SEQ ID NO: 9            moltype = AA  length = 448
FEATURE                 Location/Qualifiers
REGION                  1..448
                        note = Synthetic Construct
source                  1..448
                        mol_type = protein
                        organism = synthetic construct
SEQUENCE: 9
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 10           moltype = AA  length = 219
FEATURE                 Location/Qualifiers
REGION                  1..219
                        note = Synthetic Construct
```

-continued

```
source                  1..219
                        mol_type = protein
                        organism = synthetic construct
SEQUENCE: 10
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 11           moltype = AA  length = 112
FEATURE                 Location/Qualifiers
source                  1..112
                        mol_type = protein
                        organism = Mus musculus
SEQUENCE: 11
GPELVKPGAS VKISCKASGY AFSYSWMNWV KLRPGQGLEW IGRIFPGDGD TDYNGKFKGK  60
ATLTADKSSN TAYMQLTSLT SVDSAVYLCA RNVFDGYWLV YWGQGTLVTV SA          112

SEQ ID NO: 12           moltype = AA  length = 103
FEATURE                 Location/Qualifiers
source                  1..103
                        mol_type = protein
                        organism = Mus musculus
SEQUENCE: 12
NPVTLGTSAS ISCRSSKSLL HSNGITYLYW YLQKPGQSPQ LLIYQMSNLV SGVPDRFSSS  60
GSGTDFTLRI SRVEAEDVGV YYCAQNLELP YTFGGGTKLE IKR                    103

SEQ ID NO: 13           moltype = AA  length = 119
FEATURE                 Location/Qualifiers
REGION                  1..119
                        note = Synthetic Construct
source                  1..119
                        mol_type = protein
                        organism = synthetic construct
SEQUENCE: 13
QVQLVQSGAE VKKPGSSVKV SCKASGYTFS YSWMSWVRQA PGQGLEWMGR IFPGDGDTDY  60
AQKFQGRVTI TADKSTSTAY MELSSLRSED TAVYYCARNV FDGYWLVYWG QGTLVTVSS   119

SEQ ID NO: 14           moltype = AA  length = 119
FEATURE                 Location/Qualifiers
REGION                  1..119
                        note = Synthetic Construct
source                  1..119
                        mol_type = protein
                        organism = synthetic construct
SEQUENCE: 14
QVQLVQSGAE VKKPGSSVKV SCKASGYAFS YSWMNWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 15           moltype = AA  length = 119
FEATURE                 Location/Qualifiers
REGION                  1..119
                        note = Synthetic Construct
source                  1..119
                        mol_type = protein
                        organism = synthetic construct
SEQUENCE: 15
QVQLVQSGAE VKKPGSSVKV SCKASGYAFS YSWMNWVRQA PGQGLEWMGR IFPGDGDTDY  60
NGKFKGRVTI TADKSTSTAY MELSSLRSED TAVYLCARNV FDGYWLVYWG QGTLVTVSS   119

SEQ ID NO: 16           moltype = AA  length = 119
FEATURE                 Location/Qualifiers
REGION                  1..119
                        note = Synthetic Construct
source                  1..119
                        mol_type = protein
                        organism = synthetic construct
SEQUENCE: 16
QVQLVQSGAE VKKPGASVKV SCKVSGYAFS YSWMNWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 17           moltype = AA  length = 119
FEATURE                 Location/Qualifiers
REGION                  1..119
                        note = Synthetic Construct
source                  1..119
                        mol_type = protein
                        organism = synthetic construct
SEQUENCE: 17
```

```
QVQLVQSGAE VKKPGSSVKV SCKASGYAFS YSWMSWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 18          moltype = AA  length = 119
FEATURE                Location/Qualifiers
REGION                 1..119
                       note = Synthetic Construct
source                 1..119
                       mol_type = protein
                       organism = synthetic construct
SEQUENCE: 18
QVQLVQSGAE VKKPGSSVKV SCKASGYAFS YSWISWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 19          moltype = AA  length = 119
FEATURE                Location/Qualifiers
REGION                 1..119
                       note = Synthetic Construct
source                 1..119
                       mol_type = protein
                       organism = synthetic construct
SEQUENCE: 19
QVQLVQSGAE VKKPGASVKV SCKASGYTFT YSWMNWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 20          moltype = AA  length = 119
FEATURE                Location/Qualifiers
REGION                 1..119
                       note = Synthetic Construct
source                 1..119
                       mol_type = protein
                       organism = synthetic construct
SEQUENCE: 20
QVQLVQSGAE VKKPGASVKV SCKASGYTFS YSWMNWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 21          moltype = AA  length = 119
FEATURE                Location/Qualifiers
REGION                 1..119
                       note = Synthetic Construct
source                 1..119
                       mol_type = protein
                       organism = synthetic construct
SEQUENCE: 21
QVQLVQSGAE VKKPGASVKV SCKASGYTFT YSWMHWVRQA PGQGLEWMGR IFPGDGDTDY  60
AQKFQGRVTM TRDTSTSTVY MELSSLRSED TAVYYCARNV FDGYWLVYWG QGTLVTVSS   119

SEQ ID NO: 22          moltype = AA  length = 119
FEATURE                Location/Qualifiers
REGION                 1..119
                       note = Synthetic Construct
source                 1..119
                       mol_type = protein
                       organism = synthetic construct
SEQUENCE: 22
EVQLVQSGAE VKKPGATVKI SCKVSGYTFT YSWMHWVQQA PGKGLEWMGR IFPGDGDTDY  60
AEKFQGRVTI TADTSTDTAY MELSSLRSED TAVYYCATNV FDGYWLVYWG QGTLVTVSS   119

SEQ ID NO: 23          moltype = AA  length = 119
FEATURE                Location/Qualifiers
REGION                 1..119
                       note = Synthetic Construct
source                 1..119
                       mol_type = protein
                       organism = synthetic construct
SEQUENCE: 23
EVQLVQSGAE VKKPGATVKI SCKVSGYTFT YSWMNWVQQA PGKGLEWMGR IFPGDGDTDY  60
NGKFKGRVTI TADTSTDTAY MELSSLRSED TAVYYCATNV FDGYWLVYWG QGTLVTVSS   119

SEQ ID NO: 24          moltype = AA  length = 119
FEATURE                Location/Qualifiers
REGION                 1..119
                       note = Synthetic Construct
source                 1..119
                       mol_type = protein
                       organism = synthetic construct
SEQUENCE: 24
QMQLVQSGAE VKKTGSSVKV SCKASGYTFT YSWMSWVRQA PGQGLEWMGR IFPGDGDTDY  60
AQKFQGRVTI TADKSTSTAY MELSSLRSED TAVYYCARNV FDGYWLVYWG QGTLVTVSS   119
```

```
SEQ ID NO: 25          moltype = AA  length = 119
FEATURE                Location/Qualifiers
REGION                 1..119
                       note = Synthetic Construct
source                 1..119
                       mol_type = protein
                       organism = synthetic construct
SEQUENCE: 25
EVQLVESGGG LVKPGGSLRL SCAASGFTFS YSWMNWVRQA PGKGLEWVGR IFPGDGDTDY  60
NGKFKGRVTI TADKSTSTAY MELSSLRSED TAVYYCARNV FDGYWLVYWG QGTLVTVSS   119

SEQ ID NO: 26          moltype = AA  length = 119
FEATURE                Location/Qualifiers
REGION                 1..119
                       note = Synthetic Construct
source                 1..119
                       mol_type = protein
                       organism = synthetic construct
SEQUENCE: 26
EVQLVESGGG LVKPGGSLRL SCAASGFAFS YSWMNWVRQA PGKGLEWVGR IFPGDGDTDY  60
NGKFKGRVTI TADKSTSTAY MELSSLRSED TAVYYCARNV FDGYWLVYWG QGTLVTVSS   119

SEQ ID NO: 27          moltype = AA  length = 119
FEATURE                Location/Qualifiers
REGION                 1..119
                       note = Synthetic Construct
source                 1..119
                       mol_type = protein
                       organism = synthetic construct
SEQUENCE: 27
QVQLVESGGG LVKPGGSLRL SCAASGFTFS YSWMNWVRQA PGKGLEWVGR IFPGDGDTDY  60
NGKFKGRVTI TADKSTSTAY MELSSLRSED TAVYYCARNV FDGYWLVYWG QGTLVTVSS   119

SEQ ID NO: 28          moltype = AA  length = 119
FEATURE                Location/Qualifiers
REGION                 1..119
                       note = Synthetic Construct
source                 1..119
                       mol_type = protein
                       organism = synthetic construct
SEQUENCE: 28
EVQLVESGAG LVKPGGSLRL SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 29          moltype = AA  length = 119
FEATURE                Location/Qualifiers
REGION                 1..119
                       note = Synthetic Construct
source                 1..119
                       mol_type = protein
                       organism = synthetic construct
SEQUENCE: 29
EVQLVESGGG VVKPGGSLRL SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 30          moltype = AA  length = 119
FEATURE                Location/Qualifiers
REGION                 1..119
                       note = Synthetic Construct
source                 1..119
                       mol_type = protein
                       organism = synthetic construct
SEQUENCE: 30
EVQLVESGGG LKKPGGSLRL SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 31          moltype = AA  length = 119
FEATURE                Location/Qualifiers
REGION                 1..119
                       note = Synthetic Construct
source                 1..119
                       mol_type = protein
                       organism = synthetic construct
SEQUENCE: 31
EVQLVESGGG LVKPGSSLRL SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 32          moltype = AA  length = 119
```

```
FEATURE                Location/Qualifiers
REGION                 1..119
                       note = Synthetic Construct
source                 1..119
                       mol_type = protein
                       organism = synthetic construct
SEQUENCE: 32
EVQLVESGGG LVKPGGSLRV SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 33          moltype = AA  length = 119
FEATURE                Location/Qualifiers
REGION                 1..119
                       note = Synthetic Construct
source                 1..119
                       mol_type = protein
                       organism = synthetic construct
SEQUENCE: 33
EVQLVESGGG LVKPGGSLRL SCAASGFTFS YSWMNWVRQA PGKGLEWMGR IFPGDGDTDY  60
NGKFKGRVTI TADKSTSTAY MELSSLRSED TAVYYCARNV FDGYWLVYWG QGTLVTVSS   119

SEQ ID NO: 34          moltype = AA  length = 19
FEATURE                Location/Qualifiers
REGION                 1..19
                       note = Synthetic Construct
source                 1..19
                       mol_type = protein
                       organism = synthetic construct
SEQUENCE: 34
MDWTWRILFL VAAATGAHS                                               19

SEQ ID NO: 35          moltype = AA  length = 25
FEATURE                Location/Qualifiers
REGION                 1..25
                       note = Synthetic Construct
source                 1..25
                       mol_type = protein
                       organism = synthetic construct
SEQUENCE: 35
EVQLVESGGG LVQPGGSLRL SCAAS                                        25

SEQ ID NO: 36          moltype = AA  length = 13
FEATURE                Location/Qualifiers
REGION                 1..13
                       note = Synthetic Construct
source                 1..13
                       mol_type = protein
                       organism = synthetic construct
SEQUENCE: 36
WVRQAPGKGL EWV                                                     13

SEQ ID NO: 37          moltype = AA  length = 32
FEATURE                Location/Qualifiers
REGION                 1..32
                       note = Synthetic Construct
source                 1..32
                       mol_type = protein
                       organism = synthetic construct
SEQUENCE: 37
RFTISADTSK NTAYLQMNSL RAEDTAVYYC AR                                32

SEQ ID NO: 38          moltype = AA  length = 11
FEATURE                Location/Qualifiers
REGION                 1..11
                       note = Synthetic Construct
source                 1..11
                       mol_type = protein
                       organism = synthetic construct
SEQUENCE: 38
WGQGTLVTVS A                                                       11

SEQ ID NO: 39          moltype = AA  length = 23
FEATURE                Location/Qualifiers
REGION                 1..23
                       note = Synthetic Construct
source                 1..23
                       mol_type = protein
                       organism = synthetic construct
SEQUENCE: 39
```

-continued

```
DIQMTQSPSS LSASVGDRVT ITC                                      23

SEQ ID NO: 40          moltype = AA  length = 15
FEATURE                Location/Qualifiers
REGION                 1..15
                       note = Synthetic Construct
source                 1..15
                       mol_type = protein
                       organism = synthetic construct
SEQUENCE: 40
WYQQKPGKAP KLLIY                                               15

SEQ ID NO: 41          moltype = AA  length = 32
FEATURE                Location/Qualifiers
REGION                 1..32
                       note = Synthetic Construct
source                 1..32
                       mol_type = protein
                       organism = synthetic construct
SEQUENCE: 41
GVPSRFSGSG SGTDFTLTIS SLQPEDFATY YC                            32

SEQ ID NO: 42          moltype = AA  length = 11
FEATURE                Location/Qualifiers
REGION                 1..11
                       note = Synthetic Construct
source                 1..11
                       mol_type = protein
                       organism = synthetic construct
SEQUENCE: 42
FGQGTKVEIK R                                                   11

SEQ ID NO: 43          moltype = AA  length = 22
FEATURE                Location/Qualifiers
REGION                 1..22
                       note = Synthetic Construct
source                 1..22
                       mol_type = protein
                       organism = synthetic construct
SEQUENCE: 43
MDMRVPAQLL GLLLLWFPGA RC                                       22
```